(12) United States Patent
Bengtsson et al.

(10) Patent No.: US 12,115,015 B2
(45) Date of Patent: Oct. 15, 2024

(54) DEEP CONVOLUTIONAL NEURAL NETWORKS FOR TUMOR SEGMENTATION WITH POSITRON EMISSION TOMOGRAPHY

(71) Applicant: GENENTECH, INC., South San Francisco, CA (US)

(72) Inventors: Nils Gustav Thomas Bengtsson, San Francisco, CA (US); Richard Alan Duray Carano, San Ramon, CA (US); Alexander James Stephen Champion de Crespigny, Redwood City, CA (US); Jill Osborn Fredrickson, Sunnyvale, CA (US); Mohamed Skander Jemaa, San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 358 days.

(21) Appl. No.: 17/473,495

(22) Filed: Sep. 13, 2021

(65) Prior Publication Data

US 2021/0401392 A1    Dec. 30, 2021

Related U.S. Application Data

(63) Continuation of application No. PCT/US2020/022864, filed on Mar. 14, 2020.
(Continued)

(51) Int. Cl.
*A61B 6/00* (2024.01)
*G06N 3/02* (2006.01)
(Continued)

(52) U.S. Cl.
CPC .......... *A61B 6/5217* (2013.01); *A61B 6/5235* (2013.01); *A61B 6/5247* (2013.01);
(Continued)

(58) Field of Classification Search
None
See application file for complete search history.

(56) References Cited

U.S. PATENT DOCUMENTS

| 2005/0065421 A1 | 3/2005 | Burckhardt |
| 2012/0123253 A1* | 5/2012 | Renisch ............... A61B 6/5217 |
| | | 600/425 |

(Continued)

FOREIGN PATENT DOCUMENTS

| CN | 103942785 A | 7/2014 |
| CN | 109308728 A | 2/2019 |
| WO | 2018200493 A1 | 11/2018 |

OTHER PUBLICATIONS

Guo et al., "Deep Learning-Based Image Segmentation on Multimodal Medical D1 Imaging", IEEE Transactions on Radiation and Plasma Medical Sciences, IEEE, vol. 3, No. 2, Mar. 1, 2019, pp. 162-169 (Year: 2019).*

(Continued)

*Primary Examiner* — Jonathan Cwern
(74) *Attorney, Agent, or Firm* — Kilpatrick Townsend & Stockton LLP

(57) ABSTRACT

The present disclosure relates to techniques for segmenting tumors with positron emission tomography (PET) using deep convolutional neural networks for image and lesion metabolism analysis. Particularly, aspects of the present disclosure are directed to obtaining a PET scans and computerized tomography (CT) or magnetic resonance imaging (MRI) scans for a subject, preprocessing the PET scans and the CT or MRI scans to generate standardized images, generating two-dimensional segmentation masks, using two-dimensional segmentation models implemented as part of a convolutional neural network architecture that takes as input the standardized images, generating three-dimensional segmentation masks, using three-dimensional segmentation (Continued)

models implemented as part of the convolutional neural network architecture that takes as input patches of image data associated with segments from the two-dimensional segmentation mask, and generating a final imaged mask by combining information from the two-dimensional segmentation masks and the three-dimensional segmentation masks.

20 Claims, 25 Drawing Sheets

Related U.S. Application Data

(60) Provisional application No. 62/880,898, filed on Jul. 31, 2019, provisional application No. 62/819,275, filed on Mar. 15, 2019.

(51) Int. Cl.

| | |
|---|---|
| *G06T 7/11* | (2017.01) |
| *G06T 7/174* | (2017.01) |
| *G16H 10/20* | (2018.01) |
| *G16H 30/20* | (2018.01) |
| *G16H 30/40* | (2018.01) |
| *G16H 50/20* | (2018.01) |
| *G16H 50/30* | (2018.01) |
| *G16H 50/50* | (2018.01) |

(52) U.S. Cl.
CPC .............. *G06N 3/02* (2013.01); *G06T 7/11* (2017.01); *G06T 7/174* (2017.01); *G16H 10/20* (2018.01); *G16H 30/20* (2018.01); *G16H 30/40* (2018.01); *G16H 50/20* (2018.01); *G16H 50/30* (2018.01); *G16H 50/50* (2018.01); *G06T 2207/10088* (2013.01); *G06T 2207/10104* (2013.01); *G06T 2207/20016* (2013.01); *G06T 2207/20084* (2013.01); *G06T 2207/30096* (2013.01); *G06T 2207/30242* (2013.01)

(56) References Cited

U.S. PATENT DOCUMENTS

| | | | | |
|---|---|---|---|---|
| 2018/0165808 | A1 | 6/2018 | Bagci et al. | |
| 2019/0057778 | A1 | 2/2019 | Porter et al. | |
| 2019/0155973 | A1* | 5/2019 | Morczinek | G01C 11/04 |
| 2019/0332900 | A1* | 10/2019 | Sjolund | G06T 9/002 |
| 2020/0380675 | A1* | 12/2020 | Golden | G06T 7/143 |
| 2021/0004960 | A1* | 1/2021 | Groth | G16H 15/00 |

OTHER PUBLICATIONS

"KiTS19 Challenge Homepage", website related to the 2019 Kidney Segmentation Challenge, , retrieved Oct. 5, 2021, https://kits19.grand-challenge.org/, 2 pages.

"Medical Segmentation Decathlon", website, retrieved Oct. 5, 2021, 7 pages. http://medicaldecathlon.com/.

"Segment Lungs from 3-D Chest Scan and Calculate Lung Volume", Mathworks :https://www.mathworks.com/help/images/segment-lungs-from-3-d-chest-mri-data.html, Last accessed Mar. 11, 2019, 8 pages.

Bauer C, Sun S, Sun W, et al. "Automated Measurement of Uptake in Cerebellum, Liver, and Aortic Arch in Full-Body", FDG PET/CT scans. Med Phys., May 2012; 39(6):3112-23, https://doi.org/10.1118/1.4711815.

Cai, J., et al.,: "Accurate Weakly-Supervised Deep Lesion Segmentation Using Large-Scale Clinical Annotations: Slice-Propagated 3D Mask Generation from2D Recist". In: Frangi, AF., Schnabel, J. A, Davatzikos, C., Alberola-Lopez, C., Fichtinger, G. Medical Image Computing and Computer Assisted Intervention MICCAI 2018, 2018,pp. 396-404, Springer International Publishing, Jan. 2018.

Cheson, B., et al.,: "Recommendations for Initial Evaluation, Staging, and Response Assessment of Hodgkin and Non-Hodgkin Lymphoma: The Lugano Classication", Journal of Clinical Oncology 32(27), 3059-3067, Sep. 20, 2014, https://doi.org/10.1200/JC0.2013.54.8800.

Cheson, B., et.al., "Revised Response Criteria for Malignant Lymphoma". Journal of Clinical Oncology, 25(5), 579-586, Feb. 10, 2007, https://doi.org/10.1200/JC0.2006.09.2403.

Gambhir, S. S., et al.,:"A Tabulated Summary of the FDG PET Literature", Journal of Nuclear Medicine, 42(5 suppl), 1S-93S May 2001.

Guo Zhe, et al.,: "Deep Learning-Based Image Segmentation on Multimodal Medical D1 Imaging", IEEE Transactions on Radiation and Plasma Medical Sciences, IEEE, vol. 3, No. 2, Mar. 1, 2019 (Mar. 1, 2019), pp. 162-169.

He, K., Gkioxari, G., Dollr, P., Girshick, P.: "Mask R-CNN", In: 2017 IFFE International Conference on Computer Vision, pp. 2980-2988. IEEE (2017) https://doi.org/10.1109/ICCV.2017.322.

He, K., Zhang, X., Ren, S., Sun,J.: "Deep Residual Learning for Image Recognition", CoRR, abs/1512.03385, Dec. 2015, 12 pages.

Hoogi, et, al., "Adaptive Local Window for Level Set Segmentation of CT and MRI Liver Lesions", Med. Image Analysis, Apr. 2017; 46-55. doi: 10.1016/j.media.2017.01.002.

Huang, B., Chen, Z., Wu, P.-M., et .al.,: "Fully Automated Delineation of Gross Tumor vol. for Head and Neck Cancer on PET-CT Using Deep Learning: A Dual-Center Study", Contrast Media & Molecular Imaging, vol. 2018, article ID 8923028, 13 pages, Oct. 2018, https://doi.org/10.1155/2018/8923028.

Jain, et al., "Biophysical Properties of the Clinical-Stage Antibody Landscape", PNAS, vol. 114, No. 5 accepted Dec. 13, 2016, published Jan. 31, 2017, pp. 944-949.

Jemaa, et al., Deep Learning for Automated Tumor Burden Assessment fromPDG-PET, submitted Apr. 10, 2019 (abstract), 1 page.

Kamnitsas, K., et. al,.: "Efficient Multi-Scale 3D CNN With Fully Connected CRF for Accurate Brain Lesion Segmentation", Medical Image Analysis 36, Jan. 2017, 49 pages.

Kelloff, G., et al.,: "Progress and Promise of FDG-PET Imaging for Cancer Patient Management and Oncologic Drug Development". American Association for Cancer Research 11(8), 2785-2808 Apr. 15, 2005.

Kingma, D.P., Ba, J.: Adam: "A Method for Stochastic Optimization". In: 2015 Proceedings of the 3rd International Conference on Learning Representations (ICLR). Preprint at http://arxiv.org/abs/1412.6980 Jan. 30, 2017, 15 pages.

Long, J., Shelhamer, E., Darrell, T., "Fully Convolutional Networks for Semantic Segmentation, CVPR", pp. 3431-3440, IEFE Computer Society, Oct. 2015, https://doi.org/10.1109/CVPR.2015.7298965.

Lu et al. "Deamidation and isomerization liability analysis of 131 clinical-stage antibodies", mAbs, Taylor and Francis, Dec. 10, 2018, https://doi.org/10.1080/19420862.2018.1548233, 14 pages.

Milletari, F., Navab, N., Ahmadi, S.: "V-Net: Fully Convolutional Neural Networks for Volumetric Medical Image Segmentation", in Proc. Fourth International Conference on 3D Vision (3DV), Jun. 2016, pp. 565-571,(2016), https://doi.org/10.1109/3DV.2016.79.

Ronneberger, 0., Fischer, P., Brox, T.: U-Net: "Convolutional Networks for Biomedical Image Segmentation, :Medical Image Computing and ComputerAssisted Intervention" (MICCAI), Springer, LNCS, pp. 234 (241, vol. 9351, May 2015. https://doi.org/ 10.1007/978-3-319-24574-428.

Teramoto, A, Fujita, H., Yamamuro, 0., Tamaki, T.: "Automated Detection of Pulmonary Nodules in PET/CT Images": Ensemble False-positive Reduction Using a Convolutional Neural Network Technique, Medical Physics, 49(6), 2821-2827, May 2016.

Valindria Vanya, et. al,: "Multi-modal Learning from Unpaired Images: Application to D3 Multi-organ Segmentation in CT and MRI", 2018 IEEE Winter Conference on Applications of Computer Vision (WACV), (Mar. 12, 2018), pp. 547-556.

Yan, K., et. al.,: "Deep Lesion: Automated Mining of Large-Scale Lesion Annotations and Universal Lesion Detection with Deep

(56) References Cited

OTHER PUBLICATIONS

Learning", Journal of Medical Imaging 5(3),L036501 Jul.-Sep. 2018, 12 pages. https://doi.org/10.1117/1.JMI.5.3 .036501.

Young, H., et al. "Measurement of Clinical and Subclinical Tumour Response Using [$^{18}$F]-Florodeoxyglucose and Positron Emission Tomography", Review and 1999 EORTC recommendations, European Journal of Cancer 35(13), 1773-1782 Aug. 1999, https://doi.org/10.1016/S0959-8049(99)00229-4.

Yu F., Koltun, V.: "Multi-Scale Context Aggregation by Dilated Convolutions":, In: International Conference on Learning Representations, Apr. 2016, 13 pages.

Zou, KH., Wareld, SK., Bharatha, A, et. al., "Statistical Validation of Image Segmentation Quality Based on a Spatial Overlap Index". Acad Radiol., 11(2), 178-89, Feb. 2001, https://doi.org/10.1016/S 10766332(03)00671-8.

\* cited by examiner

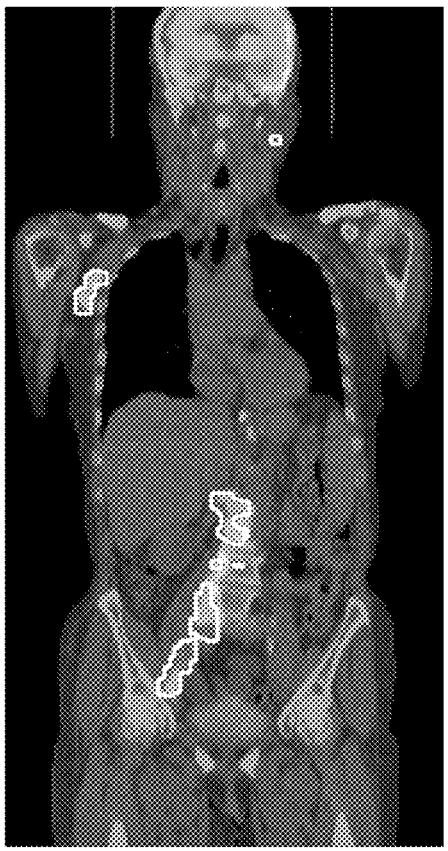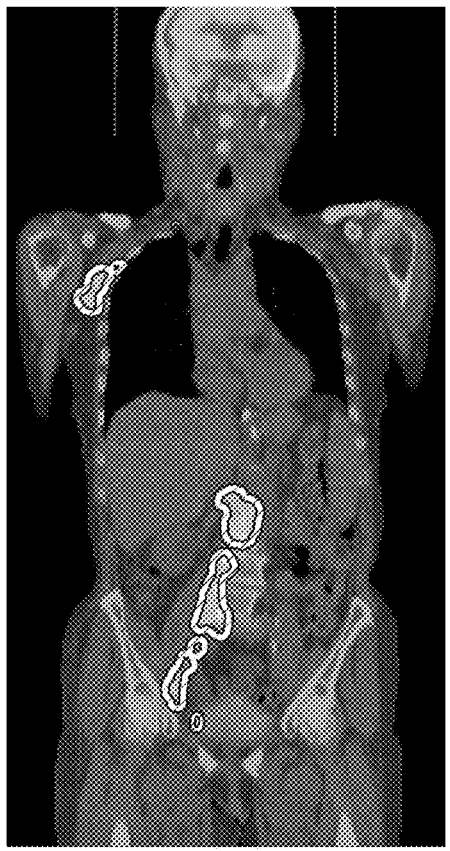
FIG. 9E
FIG. 9F

DEEP CONVOLUTIONAL NEURAL NETWORKS FOR TUMOR SEGMENTATION WITH POSITRON EMISSION TOMOGRAPHY

CROSS-REFERENCE TO RELATED APPLICATIONS

The present application is a continuation filed under 35 U.S.C. § 111(a), which claims priority and benefit from International Application PCT/US2020/022864, filed Mar. 14, 2020, which claims priority and benefit from U.S. Provisional Application No. 62/880,898, filed Jul. 31, 2019, and U.S. Provisional Application No. 62/819,275, filed Mar. 15, 2019, the entire contents of which are incorporated herein by reference for all purposes.

FIELD

The present disclosure relates to automated tumor segmentation, and in particular to systems and methods for segmenting tumors in positron emission tomography images using deep convolutional neural networks for image and lesion metabolism analysis.

BACKGROUND

Positron emission tomography (PET), also called PET imaging or a PET scan, is a type of nuclear medicine imaging test that helps reveal how tissues and organs are functioning. A PET scan uses a radioactive drug (tracer) to show this activity. A tracer is a molecule linked to, or labeled with, a radioactive tag that can be detected on the PET scan. The tracer may be injected, swallowed or inhaled, depending on which organ or tissue is being studied. The tracer collects in areas of a body (e.g., cancerous tumors or regions of inflammation) that have higher metabolic activity or bind to specific proteins in the body, which often correspond to areas of disease. On a PET scan, these areas show up as bright spots. The most commonly used radiotracer is fluorodeoxyglucose (FDG), a molecule similar to glucose. In FDG-PET, tissues or areas that have higher metabolic activity than their surroundings will show as bright spots. For example, cancer cells may absorb glucose at a higher rate, being more metabolically active. This higher rate can be seen on a PET scan, and allows a health care provider to identify a tumor before it may be seen on other imaging tests. PET scans may help diagnose and determine the severity of a variety of diseases, including many types of cancers, heart disease, gastrointestinal, endocrine, neurological disorders and other abnormalities within the body.

SUMMARY

In various embodiments, a computer-implemented method is provided comprising: obtaining a plurality of positron emission tomography (PET) scans and a plurality of computerized tomography (CT) or magnetic resonance imaging (MRI) scans for a subject; preprocessing the PET scans and the CT or MRI scans to generate a first subset of standardized images for a first plane or region of the subject and a second subset of standardized images for a second plane or region of the subject, where the first subset of standardized images and the second subset of standardized images incorporate information from the PET scans and the CT or MRI scans; generating a first two-dimensional segmentation mask, using a first two-dimensional segmentation model implemented as part of a convolutional neural network architecture that takes as input the first subset of standardized images, where the first two-dimensional segmentation model uses a first residual block comprising a first layer that: (i) feeds directly into a subsequent layer, and (ii) uses a skip connection to feed directly into a layer that is multiple layers away from the first layer; generating a second two-dimensional segmentation mask, using a second two-dimensional segmentation model implemented as part of the convolutional neural network architecture that takes as input the second subset of standardized images, where the second two-dimensional segmentation model uses a second residual block comprising a second layer that: (i) feeds directly into a subsequent layer, and (ii) uses a skip connection to feed directly into a layer that is multiple layers away from the second layer; and generating a final imaged mask by combining information from the first two-dimensional segmentation mask and the second two-dimensional segmentation mask.

In some embodiments, the first layer and the second layer are pyramidal layers with separable convolutions performed at one or more levels of dilation.

In some embodiments, the method further comprises determining, using the final imaged mask, a total metabolic tumor burden (TMTV), and providing the TMTV.

In some embodiments, the method further comprises: generating a three-dimensional organ mask, using a three-dimensional organ segmentation model that takes as input the PET scans and the CT or MRI scans; determining, using the final imaged mask and the three-dimensional organ mask, a metabolic tumor burden (MTV) and number of lesions for one or more organs in the three-dimensional organ segmentation; and providing the MTV and number of lesions for the one or more organs.

In some embodiments, the method further comprises: using a classifier that takes as input one or more of the TMTV, the MTV, and the number of lesions to generate a clinical prediction for the subject based on one or more of the TMTV, the MTV, and the number of lesions, where the clinical prediction is one of: a likelihood of progression free survival (PFS) for the subject; a disease stage of the subject; and a selection decision for including the subject in a clinical trial.

In some embodiments, the method further comprises: inputting, by a user, the plurality of PET scans and CT or MRI scans for the subject into a data processing system comprising the convolutional neural network architecture; providing the final imaged mask; and receiving, by the user, one or more of the final imaged mask, the TMTV, the MTV, and the number of lesions on a display of a computing device.

In some embodiments, the method further comprises administering, by the user, a treatment to the subject based on one or more of the final imaged mask, the TMTV, the MTV, and the number of lesions.

In some embodiments, the method further comprises providing, by the user, a diagnosis to the subject based on one or more of the final imaged mask, the TMTV, the MTV, and the number of lesions.

In various embodiments, a computer-implemented method is provide comprising: obtaining a plurality of positron emission tomography (PET) scans and a plurality of computerized tomography (CT) or magnetic resonance imaging (MRI) scans for a subject; preprocessing the PET scans and the CT or MRI scans to generate standardized images incorporating information from the PET scans and the CT or MRI scans; generating one or more two-dimensional segmentation masks, using one or more two-dimensional segmentation models implemented as part of a convolutional neural network architecture that takes as input the standardized images; generating one or more three-dimensional segmentation masks, using one or more three-dimensional segmentation models implemented as part of the convolutional neural network architecture that takes as input patches of image data associated with segments from the two-dimensional segmentation mask; and generating a final imaged mask by combining information from the one or more two-dimensional segmentation masks and the one or more three-dimensional segmentation masks.

In some embodiments, the one or more three-dimensional segmentation models comprise a first three-dimensional segmentation model and a second three-dimensional segmentation model; the patches of image data comprise a first patch of image data associated with a first segment and a second patch of image data associated with a second segment; and the generating the one or more three-dimensional segmentation masks comprises: generating a first three-dimensional segmentation mask, using the first three-dimensional segmentation model that takes as input the first patch of image data, and generating a second three-dimensional segmentation mask, using the second three-dimensional segmentation model that takes as input the second patch of image data.

In some embodiments, the method further comprises: assessing a location of components of a region or body captured in the standardized images as reference points; splitting the region or body into multiple anatomical regions based on the reference points; generating location labels for the multiple anatomical regions; incorporating the location labels within the two-dimensional segmentation mask; determining the first segment is located in a first anatomical region of the multiple anatomical regions based on the location labels; determining the second segment is located in a second anatomical region of the multiple anatomical regions based on the location labels; inputting the first patch of image data associated with the first segment into the first three-dimensional segmentation mask based on the determination that the first segment is located in the first anatomical region; and inputting the second patch of image data associated with the second segment into the second three-dimensional segmentation mask based on the determination that the second segment is located in the second anatomical region.

In some embodiments, the standardized images comprise a first subset of standardized images for a first plane or region of the subject and a second subset of standardized images for a second plane or region of the subject, where the first subset of standardized images and the second subset of standardized images incorporate information from the PET scans and the CT or MRI scans; the one or more two-dimensional segmentation models comprise a first two-dimensional segmentation model and a second two-dimensional segmentation model; and the generating the one or more two-dimensional segmentation masks comprises: generating a first two-dimensional segmentation mask, using the first two-dimensional segmentation model implemented that takes as input the first subset of standardized images, where the first two-dimensional segmentation model uses a first residual block comprising a first layer that: (i) feeds directly into a subsequent layer, and (ii) uses a skip connection to feed directly into a layer that is multiple layers away from the first layer; and generating a second two-dimensional segmentation mask, using the second two-dimensional segmentation model that takes as input the second subset of standardized images, where the second two-dimensional segmentation model uses a second residual block comprising a second layer that: (i) feeds directly into a subsequent layer, and (ii) uses a skip connection to feed directly into a layer that is multiple layers away from the second layer.

In some embodiments, the first layer and the second layer are pyramidal layers with separable convolutions performed at one or more levels of dilation.

In some embodiments, the method further comprises determining, using the final imaged mask, a total metabolic tumor burden (TMTV), and providing the TMTV.

In some embodiments, the method further comprises: generating a three-dimensional organ mask, using a three-dimensional organ segmentation model that takes as input the PET scans and the CT or MRI scans; determining, using the final imaged mask and the three-dimensional organ mask, a metabolic tumor burden (MTV) and number of lesions for one or more organs in the three-dimensional organ segmentation; and providing the MTV and number of lesions for the one or more organs.

In some embodiments, the method further comprises: using a classifier that takes as input one or more of the TMTV, the MTV, and the number of lesions to generate a clinical prediction for the subject based on one or more of the TMTV, the MTV, and the number of lesions, where the clinical prediction is one of: a likelihood of progression free survival (PFS) for the subject; a disease stage of the subject; and a selection decision for including the subject in a clinical trial.

In some embodiments, the method further comprises: inputting, by a user, the plurality of PET scans and CT or MRI scans for the subject into a data processing system comprising the convolutional neural network architecture; providing the final imaged mask; and receiving, by the user, one or more of the final imaged mask, the TMTV, the MTV, and the number of lesions on a display of a computing device.

In some embodiments, the method further comprises administering, by the user, a treatment to the subject based on one or more of the final imaged mask, the TMTV, the MTV, and the number of lesions.

In some embodiments, the method further comprises providing, by the user, a diagnosis to the subject based on one or more of the final imaged mask, the TMTV, the MTV, and the number of lesions.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures:

FIGS. 9A-9F show segmentation results according to various embodiments;

Figure 1:
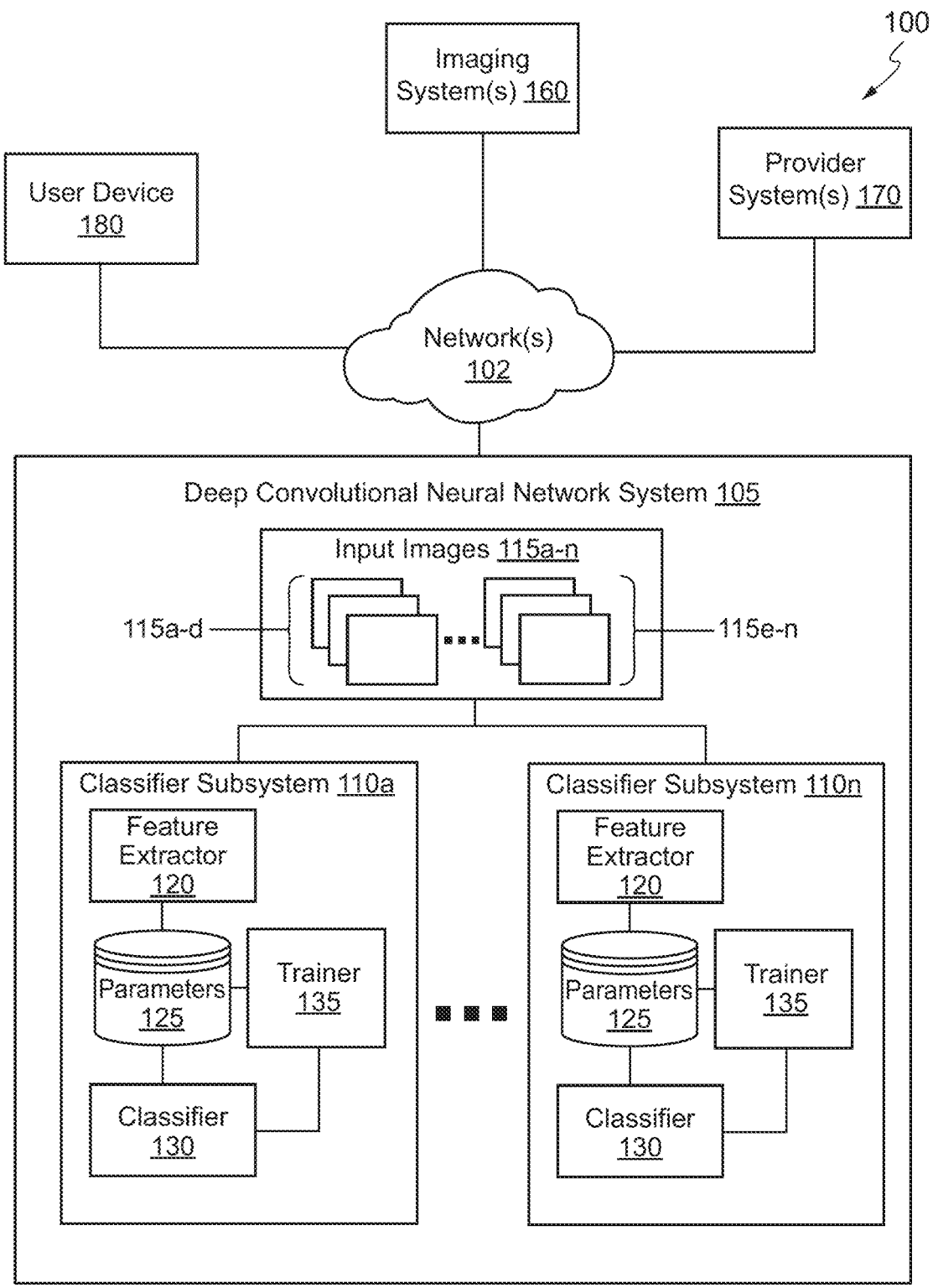
FIG. 1 shows an example computing environment for automated tumor segmentation using a cascading convolutional neural network according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

The present disclosure describes techniques for automated tumor segmentation. More specifically, some embodiments of the present disclosure provide systems and methods for segmenting tumors in positron emission tomography images using deep convolutional neural networks for image and lesion metabolism analysis.

The use of standardized uptake values (SUVs) is now common place in clinical PET/CT oncology imaging, and has a specific role in assessing subject response to therapy. The use of fluorodeoxyglucose (FDG) for oncology imaging accounts for the majority of all positron emission tomography (PET)/computerized tomography (CT) (PET/CT) imaging procedures since increased accumulation of FDG relative to normal tissue is a useful marker for many cancers. In addition, PET/CT imaging is becoming more important as a quantitative monitor of individual response to therapy and an evaluation tool for new drug therapies. For example, changes in FDG accumulation have been shown to be useful as an imaging biomarker for assessing response to therapy. There are several methods for measuring the rate and/or total amount of FDG accumulation in tumors. PET scanners are designed to measure the in vivo radioactivity concentration [kBq/ml], which is directly linked to the FDG concentration. Typically, however, it is the relative tissue uptake of FDG that is of interest. The two most significant sources of variation that occur in practice are the amount of injected FDG and the subject size. To compensate for these variations, the SUV is used as a relative measure of FDG uptake. Ideally, the use of SUV reduces the variability of the signal depending on the injected dose of radio tracer and its consumption and is defined in Equation (1).

$$SUV = \frac{\text{Activity} * \text{Weight}}{1000 * \frac{\text{Dose} * \ln(2)}{T_{\frac{1}{2}}}} \quad \text{Equation (1)}$$

where activity is the radioactivity activity concentration [kBq/ml] measured by the PET scanner within a region of interest (ROI), dose is the decay-corrected amount of injected radiolabeled FDG [Bq], and weight is the weight of the subject [g], which is used as a surrogate for a distribution volume of tracer. The use of SUV as a measurement of relative tissue/organ uptake facilitates comparisons between subjects, and has been suggested as a basis for diagnosis.

However, there are a large number of potential sources of bias and variance in determining SUVs. One of those sources of bias and variance come from the analysis methods used to analyze the tracer uptake in PET images. In an ideal instance, where there is no resolution loss or uncertainty in boundary definition, computing the average SUV within a ROI in PET scans would generate a reliable estimate of the mean SUV for the corresponding tissue. Nonetheless, regional and whole body PET-CTs are challenging as they are large and the proportion of tumorous voxels in each image is low. Regional and whole body PET-CTs also represent a challenge due to the low resolution of FDG-PETs and the low contrast of CTs. These effects contribute to problems with tumor segmentation, which defines the boundary of the ROI over which the average SUV is to be computed, and ultimately creates bias and variance in computing the average SUV.

Automated segmentation of tumors and substructures from PET scans has a potential for accurate and reproducible delineation of the tumors, which can provide more efficient and better diagnosis, surgical planning and treatment assessment of tumors. Most automated tumor segmentation methods use hand designed features. These methods implement a classical machine learning pipeline according to which features are first extracted and then given to a classifier whose training procedure does not affect the nature of those features. An alternative approach for designing task-adapted feature representations is to learn a hierarchy of increasingly complex features directly from in-domain data. However, accurate automated segmentation of tumors from PET scans is a challenging task for several reasons. First, the boundary between tumor and normal tissues is often ambiguous due to specific (e.g., brain) and nonspecific (e.g., blood pool) high metabolic active regions, heterogeneity in low resolution images (e.g., variable density and metabolism of organs), sparse signaling (e.g., tumor tissue(s) commonly represent less than approximately 1% of the image), and the sheer number of body structures to be differentiated from tumors. Second, tumors vary largely across subjects in terms of size, shape, and localization. This prohibits the use of strong priors on shape and localization that are commonly used for robust image analysis in many other applications, such as facial recognition or navigation.

To address these limitations and problems, the techniques for automated tumor segmentation of the present embodiments include the use of a convolutional neural network architecture, that is fast and allows for models to deal with both size and the ambiguous nature of regional and whole body PET-CTs or PET-MRIs. One illustrative embodiment of the present disclosure is directed to a method comprising: obtaining a plurality of positron emission tomography (PET) scans and a plurality of computerized tomography (CT) or magnetic resonance imaging (MRI) scans for a subject, and preprocessing the PET scans and the CT or MRI scans to generate a first subset of standardized images for a first plane or region of the subject and a second subset of standardized images for a second plane or region of the subject. The first subset of standardized images and the second subset of standardized images incorporate information from the PET scans and the CT or MRI scans. The method may further comprise generating a first two-dimensional segmentation mask, using a first two-dimensional segmentation model implemented as part of a convolutional neural network architecture that takes as input the first subset of standardized images. The first two-dimensional segmentation model uses a first residual block comprising a first layer that: (i) feeds directly into a subsequent layer, and (ii) uses a skip connection to feed directly into a layer that is multiple layers away from the first layer. The method may further comprise generating a second two-dimensional segmentation mask, using a second two-dimensional segmentation model implemented as part of the convolutional neural network architecture that takes as input the second subset of standardized images. The second two-dimensional segmentation model uses a second residual block comprising a second layer that: (i) feeds directly into a subsequent layer, and (ii) uses a skip connection to feed directly into a layer that is multiple layers away from the second layer. The method may further comprise generating a final imaged mask by combining information from the first two-dimensional segmentation mask and the second two-dimensional segmentation mask.

Another illustrative embodiment of the present disclosure is directed to a method comprising: obtaining a positron emission tomography (PET) scans and computerized tomography (CT) or magnetic resonance imaging (MRI) scans for a subject, preprocessing the PET scans and the CT or MRI scans to generate standardized images, generating two-dimensional segmentation masks, using two-dimensional segmentation models implemented as part of a convolutional neural network architecture that takes as input the standardized images, generating three-dimensional segmentation masks, using three-dimensional segmentation models implemented as part of the convolutional neural network architecture that takes as input patches of image data associated with segments from the two-dimensional segmentation mask, and generating a final imaged mask by combining information from the two-dimensional segmentation masks and the three-dimensional segmentation masks. In some instances, the one or more three-dimensional segmentation models comprise a first three-dimensional segmentation model and a second three-dimensional segmentation model, the patches of image data comprise a first patch of image data associated with a first segment and a second patch of image data associated with a second segment, and the generating the one or more three-dimensional segmentation masks comprises: (i) generating a first three-dimensional segmentation mask, using the first three-dimensional segmentation model that takes as input the first patch of image data and (ii) generating a second three-dimensional segmentation mask, using the second three-dimensional segmentation model that takes as input the second patch of image data.

Advantageously, these approaches include a convolutional neural network architecture that utilizes two-dimensional segmentation models (modified U-Nets) that allow for optimal blending of local and general characteristics in the images and optionally three-dimensional segmentation models (modified V-Nets) that perform volumetric segmentation of objects in a fast and accurate manner. These approaches also accommodate multi-speed residual learning and multi-scale pyramidal learning. Furthermore, channel-wise filters followed by pointwise convolutions enable in-depth learning to overcome the limits of shallow networks. This solution is scalable to whole body PET-CTs or PET-MRIs, and allows for the evaluation of the clinical efficacy of a treatment, assess TMTV in multiple types of cancers, rapidly assess whole body FDG-PET tumor burden, predict progression-free survival (PFS), stage subjects for therapy as well as selecting subjects for clinical trials, and automated end-of-treatment response assessment (e.g., Lugano).

II. Definitions

As used herein, when an action is "based on" something, this means the action is based at least in part on at least a part of the something.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

III. Techniques for Automated Tumor Segmentation

Image segmentation is a procedure to separate images into portions showing resemblance in different features like shape, size, color, etc. Segmentation of tumors allows visualization of the size and position of a tumor within a region of the body (e.g., the brain or lung), and may also provide a basis for analysis of tracer uptake in PET or single-photon emission computerized tomography (SPECT) images. The gold standard of tumor segmentation has long been manual segmentation, which is time-consuming and labor-intensive, and thus unsuitable for large studies. Considerable research has been done to attempt to fully or partially automate the process of tumor segmentation. For example, image segmentation techniques such as thresholding, region growing, fuzzy clustering, use of the watershed algorithm, etc., have been used for separating abnormal tissues (e.g., tumor masses) from normal tissues, such as white matter (WM), gray matter (GM), and cerebrospinal fluid (CSF) of the brain. Nonetheless, the process of segmentation is still challenging due to the diversity of shape, location, and size of the tumors.

Multimodal imaging techniques (such as PET/CT, PET/magnetic resonance imaging (MRI), and SPECT/CT) that combine the information from many imaging techniques can help improve the accuracy of tumor segmentation. Combined with PET, additional imaging modalities may provide information regarding metabolic or biochemical activity within the subject, physiological processes, and other detailed information about the images.

Described herein is an end-to-end method incorporating a model that uses two-dimensional and three-dimensional convolutional neural networks (CNNs) to segment tumors and extract metabolic information about a lesion from PET (or SPECT) and CT (or MRI) images (scans). As used herein, a "scan" is a graphical representation of signal on a single plane through the body of a subject. The developed model is computationally light (e.g., can run on an average desktop computing device and return predictions on-demand such as e.g., within a few minutes) and devised to accommodate the size of whole body scans, extreme imbalance between tumors and healthy tissue and the heterogeneous nature (e.g., variable density and metabolism of organs) of the input images. The model has comparable performance for tumor segmentation to conventional algorithms relying on manual intervention (e.g., manual selection of seeds or manual identification of bounding boxes) such as a thresholding method, an edge based segmentation method, or a region based segmentation method.

Tumor metabolic information obtained by PET, SPECT, PET/CT, PET/MRI, and SPECT/CT may be used to evaluate the clinical efficacy of a treatment. Tumor metabolic information may be used to assess TMTV in multiple types of cancers, examples of which include but are not limited to Lymphoma (e.g., non-Hodgkin's lymphoma (NHL)) and lung cancer subjects. The method may be a tool for radiologists to rapidly assess whole body PET or SPECT tumor burden. The method may also be used to predict progression free survival (PFS). The method may also be used to stage subjects for therapy as well as selecting subjects for clinical trials. The output of the model can further be used to perform automated end-of-treatment response assessment (e.g., Lugano).

III.A. Example Computing Environment

FIG. 1 illustrates an example computing environment 100 (i.e., a data processing system) for tumor segmentation using deep convolutional neural networks according to various embodiments. The computing environment 100 can include a deep convolutional neural network (CNN) system 105 to train and execute two-dimensional CNN models, three-dimensional CNN models, or a combination thereof. More specifically, the CNN system 105 can include classifier subsystems 110a-n that can train their respective CNN models. In some embodiments, each CNN model corresponding to the classifier subsystems 110a-n is separately trained based on one or more PET scans, CT scans, MRI scans, or any combinations thereof within a set of input image elements 115a-n. In some instances, the PET scans, CT scans, or MRI scans of the set of input image elements 115a-n may be divided into one or more parts (e.g., slices of the body: transverse scans, coronal scans, and sagittal scans and/or anatomical portions or regions: head-neck, chest and abdomen-pelvis) by an image detector such that each of the classifier subsystems 110a-n may process a respective part of the PET scans, SPECT scans, CT scans, or MRI scans for training and deployment.

In some embodiments, each of the input image elements 115a-n may include one or more digital images depicting a portion or region of a body or a whole body (e.g., a whole body scan). Each of the input image elements 115a-n can correspond to a single subject at one or more time points (e.g., baseline or pre-treatment, during treatment, post treatment, or the like) on which underlying image data corresponding to the digital images was obtained. The underlying image data can include one or more PET scans, SPECT scans, CT scans, MRI scans, or any combinations thereof. Thus, in some instances, a single input image element 115a-n can include images corresponding to multiple PET scans, SPECT scans, CT scans, MRI scans, or any combinations thereof, each of which depict different (e.g., overlapping or non-overlapping) portions or regions of a body or a slice of a whole body. In some embodiments, multiple images corresponding to multiple PET scans, SPECT scans, CT scans, MRI scans, or any combinations thereof associated with different portions or regions of a body or a slice of a whole body are stitched together to form a montage of images in order to capture several portions or regions of the whole body. Thus, in some instances, a single input image element 115a-n can include a single stitched image.

Portions or regions of the body represented in a single input image element 115a-n can include one or more central regions of the body (including the head-neck, chest and abdomen-pelvis) and optionally one or more peripheral regions of the body (e.g., for example the legs, feet, arms, or hands). Additionally, virtual slices, fields, planes, or projections of the body can be represented in a single input image element 115a-n. For example, with respect to PET-CT imaging techniques, sequential images from both devices (the PET scanner and the CT scanner) may be obtained in a same session and combined into a single or multiple superposed (co-registered) images. Thus, the functional imaging obtained by the PET scanner, which depicts the spatial distribution of metabolic or biochemical activity in the body can be more precisely aligned or correlated with anatomic imaging obtained by the CT scanner. In some embodiments, a single input image element 115a-n includes the PET scans and CT or MRI scans. With regards to the above, it is also understood that the examples and embodiments regarding PET scans and CT scans are described herein for illustrative purposes only and that other imaging methods and alternatives thereof will be suggested to persons skilled in the art. For example, a PET scan or CT scan with different tracers or angle configurations may capture different structures or regions of the body, and one or more of these types of imaging techniques may be combined with other imaging techniques such as SPECT and MRI for a deeper understanding of the pathology and/or anatomy of the body.

The input image elements 115a-n can include one or more training input image elements 115a-d, validation input image elements 115e-g, and unlabeled input image elements 115h-n. It will be appreciated that input image elements corresponding to the training, validation and unlabeled groups need not be accessed at a same time. For example, initial training and validation input image elements may first be accessed and used to train a model, and unlabeled input image elements may be subsequently accessed or received (e.g., at a single or multiple subsequent times). Further, each of input image elements 115a-g may be accessed and used for training or validation depending on the particular instance of a model training process (such as e.g. when performing k-fold cross validation).

In some instances, the CNN models can be trained using supervised training, and each of the training input image elements 115a-d and the validation input image elements 115e-g can be associated with one or more labels that identify a "correct" interpretation of a presence and/or severity of a tumor. Labels may alternatively or additionally be used to classify a corresponding input image element, or pixel or voxel therein, with regards to a presence and/or severity of a tumor at a time point corresponding to when the underlying scan(s) was/were taken or a subsequent time point (e.g., that is a predefined duration following a time when the scan(s) was/were taken). In some instances, CNN models can be trained using unsupervised training, and each of the training input image elements 115a-d and the validation input image elements 115e-g need not be associated with one or more labels. Each of the unlabeled image elements 115h-n need not be associated with one or more labels.

The CNN models can be trained using the training input image elements 115a-d (and the validation input image elements 115e-h to monitor training progress), a loss function and/or a gradient descent method. In instances for which an input image data element corresponds to multiple underlying scans, each corresponding to a different portion, field, planes, or slice of a body, each of a set of the CNN models can be trained to process image data corresponding to a specific portion, field, plane, or slice of a body.

In some embodiments, the classifier subsystems 110a-n include a feature extractor 120, a parameter data store 125, a classifier 130, and a trainer 135, which are collectively used to train the CNN models (e.g., learning parameters of the CNN models during supervised or unsupervised training) using training data (e.g., the training input image elements 115a-d). In some embodiments, the classifier subsystem 110a-n accesses training data from the training input image elements 115a-d at the input layers. The feature extractor 120 may pre-process the training data to extract relevant features (e.g., edges) detected at particular parts of the training input image elements 115a-d. The classifier 130 can receive the extracted features and transform the features, in accordance with weights associated with a set of hidden layers in one or more CNN models, into one or more output metrics that segment one or more tumors and optionally indicate the clinical efficacy of a treatment, assess TMTV, assess whole body PET tumor burden, predict PFS, stage subjects for therapy as well as selecting subjects for clinical trials, automate end-of-treatment response assessment (e.g., Lugano), or a combination thereof. The trainer 135 may use training data corresponding to the training input image elements 115a-d to train the feature extractor 120 and/or the classifier 130 by facilitating the learning of one or more parameters. For example, the trainer 135 can use a backpropagation technique to facilitate learning of weights associated with a set of hidden layers of the CNN model used by the classifier 130. The backpropagation may use, for example, a stochastic gradient descend (SGD) algorithm to cumulatively update the parameters of the hidden layers. Learned parameters may include, for instance, weights, biases, linear regression, and/or other hidden layer-related parameters, which can be stored in the parameter data store 125.

An ensemble of trained CNN models ("CNN ensemble," e.g., multiple trained CNN models individually trained to identify different features, objects or metrics in the input images, which are then combined as an image mask and/or output metric) can be deployed to process unlabeled input image elements 115h-n to segment one or more tumors and optionally predict one or more output metrics that indicate the clinical efficacy of a treatment, assess TMTV, assess whole body FDG-PET tumor burden, predict PFS, stage subjects for therapy as well as selecting subjects for clinical trials, automate end-of-treatment response assessment (e.g., Lugano), or a combination thereof. More specifically, a trained version of the feature extractor 120 may generate a feature representation of an unlabeled input image element, which can then be processed by a trained version of the classifier 130. In some embodiments, image features can be extracted from the unlabeled input image elements 115h-n based on one or more convolutional blocks, convolutional layers, residual blocks, or pyramidal layers that leverage dilation of the CNN models in the classifier subsystems 110a-n. The features can be organized in a feature representation, such as a feature vector of the image. The CNN models can be trained to learn the feature types based on classification and subsequent adjustment of parameters in the hidden layers, including a fully connected layer of the CNN models. In some embodiments, the image features extracted by the convolutional blocks, convolutional layers, residual blocks, or pyramidal layers include feature maps that are matrix of values that represent one or more portions of the scans at which one or more image processing operations have been performed (e.g., edge detection, sharpen image resolution). These feature maps may be flattened for processing by a fully connected layer of the CNN models, which outputs a tumor mask or one or more metrics corresponding to a present or future prediction pertaining to a tumor.

For example, an input image element can be fed to an input layer of a CNN model. The input layer can include nodes that correspond with specific pixels or voxels. A first hidden layer can include a set of hidden nodes, each of which is connected to multiple input-layer nodes. Nodes in subsequent hidden layers can similarly be configured to receive information corresponding to multiple pixels or voxels. Thus, hidden layers can be configured to learn to detect features extending across multiple pixels or voxels.

Each of one or more hidden layers can include a convolutional block, convolutional layer, residual block, or pyramidal layer. The CNN model can further include one or more fully connected layers (e.g., a softmax layer).

At least part of the training input image elements 115a-d, the validation input image elements 115e-g and/or the unlabeled input image elements 115h-n may include or may have been derived from data collected using and received from one or more imaging systems 160. The imaging system 160 can include a system configured to collect image data (e.g., PET scans, CT scans, MRI scans, or any combinations thereof). The imaging system 160 may include a PET scanner and optionally a CT scanner and/or an MRI scanner. The PET scanner may be configured to detect photons (subatomic particles) emitted by a radionuclide in the organ or tissue being examined. The radionuclides used in PET scans may be made by attaching a radioactive atom to a chemical substance that is used naturally by the particular organ or tissue during its metabolic process. For example, in PET scans of the brain, a radioactive atom (e.g., radioactive fluorine such as $^{18}F$) may be attached to glucose (blood sugar) to create FDG, because the brain uses glucose for its metabolism. Other radioactive tracers and/or substances may be used for image scanning, depending on the purpose of the scan. For example, if blood flow and perfusion of an organ or tissue is of interest, the radionuclide may be a type of radioactive oxygen, carbon, nitrogen, or gallium; if infectious diseases are of interest, a radioactive atom may be attached to sorbitol (e.g., fluorodeoxysorbitol (FDS)); and if oncology is of interest, a radioactive atom may be attached to misonidazole (e.g., fluoromisonidazole (FMISO)). The raw data collected by the PET scanner are a list of 'coincidence events' representing near-simultaneous detection (typically, within a window of 6 to 12 nanoseconds of each other) of annihilation photons by a pair of detectors. Each coincidence event represents a line in space connecting the two detectors along which the positron emission occurred (i.e., the line of response (LOR)). Coincidence events can be grouped into projection images, called sinograms. The sinograms are used in computer analysis to reconstruct two-dimensional images and three-dimensional images of metabolic processes in organ or tissue being examined. The two-dimensional PET images and/or the three-dimensional PET images may be included within the set of input image elements 115a-n. However, the sinograms collected in PET scanning is much poorer quality with respect to anatomical structures than CT or MRI scans, which can result in noisier images.

To overcome the deficiencies of PET scanning with respect to anatomical structures, PET scans are increasingly read alongside CT or MRI scans, with the combination (called "co-registration") giving both detailed anatomic and metabolic information (i.e., what the structure is, and what it is doing biochemically). Because PET imaging is most useful in combination with separate anatomical imaging, such as CT or MRI, PET scanners are available with integrated high-end multi-detector-row CT or MRI scanners. The two scans can be performed in immediate sequence during the same session, with a particular subject not changing position between the two types of scans. This allows the two sets of images to be more precisely registered, so that areas of abnormality on the PET imaging can be more perfectly correlated with anatomy on the CT or MRI images.

The CT scanner may be configured to aim a motorized x-ray source, which generates a narrow beam of x-rays, at a particular subject, and quickly rotate the x-ray source and beam of x-rays around the body. Digital x-ray detectors, which are located directly opposite the x-ray source, detect the x-rays leaving the body and generate signals that are processed by the scanner's computer to generate two-dimensional cross-sectional images—or "slices"—of the body. These slices are also known as tomographic images and contain more detailed information than conventional x-rays. The thickness of the tissue represented in each image slice can vary depending on the CT scanner used, but usually ranges from 1-10 millimeters. When a full slice is completed, the two-dimensional image is stored and a motorized bed holding the subject is moved forward incrementally into a gantry. The x-ray scanning process is then repeated multiple times to generate a series of two-dimensional images taken around an axis of rotation. Once the series of two-dimensional images are collected by the scanner's computer, the two-dimensional images can be digitally "stacked" together by computer analysis to reconstruct a three-dimensional image of the subject. The two-dimensional images and/or the reconstructed three-dimensional images allow for easier identification and location of basic structures as well as possible tumors or abnormalities. When CT scanning is used for imaging a particular subject as part of a PET-CT scanner or as a separate CT scanner, the two sets of two-dimensional images and/or the reconstructed three-dimensional images (or the registered set of two-dimensional images and/or the reconstructed three-dimensional images) from the PET and CT scanning are included within the set of input image elements 115a-n for training the CNN models.

The MRI scanner may be configured to use a strong magnetic field and radio waves to generate three dimensional detailed anatomical images. More specifically, the magnetic field forces protons in the tissue or body to align with that magnetic field. When a radiofrequency current is then pulsed through the tissue or body, the protons are stimulated, and spin out of equilibrium, straining against the pull of the magnetic field. When the radiofrequency field is turned off, the MRI sensors are able to detect the energy released as the protons realign with the magnetic field. The time it takes for the protons to realign with the magnetic field, as well as the amount of energy released, changes depending on the environment and the chemical nature of the molecules. A computing device is able to tell the difference between various types of tissues based on these magnetic properties and generate a series of two-dimensional images. Once the series of two-dimensional images are collected by the scanner's computer, the two-dimensional images can be digitally "stacked" together by computer analysis to reconstruct a three-dimensional image of the subject. The two-dimensional images and/or the reconstructed three-dimensional images allow for easier identification and location of basic structures as well as possible tumors or abnormalities. When MRI scanning is used for imaging a particular subject as part of a PET-MRI scanner or as a separate MRI scanner, the two sets of two-dimensional images and/or the reconstructed three-dimensional images (or the registered set of two-dimensional images and/or the reconstructed three-dimensional images) from the PET and CT scanning are included within the set of input image elements 115a-n for training the CNN models.

In some instances, labels associated with the training input image elements 115a-d and/or validation input image elements 115e-g may have been received or may be derived from data received from one or more provider systems 170, each of which may be associated with (for example) a physician, nurse, hospital, pharmacist, etc. associated with a particular subject. The received data may include (for example) one or more medical records corresponding to the particular subject. The medical records may indicate (for example) a professional's diagnosis or characterization that indicates, with respect to a time period corresponding to a time at which one or more input image elements associated with the subject were collected or a subsequent defined time period, whether the subject had a tumor and/or a stage of progression of the subject's tumor (e.g., along a standard scale and/or by identifying a metric, such as TMTV). The received data may further include the pixels or voxels of the locations of tumors within the one or more input image elements associated with the subject. Thus, the medical records may include or may be used to identify, with respect to each training/validation input image element, one or more labels. The medical records may further indicate each of one or more treatments (e.g., medications) that the subject had been taking and time periods during which the subject was receiving the treatment(s). In some instances, images or scans that are input to one or more classifier subsystems are received from the provider system 170. For example, the provider system 170 may receive images or scans from the imaging system 160 and may then transmit the images or scans (e.g., along with a subject identifier and one or more labels) to the CNN system 105.

In some embodiments, data received at or collected at one or more of the imaging systems 160 may be aggregated with data received at or collected at one or more of the provider systems 170. For example, the CNN system 105 may identify corresponding or identical identifiers of a subject and/or time period so as to associate image data received from the imaging system 160 with label data received from the provider system 170. The CNN system 105 may further use metadata or automated image analysis to process data to determine to which classifier subsystem particular data components are to be fed. For example, image data received from the imaging system 160 may correspond to the whole body or multiple regions of the body. Metadata, automated alignments and/or image processing may indicate, for each image, to which region the image corresponds. For example, automated alignments and/or image processing may include detecting whether an image has image properties corresponding to a blood-vessel and/or shape that is associated with a particular organ such as the lung or liver. Label-related data received from the provider system 170 may be region-specific or subject-specific. When label-related data is region specific, metadata or automated analysis (e.g., using natural language processing or text analysis) can be used to identify to which region particular label-related data corresponds. When label-related data is subject-specific, identical label data (for a given subject) may be fed to each classifier subsystem during training.

In some embodiments, the computing environment 100 can further include a user device 180, which can be associated with a user that is requesting and/or coordinating performance of the CNN system 105 to analyze input images associated with a subject for training, testing, validation, or use case purposes. The user may be a physician, investigator (e.g., associated with a clinical trial), subject, medical professional, etc. Thus, it will be appreciated that, in some instances, the provider system 170 may include and/or serve as the user device 180. The performance of the CNN system 105 to analyze input images may be associated with a particular subject (e.g., person), who may (but need not) be different than the user. The performance may be implemented by the user device 180 communicating a request for performance to the CNN system. The request may include and/or be accompanied with information about the particular subject (e.g., a name or other identifier of the subject, such as a de-identified subject identifier). The request may include an identifier of one or more other systems from which to collect data, such as input image data that corresponds to the subject. In some instances, the communication from the user device 180 includes an identifier of each of a set of particular subjects, in correspondence with a request for performance of the CNN system 105 to analyze input images associated with each subject represented in the set of particular subjects.

Upon receiving the request, the CNN system 105 can send a request (e.g., that includes an identifier of the subject) for unlabeled input image elements to the one or more corresponding imaging systems 160 and/or provider systems 170. The trained CNN ensemble can then process the unlabeled input image elements to segment one or more tumor(s) and generate metrics such as TMTV (a quantitative tumor burden parameter) associated with PFS. A result for each identified subject may include or may be based on the tumor segmenting and/or one or more output metrics from one or more CNN models of the trained CNN ensemble deployed by the classifier subsystems 110a-n. For example, the tumor segmentation and/or metrics can include or may be based on output generated by the fully connected layer of one or more CNNs. In some instances, such outputs may be further processed using (for example) a softmax function. Further, the outputs and/or further processed outputs may then be aggregated using an aggregation technique (e.g., random forest aggregation) to generate one or more subject-specific metrics. One or more results (e.g., that include plane-specific outputs and/or one or more subject-specific outputs and/or processed versions thereof) may be transmitted to and/or availed to the user device 180. In some instances, some or all of the communications between the CNN system 105 and the user device 180 occurs via a website. It will be appreciated that the CNN system 105 may gate access to results, data and/or processing resources based on an authorization analysis.

While not explicitly shown, it will be appreciated that the computing environment 100 may further include a developer device associated with a developer. Communications from a developer device may indicate what types of input image elements are to be used for each CNN model in the CNN system 105, a number and type of neural networks to be used, and hyperparameters of each neural network, for example, learning rate and number of hidden layers, and how data requests are to be formatted and/or which training data is to be used (e.g., and how to gain access to the training data).

III.B. Model Overview

Figure 2A:
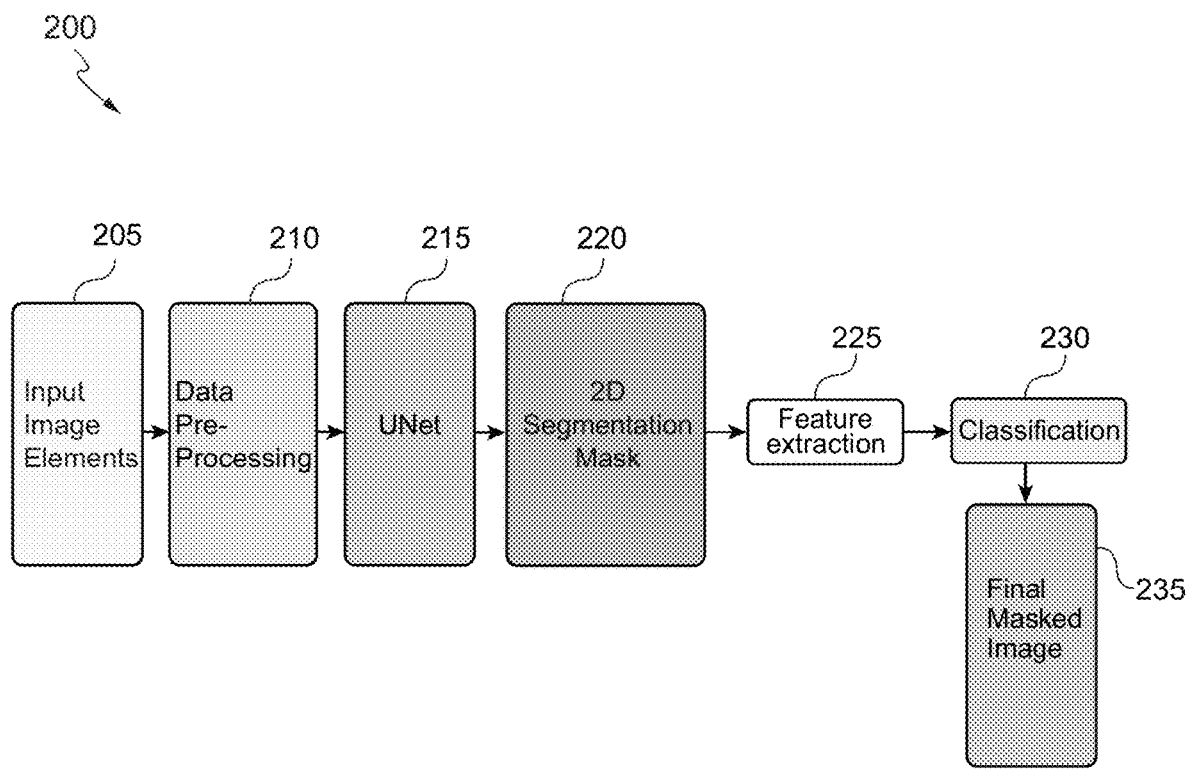
FIG. 2A shows an exemplary schematic diagram representative of a convolutional neural network (CNN) architecture according to various embodiments.

FIG. 2A illustrates an exemplary schematic diagram 200 representative of a CNN architecture (e.g., a portion of the CNN system 105 described with respect to FIG. 1) for tumor segmentation in accordance with various embodiments. In some embodiments, input images elements 205 are obtained from one or more image sources (e.g., the imaging systems 160 or provider systems 170, as described with respect to FIG. 1). The input image elements 205 include one or more digital images depicting a portion or region of a body or a whole body (e.g., a whole body scan) for a subject (e.g., a patient) obtained at one or more time points (e.g., baseline or pre-treatment, during treatment, post treatment, or the like). The underlying image data can include two-dimensional and/or reconstructed three-dimensional PET images, CT images, MRI images, or any combination thereof obtained. Thus, in some instances, a single input image element 205 can include images corresponding to multiple PET scans, SPECT scans, CT scans, MRI scans, or any combinations thereof, each of which depict different (e.g., overlapping or non-overlapping) portions or regions of a body or a slice of a whole body. In some embodiments, multiple images corresponding to multiple PET scans, SPECT scans, CT scans, MRI scans, or any combinations thereof associated with different portions or regions of a body or a slice of a whole body are stitched together to form a montage of images in order to capture several portions or regions of the whole body. Thus, in some instances, a single input image element 205 can include a single stitched image.

The input image elements 205 are structured as one or more arrays or matrices of pixel or voxel values. A given pixel or voxel position is associated with (for example) a general intensity value and/or an intensity value as it pertains to each of one or more gray levels and/or colors (e.g., RGB values). For example, each image of the input image elements 205 may be structure as a three-dimensional matrix where the size of the first two dimensions corresponds to the width and height of the each image in pixels. The size of the third dimension may be based on the color channels associated with each image, e.g., the third dimension could be 3 corresponding to the 3 channels of a color image: red, green, and blue).

The input image elements 205 are provided as input to pre-processing subsystem 210 of the CNN architecture, which generates standardized image data across the input image elements 205. Pre-processing may include selecting subsets of images or input image elements 205 for slices (e.g., coronal, axial, and sagittal slices) or regions of the body and performing geometric re-sampling (e.g., interpolating) of the subsets of images input image elements 205 in terms of uniform pixel spacing (e.g., 1.0 mm) and slice thickness (e.g., 2 mm). Image intensity values of all images may be truncated to a specified range (e.g., −1000 to 3000 Hounsfield Unit) to remove noise and possible artifacts. The standardization of the spacing, slice thickness, and units ensures that each pixel has a consistent area and each voxel has a consistent volume across all images of the input image elements 205. The output from the pre-processing subsystem 210 is subsets of standardized images for slices (e.g., coronal, axial, and sagittal slices) or regions of the body.

Tumor segmentation may be performed using a semantic segmentation model architecture comprising one or more trained CNN models 215 (e.g., a CNN model associated with classifier subsystem 110a as described with respect to FIG. 1). In semantic segmentation, the CNN models 215 identify the location and shapes of different objects (e.g., tumor tissue and normal tissue) in an image by classifying each pixel with desired labels. For example, tumor tissue are labeled tumor and are colored red, normal tissue are labeled normal and are colored green, and background pixels are labeled background and are colored black. The subsets of standardized images from the pre-processing subsystem 210 are used as input into the one or more trained CNN models 215. In some instances, a single trained CNN model is used for processing all of the subsets of standardized images. In other instances, a set of trained CNN models (e.g., a CNN ensemble) is used where each CNN model is trained for processing images originating from different slices (coronal, axial, and sagittal slices) or regions of the body. For example, a subset of standardized images from the coronal slices may be used as input for a first CNN of the set of trained CNN models and a subset of standardized images from the sagittal slices may be used as input for a second CNN of the set of trained CNN models.

The trained CNN models 215 are two-dimensional segmentation models such as U-Nets configured to initially obtain a lower-dimensional representation of the standardized images, and then upsample that low-dimensional representation to generate a two-dimensional segmentation mask 220 for each image. As described in detail herein, a U-Net comprises a contracting path supplemented with an expansive path. The contracting path is divided in different stages that operate at different resolutions. Each stage comprises one to three convolutional layers, which generate the low-dimensional representation. The expansive path upsamples the low-dimensional representation to generate the two-dimensional segmentation mask 220. The pooling operations of successive layers in the expansive path are replaced with upsampling operators, and these successive layers increase the resolution of the two-dimensional segmentation mask 220. The two-dimensional segmentation mask 220 is a high resolution (as used herein, "high resolution" refers to an image having more pixels or voxels than the lower-dimensional representation processed by the contracting path of a U-Net of V-Net) masked image in which all the pixels are classified (e.g., some of the pixel intensity values are zero and others are non-zero). The non-zero pixels represent the locations of tissue present in an image or portion of an image (e.g., a PET-CT or PET-MRI scan) from the subset of standardized images. For example, wherever a pixel is classified as background, then the intensity of the pixel within the masked image will be set to a background value (e.g., zero). Wherever a pixel is classified as tumor tissue, then the intensity of the pixel within the masked image will be set to a tumor value (e.g., a non-zero). The two-dimensional segmentation mask 220 shows the non-zero pixels representative of the location of tumor tissue identified within a PET scan relative to anatomical structures within the underlying CT or MRI scan (see, e.g., the two-dimensional segmentation mask 220 in FIG. 2C). The non-zero pixels representative of the location of tumor tissue are grouped and labeled as one or more instances of segmentation indicative of various instances of tumor tissue within the image from the input image elements 205.

The two-dimensional segmentation mask 220 is input into a feature extractor 225 (e.g., the feature extractor 120 as described with respect to FIG. 1) and the feature extractor 225 extracts relevant features from the two-dimensional segmentation mask 220. Feature extraction is a process of dimensionality reduction by which an initial set of data (e.g., the two-dimensional segmentation mask 220) is reduced to more manageable relevant features for further processing. The relevant features may include texture features (e.g., contrast, dissimilarity, cluster shade, cluster prominence, etc.), shape features (e.g., area, eccentricity, extent, etc.), prognostic signatures (e.g., linking tumor feature to likely outcome or course of a disease), or the like, which can help in further classification of pixels within the two-dimensional segmentation mask 220. Texture features may be extracted using a Gray level co-occurrence matrix or similar techniques. Shape features may be extracted using region property functions or similar techniques. Prognostic signatures may be extracted using k-means clustering or similar techniques.

The relevant features extracted from the feature extractor 225 and the two-dimensional segmentation mask(s) 220 are input into a classifier 230 (e.g., the classifier 130 as described with respect to FIG. 1) and the classifier 230 transforms the relevant features and combines the two-dimensional segmentation mask(s) 220 into a final masked image 235. The classifier 230 may use the relevant features to refine the classification of pixels in the two-dimensional segmentation mask(s) 220 and combined (e.g., using an average or other statistical function(s)) the two-dimensional segmentation mask(s) 220 to generate a final masked image 235. The final masked image 235 is a high resolution masked image in which all the pixels are classified and segmentation outlines, borders, transparent patches, or the like are overlaid around and/or over specified segments (e.g., tumor tissue) based on the classified pixels (see, e.g., the final masked image 235 in FIG. 2C). In some instances, the classifier 230 further transforms data obtained from the final masked image 235 into one or more output metrics that indicate the clinical efficacy of a treatment, assess TMTV, assess whole body PET tumor burden, predict PFS, stage subjects for therapy as well as select subjects for clinical trials, automate end-of-treatment response assessment (e.g., Lugano), or a combination thereof. In one specific example, classification (e.g., using the classifier) can be performed on the prognostic signature to obtain an output in a desired form depending on the design of the classifier. For example, the classifier 235 can be trained against labeled training data to extract a TMTV, predict PFS, stage subjects for therapy, and/or select subjects for clinical trials.

Figure 2B:
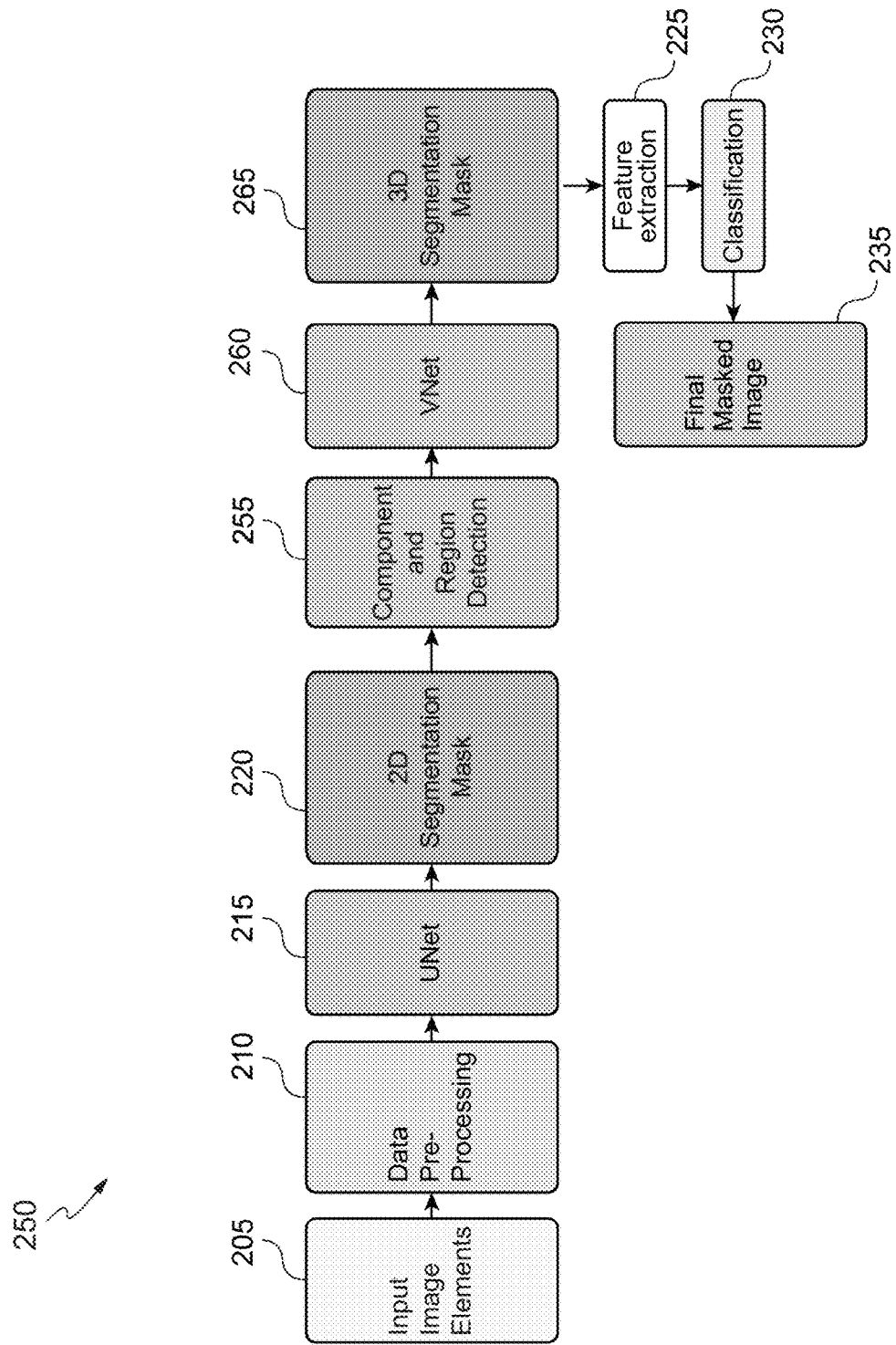
FIG. 2B shows an exemplary schematic diagram representative of a CNN architecture according to various embodiments.

FIG. 2B illustrates an exemplary schematic diagram 250 representative of an alternative CNN architecture (e.g., a portion of the CNN system 105 described with respect to FIG. 1) for tumor segmentation in accordance with various embodiments. The CNN architecture shown in FIG. 2B is similar to the CNN architecture shown in FIG. 2A but for it incorporates in a component detection model 255, and three-dimensional segmentation models 260. Accordingly, like components, operations, and terms will not be repeated where possible in the description of the exemplary schematic diagram 250 for purposes of brevity. In some embodiments, input images elements 205 are obtained from one or more image sources (e.g., the imaging systems 160 or provider systems 170, as described with respect to FIG. 1). The input image elements 205 include one or more digital images depicting a portion or region of a body or a whole body (e.g., a whole body scan) for a subject (e.g., a patient) obtained at one or more time points (e.g., baseline or pre-treatment, during treatment, post treatment, or the like). The underlying image data can include two-dimensional and/or reconstructed three-dimensional PET images, CT images, MRI images, or any combination thereof obtained. The input image elements 205 are provided as input to pre-processing subsystem 210 of the CNN architecture, which generates standardized image data across the input image elements 205. The output from the pre-processing subsystem 210 is subsets of standardized images for slices (e.g., coronal, axial, and sagittal slices) or regions of the body.

Tumor segmentation may be performed using a semantic segmentation model architecture comprising one or more trained CNN models 215 (e.g., a CNN model associated with classifier subsystem 110a as described with respect to FIG. 1), a component detection model 255, and one or more trained CNN models 260 (e.g., a CNN model associated with classifier subsystem 110b as described with respect to FIG. 1). The subsets of standardized images from the pre-processing subsystem 210 are used as input into the one or more trained CNN models 215. The trained CNN models 215 are two-dimensional segmentation models such as U-Nets configured to initially obtain a lower-dimensional representation of the standardized images, and then upsample that low-dimensional representation to generate a two-dimensional segmentation mask 220.

The standardized images from the pre-processing subsystem 210 (specifically the standardized images used to generate the two-dimensional segmentation mask 220) are used as input into a component detection model 255. The component detection model 255 automatically assesses the location of components of the region or body captured in the standardized images as reference points, and uses the reference points to split the region or body into the multiple anatomical regions. Thereafter, the component detection model may generate location labels for the multiple anatomical regions and incorporate the location labels within the two-dimensional segmentation mask. For example, a segment superior of a reference point for the lungs and distal to the reference point for the lungs may be labeled as head-neck, a segment superior of the reference point for the liver and proximal to a reference point for the lungs may be labeled as chest, and a segment of a reference point for the lungs and proximal the reference point for the liver may be labeled as abdomen-pelvis.

Patches of image data corresponding to segments within the two-dimensional segmentation mask 220 are used as input into the one or more trained CNN models 260. Each segment is a pixel-wise or voxel-wise mask for a classified object in the underlying image. The patches of image data for each segment include volumes of image data having a fixed size voxel expressed as a(width)×b(height)×c(depth) that is derived from both the pixel size and slice thickness of the patches. The patches may be defined by the border of the segment (i.e., the pixels or voxels classified as being part of the segment such as tumor tissue), a bounding box with coordinates generated to encompass the segment, or the border or the bounding box plus a buffer zone of predetermined number of pixels or voxels to ensure the entire segment is included within the patch of image data. System processing or the CNN models 260 use the labels provided for the multiple anatomical regions as markers to select segments within the two-dimensional segmentation mask 220 for input into select CNN models 260 (e.g., a CNN model specifically trained on scans from a specified anatomical region such as the head-neck region). For example, a subset of patches corresponding to a subset of segments identified by location labels for the head-neck may be used as input for a first CNN trained on head-neck scans, a subset of patches corresponding to a subset of segments identified by location labels for the chest may be used as input for a second CNN trained on chest scans, and a subset of patches corresponding to a subset of segments identified by location labels for the abdomen-pelvis may be used as input for a third CNN trained on abdomen-pelvis scans.

The trained CNN models 260 are three-dimensional segmentation models such as V-Nets configured to initially obtain lower resolution feature maps of each patch of image data corresponding to a segment, and then upsample the lower resolution feature maps to generate a three-dimensional segmentation mask 265 for each patch of image data. As described in detail herein, a V-Net comprises a contracting path supplemented with an expansive path. The contracting path is divided in different stages that operate at different resolutions. Each stage comprises one or more convolutional layers. At each stage, a residual function is learnt. The input of each stage is used in the convolutional layers and processed through the non-linearities and added to the output of the last convolutional layer of that stage in order to enable learning a residual function. This architecture ensures convergence compared with a non-residual learning network such as U-Net. The convolutions performed in each stage use volumetric kernels having size of n×n×n voxels. A voxel (volume elements or volumetric pixels) represents a value, sample, or data point on a regular grid in three-dimensional space.

The expansive path extracts features and expands the spatial support of the lower resolution feature maps in order to gather and assemble the necessary information to output the three-dimensional segmentation mask 265 for each patch of image data. At each stage, a deconvolution operation is employed in order increase the size of the inputs followed by one to three convolutional layers, involving half the number of n×n×n kernels employed in the previous layer. A residual function is learnt, similar to the contracting part of the network. Each three-dimensional segmentation mask 265 is a high resolution masked image in which all the voxels are classified (e.g., some of the voxel intensity values are zero and others are non-zero). The non-zero voxels represent the locations of tissue present in an image or portion of an image (e.g., a PET-CT or PET-MRI scan) from the subset of standardized images. For example, wherever a voxel is classified as background, then the intensity of the voxel within the masked image will be set to a background value (e.g., zero). Wherever a voxel is classified as tumor tissue, then the intensity of the voxel within the masked image will be set to a tumor value (e.g., a non-zero). The three-dimensional segmentation mask 265 shows the non-zero voxels representative of the location of tumor tissue identified within a PET scan relative to anatomical structures within the underlying CT or MRI scan. The non-zero voxels representative of the location of tumor tissue are grouped and labeled as one or more segments indicative of various instances of tumor tissue within the patches of image data.

The two-dimensional segmentation mask 220 and the three-dimensional segmentation mask 265 for each patch of image data are input into a feature extractor 225 (e.g., the feature extractor 120 as described with respect to FIG. 1) and the feature extractor 225 extracts relevant features from the two-dimensional segmentation mask 220 and each of the three-dimensional segmentation masks 265. The relevant features extracted, the two-dimensional segmentation mask 220, and the three-dimensional segmentation masks 265 are input into a classifier 230 (e.g., the classifier 130 as described with respect to FIG. 1) and the classifier 230 transforms and combines the relevant features, the two-dimensional segmentation mask 220, and the three-dimensional segmentation masks 265 into a final masked image 235. More specifically, the classifier 230 uses the relevant features to refine the classification of pixels and voxels in the two-dimensional segmentation mask 220 and each of the three-dimensional segmentation masks 265.

Thereafter, the classifier combines (e.g., averages pixel and/or voxel values) the refined two-dimensional segmentation mask 220 and three-dimensional segmentation masks 265 to generate a final masked image 235. The final masked image 235 is a high resolution masked image in which all the pixels and voxels are classified and segmentation outlines, borders, transparent patches, or the like are overlaid around and/or over segments (e.g., tumor tissue) based on the classified pixels and voxels (see, e.g., the final masked image 235 in FIG. 2C). In some instances, the classifier 230 further transforms data obtained from the final masked image 235 into one or more output metrics that indicate the clinical efficacy of a treatment, assess TMTV, assess whole body PET tumor burden, predict PFS, stage subjects for therapy as well as select subjects for clinical trials, automate end-of-treatment response assessment (e.g., Lugano), or a combination thereof. In one specific example, classification (e.g., using the classifier) can be performed on the prognostic signature to obtain an output in a desired form depending on the design of the classifier. For example, the classifier 235 can be trained against labeled training data to extract a TMTV, predict PFS, stage subjects for therapy, and/or select subjects for clinical trials.

Figure 2C:
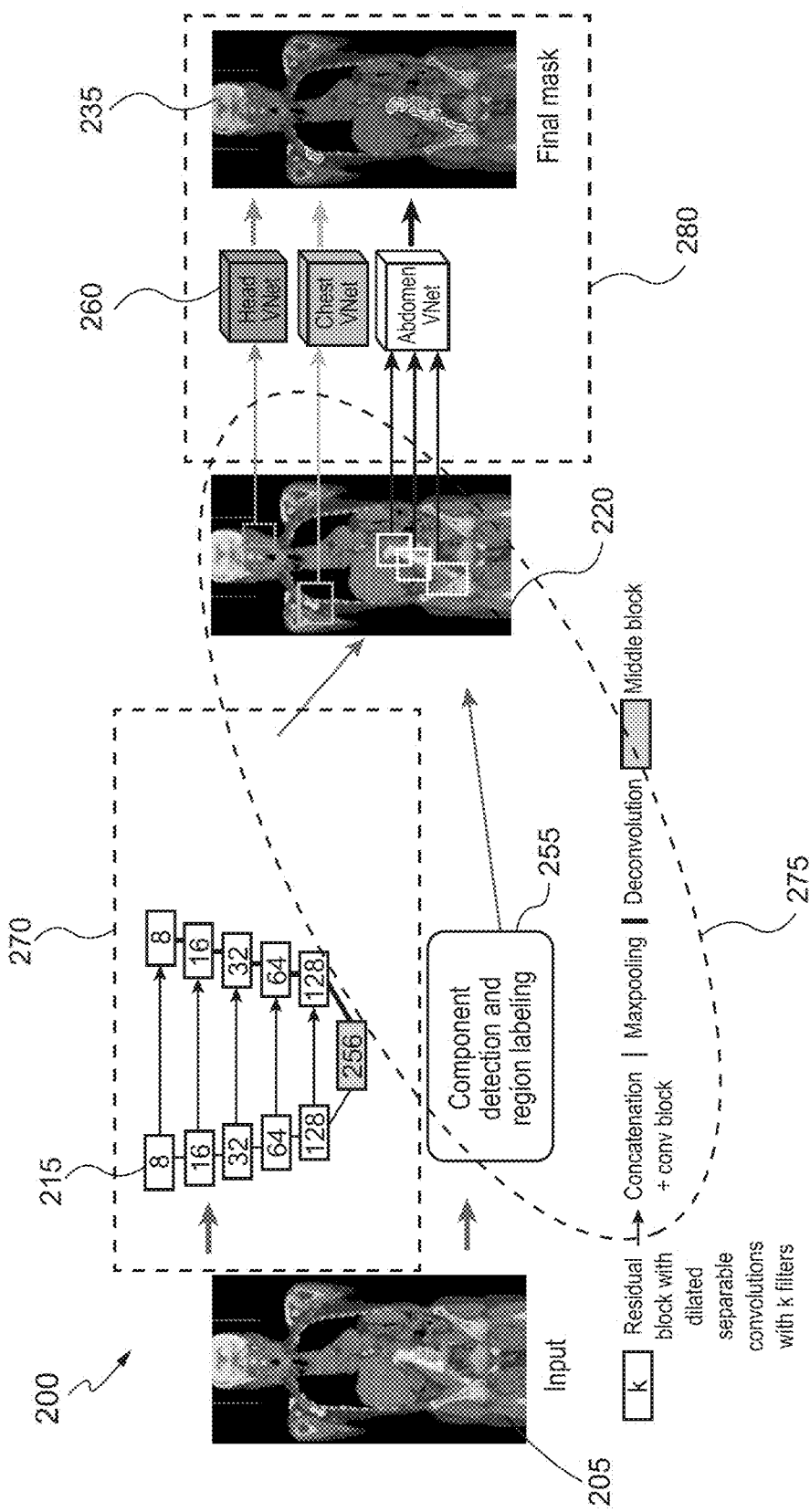
FIG. 2C shows an exemplary detailed schematic diagram representative of a CNN architecture according to various embodiments.

FIG. 2C is another view of the model architecture from FIG. 2B, including the input image elements 205 (standardized by the pre-processing subsystem 210), the two-dimensional segmentation models 215, the component detection model 255, the two-dimensional segmentation mask 220 with regional labels, the three-dimensional segmentation models 265, and the predicted final masked image 235, according to various embodiments. In the model architecture of FIG. 2C, the models 215/255/265 are shown to perform three operations: (i) a two-dimensional segmentation 270 using two-dimensional segmentation models 215 to generate first predictions for tumors within two-dimensional tumor masks—as further explained in III.C herein, (ii) components and region detection 275 to identify anatomical regions within the input image elements 205 (standardized by the pre-processing subsystem 210) and provide location labels for the corresponding anatomical regions within the two-dimensional segmentation mask 220 obtained in step (i)—as further explained in III.D herein, and (iii) a refinement of the first predictions for tumors (from step (i)) in each of the anatomical regions of the two-dimensional segmentation mask 220 (identified in step (ii)) using respective three-dimensional segmentation models 265 that separately perform three-dimensional segmentation 280 for each of the anatomical regions to generate multiple three-dimensional tumor masks, which can be combined into a final masked image 235—as further explained in III.E herein.

III.C. Exemplary U-Net for Two-Dimensional Segmentation

Figure 3:
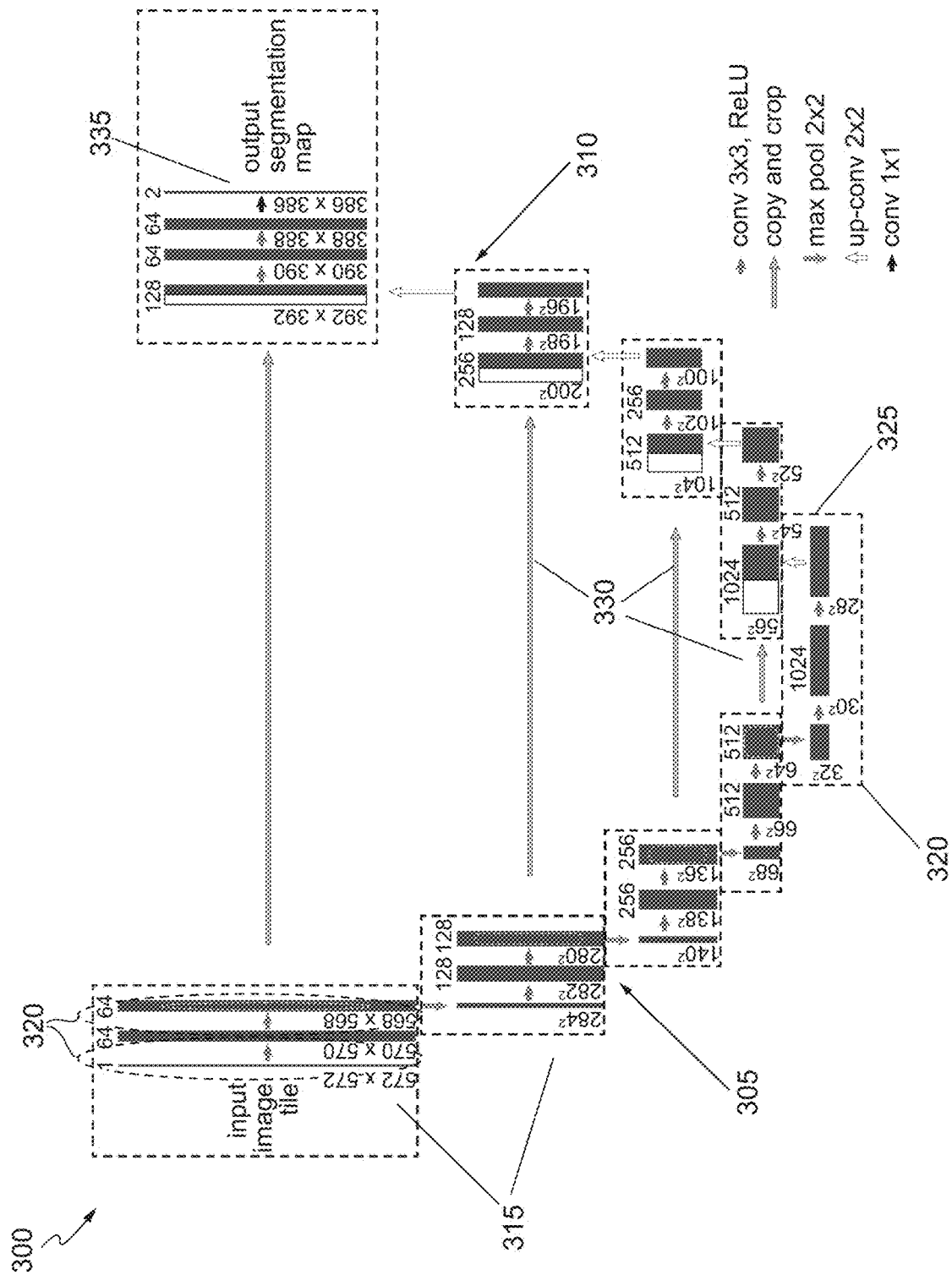
FIG. 3 shows an exemplary U-Net according to various embodiments.

The two-dimensional segmentation extracts features from the input images (e.g., the standardized PET scans, CT scans, MRI, scans, or any combination thereof) individually using a modified U-Net to generate a two-dimensional segmentation mask with high-resolution features. As shown in FIG. 3, a U-Net 300 includes a contracting path 305 and an expansive path 310, which gives it a u-shaped architecture. The contracting path 305 is a CNN network that includes repeated application of convolutions (e.g., 3×3 convolutions (unpadded convolutions)), each followed by a rectified linear unit (ReLU) and a max pooling operation (e.g., a 2×2 max pooling with stride 2) for downsampling. The input for a convolutional operation is a three-dimensional volume (i.e., the input images of size n×n×channels, where n is a number of input features) and a set of 'k' filters (also called as kernels or feature extractors) each one of size (f×f×channels, where f is any number, for example, 3 or 5). The output of a convolutional operation is also a three-dimensional volume (also called as output image or feature map) of size (m×m×k, where M is a number of output features and k is the convolutional kernel size).

Each block 315 of a contraction path 315 includes one or more convolutional layers (denoted by gray horizontal arrows), and the number of feature channels changes, e.g., from 1→64 (e.g., in the first process depending on the starting number of channels), as convolution processes will increase the depth of the input image. The gray arrow pointing down between each block 315 is the max pooling process which halves down the size of the input image. At each downsampling step or pooling operation, the number of feature channels may be doubled. During the contraction, the spatial information of the image data is reduced while feature information is increased. Thus before pooling, the information which was present in, e.g., a 572×572 image, after pooling, (almost) the same information is now present in, e.g., a 284×284 image. Now when the convolution operation is applied again in a subsequent process or layer, the filters in the subsequent process or layer will be able to see larger context, i.e., as the input image progresses deeper into the network, the size of the input image reduces however the receptive field increases (receptive field (context) is the area of the input image that the kernel or filter covers at any given point of time). Once the blocks 315 are performed, two more convolutions are performed in block 320 but with no max pooling. The image after block 320 has been resized to e.g., 28×28×1024 (this size is merely illustrative and the size at the end of process 320 could be different depending on the starting size of the input image—size n×n× channels).

The expansive path 310 is a CNN network that combines the feature and spatial information from the contracting path 305 (upsampling of the feature map from the contracting path 305). As described herein, the output of two-dimensional segmentation is not just a class label or bounding box parameters. Instead, the output (the two-dimensional segmentation mask) is a complete high resolution image in which all the pixels are classified. If a regular convolutional network with pooling layers and dense layers was used, the CNN network would lose the "where" information and only retain the "what" information which is not acceptable for image segmentation. In the instance of image segmentation, both "what" as well as "where" information are need. Thus, there is a need to up sample the image, i.e., convert a low resolution image to a high resolution image to recover the "where" information. Transposed convolution represented by the white arrow pointing up is an exemplary upsampling technic that may be used in the expansive path 310 for upsampling of the feature map and expanding the size of images.

After the transposed convolution at block 325, the image is upsized from 28×28×1024→56×56×512, and then, the image is concatenated with the corresponding image from the contracting path (see the horizontal gray bar 330 from the contracting path 305) and together makes an image of size 56×56×1024. The reason for the concatenation is to combine the information from the previous layers (i.e., the high-resolution features from the contracting path 305 are combined with the upsampled output from the expansive path 310) in order to get a more precise prediction. This process continues as a sequence of up-convolutions (upsampling operators) that halves the number of channels, concatenations with a correspondingly cropped feature map from the contracting path 305, repeated application of convolutions (e.g., two 3×3 convolutions) that are each followed by a rectified linear unit (ReLU), and a final convolution in block 335 (e.g., one 1×1 convolution) to generate a multichannel segmentation as a two-dimensional segmentation mask. In order to localize, the U-Net 300 uses the valid part of each convolution without any fully connected layers, i.e., the segmentation map only contains the pixels for which the full context is available in the input image, and uses skip connections that link the context features learned during a contracting block and the localization features learned in an expansion block.

In instances in which only two-dimensional segmentation is performed, the two-dimensional segmentation mask output from the U-Net is used as input into a feature extractor and the feature extractor extracts relevant features from the two-dimensional segmentation mask. The relevant features and the two-dimensional segmentation mask are input into a classifier and the classifier transforms the relevant features and the two-dimensional segmentation mask into a final masked image. The classifier may use the relevant features to refine the classification of pixels in the two-dimensional segmentation mask and generate a final masked image. The final masked image is a high resolution masked image in which all the pixels are classified and segmentation outlines, borders, transparent patches, or the like are overlaid around and/or over specified segments (e.g., tumor tissue) based on the classified pixels.

In conventional U-Net architecture, the blocks of the contracting and expansive path are simply composed by convolutional layers (e.g., typically two or three layers) for performing the convolutions. However, in accordance with various embodiments, the blocks (e.g., blocks 315) are residual blocks comprising one or more layers that: (i) feed directly into a subsequent layer, and (ii) use a skip connection to feed directly into a layer that is multiple layers away from the one or more layers, which propagates larger gradients to the one or more layer during backpropagation. In certain instances the one or more layers of the residual blocks are pyramidal layers with separable convolutions performed at one or more levels of dilation.

Figure 4A:
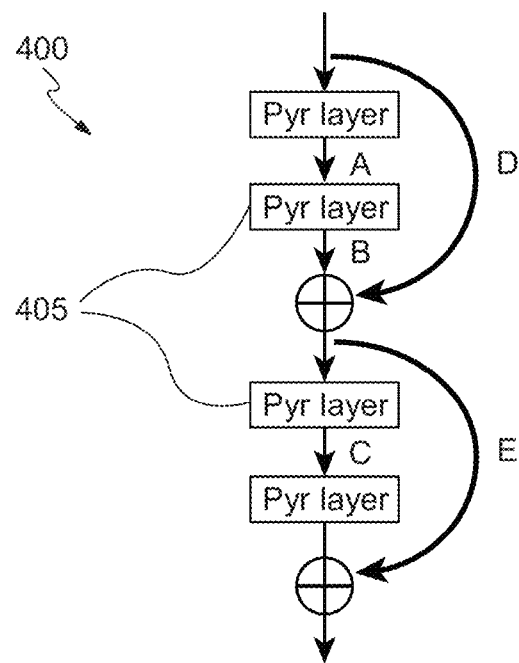
FIG. 4A shows a residual block according to various embodiments.

FIG. 4A illustrates a layer structure of one of the blocks 315 illustrated in FIG. 3. As shown, a residual block 400 may comprise multiple convolutional layers 405 (where in the embodiment shown, each single convolutional layer is replaced with two or more pyramidal layers 320). In a network (e.g., a ResNet) comprising residual blocks 400, one or more layer 405 (where in the embodiment shown, each layer is a pyramidal layer) feed directly into the next layer (A, B, C . . . ) and directly into a layer further away, such as e.g. multiple layers away (D, E . . . ). The use of residual blocks 400 in the network helps to overcome a degradation problem that occurs from increasing the number of convolutional or pyramidal layers (if the number of layers keeps increasing, accuracy will increase at first but will start to saturate at one point and eventually degrade). The residual blocks 400 skip some of these additional layers using the skip-connections or residual connections, which ultimately propagates larger gradients to initial layers during backpropagation. Skipping effectively simplifies the network, using fewer layers in the initial training stages. This speeds learning by reducing the impact of vanishing gradients, as there are fewer layers to propagate through (i.e., multi-speed residual learning). The network then gradually restores the skipped layers as it learns the feature space. Empirical evidence shows that the residual blocks allow for a gain of accuracy and easier optimization.

Figure 4B:
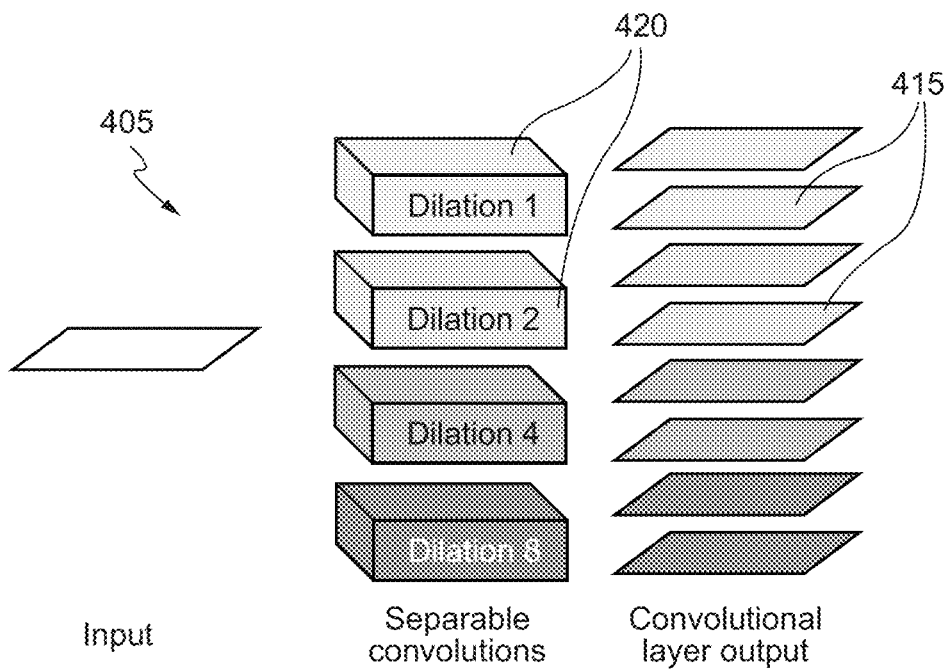
FIG. 4B shows a pyramidal layer according to various embodiments.

FIG. 4B illustrates a single pyramidal layer 405 of FIG. 4A, in accordance with various embodiments. The pyramidal layer 405 may use dilated (atrous) separable convolutions at multiple different scales ('dilation blocks'), in this example four levels. The pyramidal layer 405 comprises the same image at the multiple different scales in order to increase accuracy in detecting objects (e.g., a tumor). The separable convolutions of the pyramidal layer 405 are separable depthwise convolution, i.e., a spatial convolution performed independently over each channel of an input, followed by a pointwise convolution, e.g., a 1×1 convolution, projecting the channels output by the depthwise convolution onto a new channel space. The separable depthwise convolution provides a large gain in convergence speed and a significant reduction of the model size over the use of typical two-dimensional convolutions. The dilated (atrous) convolution inflates the kernel by inserting spaces between the kernel elements. This additional parameter 1 (dilation rate) for the spacing between kernel elements indicates how much the kernel will widen. This creates a filter with a "spread out" receptive field, which increases the size of the receptive field relative to the kernel size. In some embodiments, the dilation rate is four levels of dilation. In other embodiments, greater or fewer levels of dilation could be used, for example, six levels of dilation. The dilated (atrous) convolutions expand the receptive field without increasing the kernel size and without loss of resolution, which is especially effective when multiple dilated convolutions are stacked one after another as in the pyramidal layer 405.

The convolutional layer output 415 is the output of the dilation blocks 420 (labeled as Dilations 1, 2, 4, and 8). The illustrated example of FIG. 4B assumes four dilation blocks and that each dilation block outputs two channels (of the same color), so the total number of channels output is eight. The number of channels output by each dilation block may vary depending on the residual block in question. The example of FIG. 4B illustrates the top left residual block 315 or top right residual block 335 in FIG. 3. In some embodiments, the number of each of the channels output by each dilation block 415 in a pyramidal layer 410 of a residual block 405 is equal to the k number of filters on the residual block 405 divided by four.

III.D. Exemplary Component and Region Detection and Labeling

The PET scans, CT scans, and MRI scans can be highly heterogeneous depending on the position of the scans in the body due to the variable density and metabolism of organs. In order to limit this variability in downstream processing, a component detection model is configured to split a region or body depicted in the scans into multiple anatomical regions, for example, three regions including the head-neck, chest, and abdomen-pelvis. The component detection model automatically assesses the location of components (e.g., the liver and lungs) of the region or body captured in the two-dimensional segmentation mask as reference points, and uses the reference points to split the region or body into the multiple anatomical regions. Thereafter, the component detection model may generate location labels for the multiple anatomical regions and incorporate the location labels within two-dimensional segmentation mask. Downstream processing may use the labels as markers to select segments within the two-dimensional segmentation mask for processing by select CNN models (e.g., a CNN model specifically trained on scans from the head-neck region). This splitting and labeling narrows the imaging space and allows for select CNN models to be trained on different anatomical regions, which improves overall learning of the CNN models.

An approach such as the following may be used to detect the liver. A component detection model may perform a check to determine if the brain is present in a scan (e.g., a PET scan) by thresholding the scan with a threshold (e.g., a threshold of 2.0 SUV) and looking for a connected component larger than predetermined area or volume (e.g., 500 mm$^3$) after using morphological closing and opening with a structuring element of predefined radius (e.g., 8 mm) to fill the holes (e.g., background holes in images). The morphological closing is a mathematical operator comprising a dilation followed by an erosion using the same structuring element for both operations. The morphological opening is a mathematical operator comprising an erosion followed by a dilation using the same structuring element for both operations. The dilation operator takes two pieces of data as inputs. The first is the image which is to be dilated. The second is a (usually small) set of coordinate points known as a structuring element (also known as a kernel). It is this structuring element that determines the precise effect of the dilation on the input image. The basic effect of the dilation operator on a image is to gradually enlarge the boundaries of regions of foreground pixels (e.g., white pixels, typically). Thus areas of foreground pixels grow in size while holes within those regions become smaller. The erosion operator takes two pieces of data as inputs. The first is the image which is to be eroded. The second is a (usually small) set of coordinate points known as a structuring element (also known as a kernel). It is this structuring element that determines the precise effect of the erosion on the input image. The basic effect of the erosion operator on an image is to erode away the boundaries of regions of foreground pixels (e.g. white pixels, typically). Thus areas of foreground pixels shrink in size, and holes within those areas become larger. The component detection model looks at the bottom right part of the image and, using a predetermined threshold (e.g., a predetermined threshold of 1.0 SUV), fills the holes (using, e.g., closing or opening operations), erodes connected components with an erosion operator, and looks at the most superior connected component with a center of mass in the last third of the sagittal axis. The center of mass of this connected component lies within the liver. In other embodiments, alternate values for the terms mentioned above, and/or alternate methods may be used.

An approach such as the following may be used to detect the center of mass of the lungs. The component detection model may threshold segment an image at a predefined scale (e.g., −300 Hounsfield units (HU) for a CT scan) to obtain a binary mask and keep a number (e.g., eight) of the largest connected components identifiable within the image. In each slice (e.g., sagittal, axial, coronal, etc.), the component detection model may remove selected regions adjacent to the slice boundaries, erode the remaining connected components to avoid any leakage and keep only the two largest connected components. The model takes the center of mass of the two largest remaining connected components as the center of mass of the lungs (infers that the remaining two largest components are the lungs). In other embodiments, alternate values for the terms mentioned above, and/or alternate methods may be used.

Alternatively, the component detection model may use organ segmentation to assesses the location of components such as organs in the region or body depicted in the PET scans, CT scans, or MRI scans to obtain one or more reference points for the organs in the region or body. In some instances, the organ segmentation may additionally or alternatively be used for organ-specific measurements for one or more organs such as the spleen, liver, lungs, and kidneys. An approach such as the following may be used to segment one or more organs. The component detection model (e.g., a three-dimensional convolutional neural network, such as e.g., a V-Net for three-dimensional organ segmentation) may comprise downsampling and upsampling subnetworks, with skip connections to propagate higher resolution information to the final segmentation. In some instances, the downsampling subnetwork may be a sequence of multiple dense feature stacks connected by downsampling convolutions, each skip connection may be a single convolution of the corresponding dense feature stack output, and the upsampling network comprises bilinear upsampling to the final segmentation resolution. The output of the component detection model would be an organ segmentation mask for the input scan.

Once the components (e.g., the liver and lungs) of the regions or body are detected, the components may be used as reference points within the two-dimensional segmentation mask to split the region or body into multiple anatomical regions. The component detection model may generate location labels for the multiple anatomical regions and incorporate the location labels within the two-dimensional segmentation mask. As a result, the two-dimensional segmentation masks may include labels for the multiple anatomical regions. Downstream processing may use the labels as markers to select segments within the two-dimensional segmentation mask for processing by select CNN models (e.g., a CNN model specifically trained on scans from the head-neck region).

III.D. Exemplary V-Net for Three-Dimensional Segmentation

The three-dimensional segmentation based on a volumetric CNN system of multiple distinct submodels extracts features from patches of image data individually for each anatomical section. The patches of image data correspond to segments within the two-dimensional segmentation masks. Each patch includes volumes of image data having a fixed size voxels derived from both the pixel size and slice thickness of the patch. The patches may be defined by the border of the segments (i.e., the pixels classified as being part of the segmentation such as tumor tissue), a bounding box with coordinates generated to encompass the segments, or the border or the bounding box plus a buffer zone of predetermined number of pixels or voxels no ensure the entire segment is included within the patch of image data. System processing or the CNN system of multiple distinct submodels use the labels provided for the multiple anatomical regions as markers to select segments within the two-dimensional segmentation masks for input into select CNN models (e.g., a CNN model specifically trained on scans from a specified anatomical region such as the head-neck region).

Figure 5:
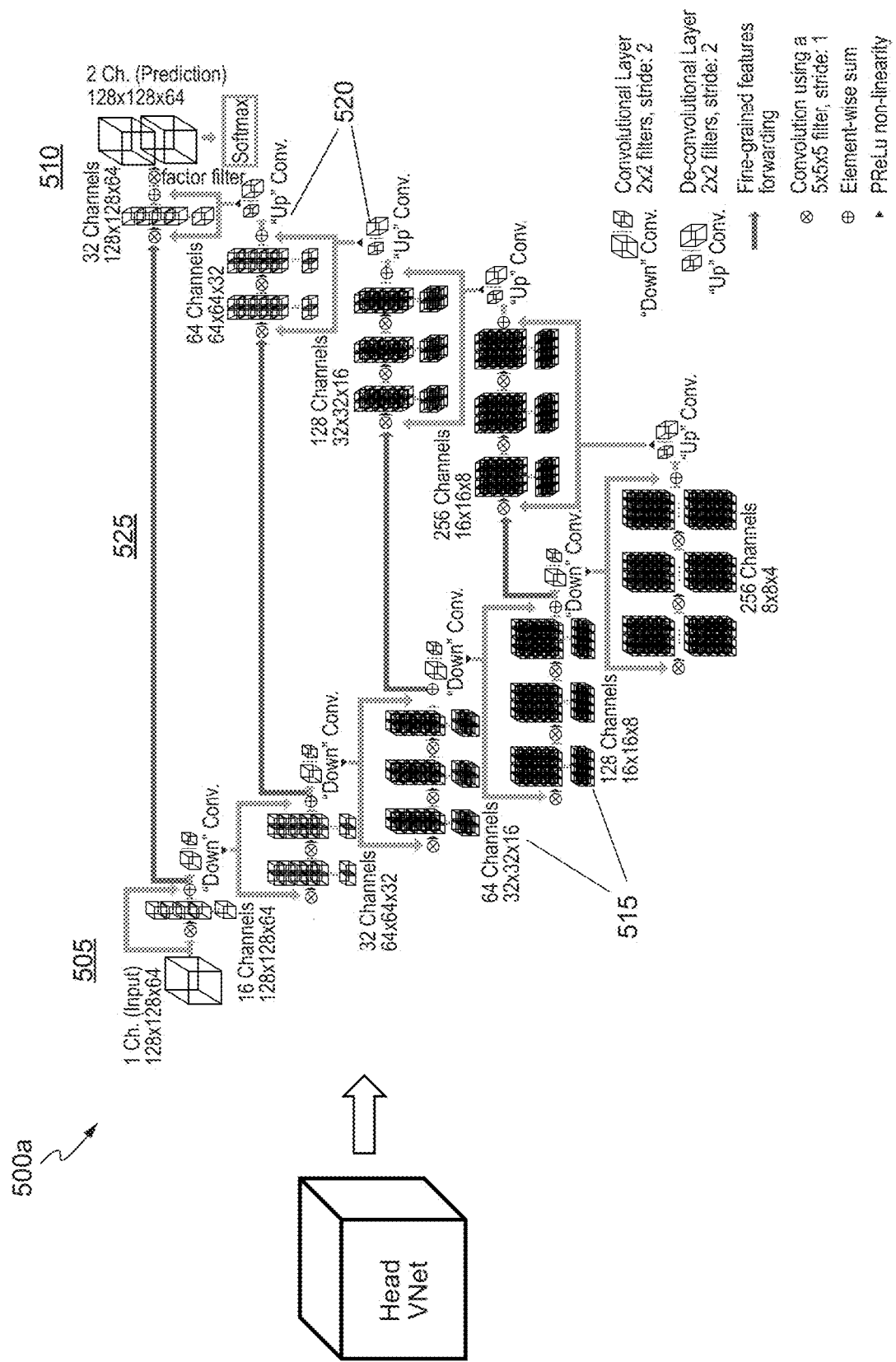
FIG. 5 shows multiple V-Nets according to various embodiments.
Figure 5:
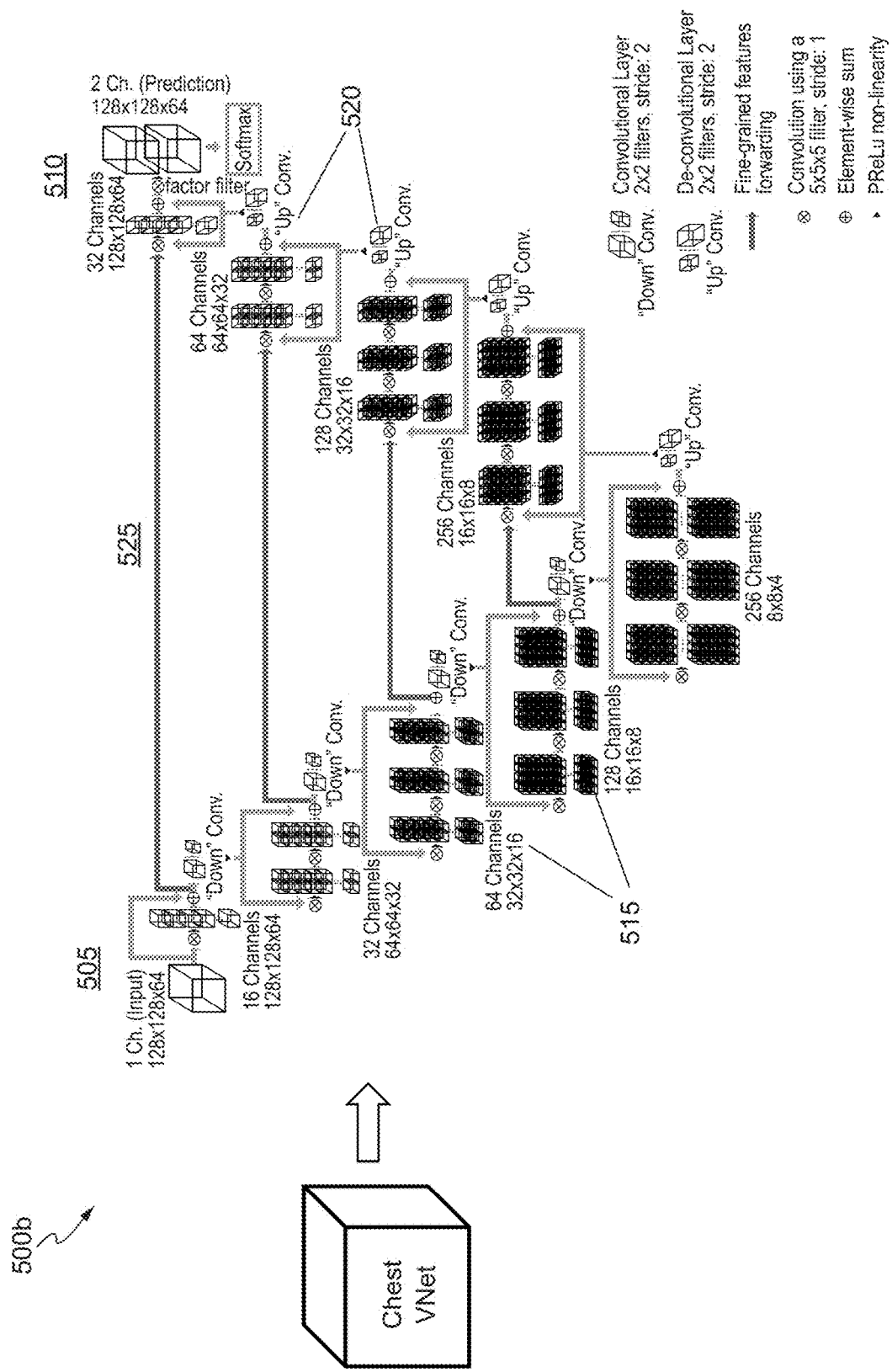
Figure 5:
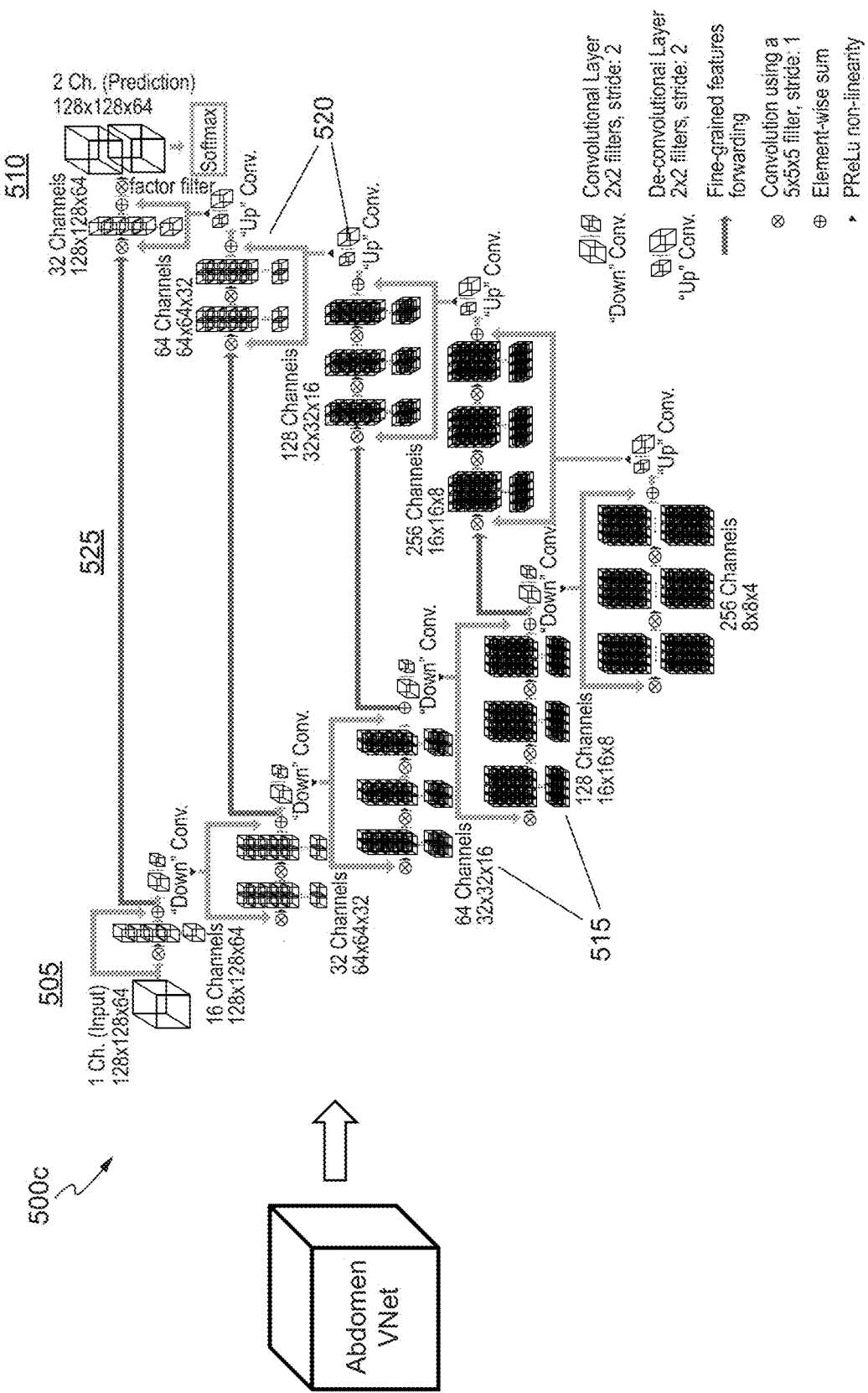

As shown in FIG. 5, for each of the anatomical regions labeled in the two-dimensional segmentation masks, a separate V-Net 500a-n may be used to refine image data within patches associated with each of the anatomical regions. The refinement of the image data within the patches comprises classifying the volumetric data for the voxels in each of the patches (i.e., the two-dimensional segmentation classified the pixels in a two-dimensional space and the three-dimensional segmentation will add in the classification for the voxels in a three-dimensional space). For example, each patch of image data can be considered as a matrix of pixel and voxel values, in which each pixel and voxel area of the matrix can be assigned with values. In some instances, the patches of image data include black-and-white characteristics having pixel or voxel values ranging from 0 and 1 and/or color characteristics that have three assigned RGB pixel or voxel values ranging from 0 and 255. In order to assign classifications to the voxels, each V-Net 500a-n will perform a series of operations on the patches of image data including: (1) convolution; (2) non-linearity conversion (e.g., ReLU); (3) pooling or sub sampling; and (4) classification (Fully Connected Layer), as described in detail below.

Each V-Net 500 includes a compression path 505 for downsampling and a decompression path 510 for upsampling that decompresses the signal until its original size is reached. The compression path 510 is divided in different blocks 515 that operate at different resolutions. Each block 515 may comprise one or more convolutional layers. Convolutions within each of the layers may be applied with appropriate padding. Each block 515 may be configured such that it learns a residual function via a residual connection: the input of each block 515 is (i) used in the convolutional layers and processed through the non-linearities, and (ii) added to the output of the last convolutional layer of that block in order to enable learning a residual function. The convolutions performed in each block 515 use volumetric kernels having a predetermined size such as 5×5×5 voxels. As the image data proceeds through different blocks 515 along the compression path 510, the resolution of the image data is reduced. This is performed through convolution with predetermined size kernels such as 2×2×2 voxel wide kernels applied with an appropriate stride (e.g., a slide of 2). Since the second operation extracts features by considering only non-overlapping volume patches, the size of the resulting feature maps is halved (sub-sampled). This strategy serves a similar purpose as pooling layers. Replacing pooling operations with convolutional ones results in a network with a smaller memory footprint, because no switches mapping the output of pooling layers back to their inputs are needed for back-propagation. Each of the stages of the compression path 505, computes a number of features which is multiple times higher than the number of feature from the previous layer or block.

The decompression path 510 is divided in different blocks 520 that operate to extract features and expand the spatial support of the lower resolution feature maps in order to gather and assemble the necessary information to output a multi-channel volumetric segmentation as a three-dimensional segmentation mask. After each block 520 of the decompression path 515, a de-convolution operation may be employed in order to increase the size of the inputs followed by one or multiple convolutional layers involving half the number of kernels such as 5×5×5 kernels employed in the previous layer. Similar to the compression path 510, residual functions may be learned in the convolutional stages of the decompression path 515. Additionally, the features extracted from early stages of the compression path 510 may be forwarded to the decompression path 515, as shown by the horizontal connections 525. The two feature maps computed by the very last convolutional layer, having an appropriate kernel size such as 1×1×1 kernel size and producing outputs of the same size as the input volume (two volumes having the same resolution as the original input patch of image data), may be processed through a soft-max layer which outputs the probability of each voxel belonging to a class such as the foreground or background.

In image data such as PET scans, CT scans, and MRI scans, it is not uncommon that the anatomy of interest (e.g., a tumor) occupies only a very small region of the scan. This often causes the learning process to get trapped in local minima of the loss function yielding a network whose predictions are strongly biased towards background. For example, the average proportion of negative voxels in a volume is 99.5% while it is always higher than 80% in a single slice. As a result, the foreground region is often missing or only partially detected. In order to deal with the unbalanced nature of images, an objective function based on a Dice Similarity Coefficient (DSC) can be used in the soft-max layer along with a weighted cross entropy for two-dimensions, as shown in Equation (2).

$$\mathcal{L}_{2D}(l) = 1 - \frac{2|\mathcal{P} \cap \mathcal{T}|}{|\mathcal{P}| + |\mathcal{T}|} + \sum_{v \in V} \left( \frac{|V|}{\sum_{v \in V} y_v} y_v \log(\hat{y}_v) + \left(1 - \frac{|V|}{\sum_{v \in V} y_v}\right)(1 - y_v)\log(1 - \hat{y}_v) \right)$$ Equation (2)

where V the voxel space, T the set of positive voxels, P refers to the set of predicted positive voxels, $y_v$ the value of voxel v in the three-dimensional segmentation mask and y_hat$_v$ the value of voxel v in the predicted three-dimensional segmentation mask.

In three dimensions, the DSC can be used along with Sensitivity and the Mean Absolute Error in the loss function, as shown in Equation (3).

$$\mathcal{L}_{3D}(l) = 1 - \frac{2|\mathcal{P} \cap \mathcal{T}|}{|\mathcal{P}| + |\mathcal{T}|} + 1 - \frac{|\mathcal{P} \cap \mathcal{T}|}{|\mathcal{T}|} + \frac{1}{|V|} \sum_{v \in V} |y_v - \hat{y}_v|$$ Equation (3)

where V the voxel space, T the set of positive voxels, P refers to the set of predicted positive voxels, $y_v$ the value of voxel v in the three-dimensional segmentation mask and y_hat$_v$ the value of voxel v in the predicted three-dimensional segmentation mask.

It will be appreciated that, while FIG. 5 depicts using three V-Nets 500 (each with two paths) to refine the patches of image data from the two-dimensional segmentation masks, different numbers V-Nets and of convolutional layers may be used (e.g., which may have an effect of repeating these operations by the CNN system one or more times). For example, outputs can be determined by applying five or more convolutional layers to extract features from the patches of image data for determination of present or future prediction pertaining to tumor segmentation.

In instances in which two-dimensional segmentation and three-dimensional segmentation are performed, the two-dimensional segmentation mask and the three-dimensional segmentation masks are used as input into a feature extractor and the feature extractor extracts relevant features from the two-dimensional segmentation mask and the three-dimensional segmentation masks. The relevant features extracted from the feature extractor, the two-dimensional segmentation mask, and the three-dimensional segmentation masks are input into a classifier, and the classifier transforms the relevant features extracted, the two-dimensional segmentation mask, and the three-dimensional segmentation masks into a final masked image. For example, the classifier uses the relevant features to refine the classification of pixels in each of the two-dimensional segmentation masks and the three-dimensional segmentation masks. Thereafter, the classifier combines the refined the two-dimensional segmentation mask and the three-dimensional segmentation masks to generate a final masked image. For example, the final mask image may be obtained by a averaging (or applying one or more other statistical operations) the refined two-dimensional segmentation masks and the three-dimensional segmentation masks. The final masked image is a high resolution masked image in which all the pixels and voxels are classified and segmentation outlines, borders, transparent patches, or the like are overlaid around and/or over specified segments (e.g., tumor tissue) based on the classified pixels and voxels.

IV. Techniques for Extraction and Prediction

Figure 6:
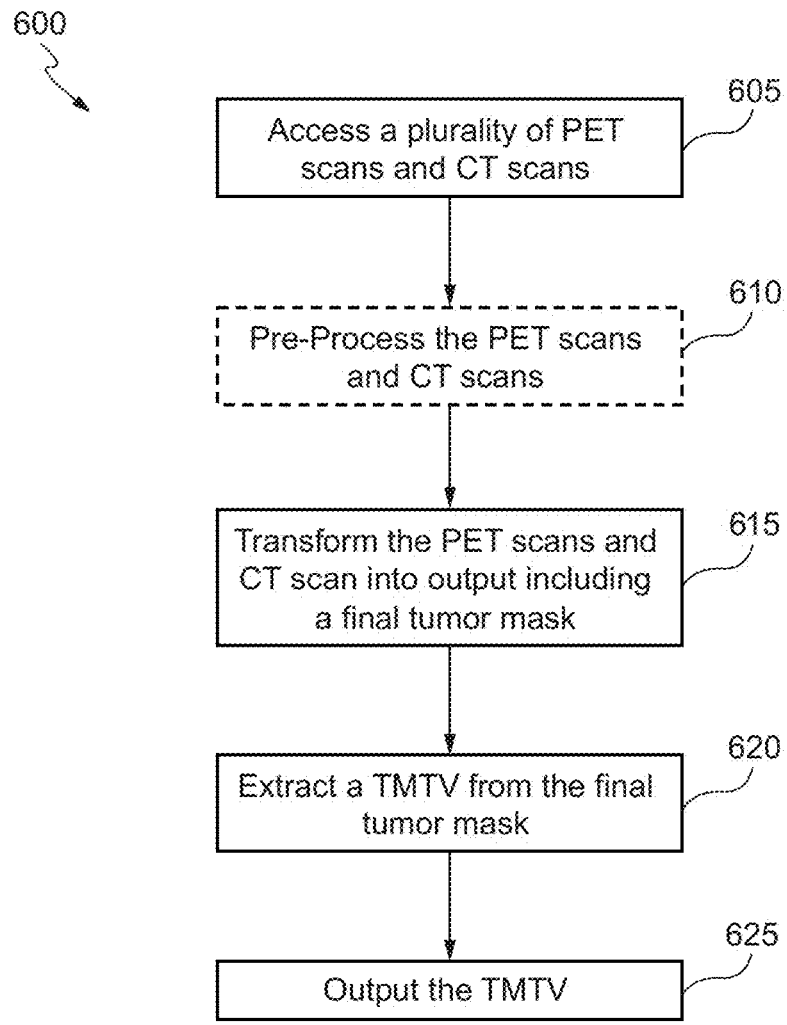
FIG. 6 shows a process for determining an extracted total metabolic tumor volume (TMTV) in accordance with various embodiments.

FIG. 6 shows a process 600 for determining an extracted TMTV in accordance with various embodiments.

Process 600 begins at block 605, at which a plurality of PET (or SPECT) scans (e.g., FDG-PET scans) for a subject and a plurality of CT or MRI scans for the subject are accessed. The PET scans and corresponding CT or MRI scans can depict at least part of the body of a subject or a whole body of the subject. For example, the PET scans and corresponding CT or MRI scans may depict one or more organs of the body including the lungs, liver, brain, heart, or any combination thereof. Optionally, at block 610, the PET scans and corresponding CT or MRI scans may be preprocessed to generate subsets of standardized images or scans for slices (e.g., coronal, axial, and sagittal slices) or regions of the body.

At block 615, a CNN architecture is used to transform the PET scans and corresponding CT or MRI scans into an output (e.g., a final masked image). In some embodiments, the CNN architecture includes one or more two-dimensional segmentation models such as modified U-Nets, as described in detail herein. The two-dimensional segmentation model(s) are configured to generate a two-dimensional segmentation mask(s) from the PET scans and corresponding CT or MRI scans or the subsets of standardized images or scans. The two-dimensional segmentation model(s) use a plurality of residual blocks, each residual block having separable convolutions and a plurality of dilations, on the PET scans and corresponding CT or MRI scans or the subsets of standardized images or scans to generate a two-dimensional segmentation mask. The two-dimensional segmentation mask(s) may be refined using a feature extractor and classifier, and thereafter combined (e.g., using an average or other statistical function(s)) to generate a final masked image in which all the pixels are classified and segmentation outlines, borders, transparent patches, or the like are overlaid around and/or over specified segments (e.g., tumor tissue) based on the classified pixels.

In other embodiments, the CNN architecture includes one or more two-dimensional segmentation models and a plurality of three-dimensional segmentation models, as described in detail herein. The two-dimensional segmentation model(s) are configured to generate a two-dimensional segmentation mask(s) from the PET scans and corresponding CT or MRI scans or the subsets of standardized images or scans. The three-dimensional segmentation models are configured to generate three-dimensional segmentation masks from the PET scans and corresponding CT or MRI scans or the subsets of standardized images or scans. The three-dimensional segmentation models may use residual connections and multi-term loss on the PET scans and corresponding CT or MRI scans or the subsets of standardized images or scans to generate three-dimensional segmentation masks. The two-dimensional segmentation mask(s) and the three-dimensional segmentation masks may be refined using a feature extractor and classifier, and thereafter combined (e.g., using an average or other statistical function(s)) to generate a final masked image in which all the pixels and voxels are classified and segmentation outlines, borders, transparent patches, or the like are overlaid around and/or over specified segments (e.g., tumor tissue) based on the classified pixels and voxels.

In instances in which the CNN architecture utilizes one or more two-dimensional segmentation models and a plurality of three-dimensional segmentation models, the CNN architecture may split a region or body depicted in the PET scans and CT or MRI scans or the subsets of standardized images or scans into multiple anatomical regions, for example, three regions including the head-neck, chest, and abdomen-pelvis. The CNN architecture automatically assesses the location of components of the region or body captured in the PET scans and CT or MRI scans or the subsets of standardized images or scans as reference points, and uses the reference points to split the region or body into the multiple anatomical regions. Thereafter, the CNN architecture may generate location labels for the multiple anatomical regions and incorporate the location labels within the two-dimensional segmentation mask(s). Image patches associated with segments within the two-dimensional segmentation mask(s) can be separated into each of the multiple anatomical regions and image processed by a different three-dimensional segmentation model (which may share an architecture but have different learned parameters).

At block 620, a TMTV may be extracted from the final masked image. In some instances, the CNN architecture segments tumors in each anatomical region based on features extracted from the PET scans and CT or MRI scans including the SUV values from the PET scans. A metabolic tumor volume (MTV) may be determined for each segmented tumor. The TMTV for a given subject may be determined from all of the segmented tumors, and represents the sum of all individual MTVs.

At block 625, the TMTV is output. For example, the TMTV may be locally presented or transmitted to another device. The TMTV may be output along with an identifier of the subject. In some instances, the TMTV is output with the final masked image and/or other information that identifies image regions, features and/or detections that contributed to the extraction of the TMTV. Thereafter, a diagnosis may be provided and/or a treatment may be administered to the subject or the subject may have been administered a treatment based on the extracted TMTV.

Figure 7:
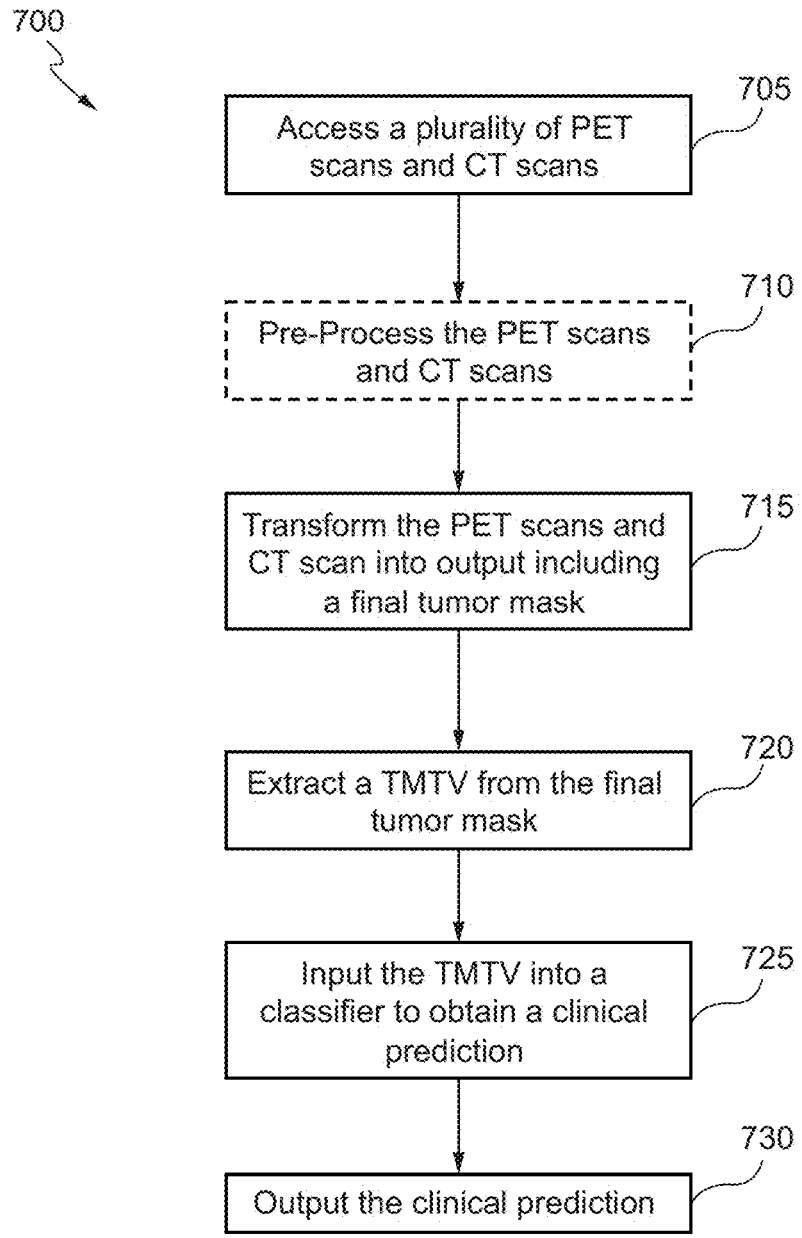
FIG. 7 shows a process for predicting a likelihood of progression free survival (PFS) for the subject, the clinical efficacy of a treatment, a disease stage of the subject, and/or a selection decision for including the subject in a clinical trial, in accordance with various embodiments.

FIG. 7 shows a process 700 for predicting a likelihood of progression free survival (PFS) for the subject, the clinical efficacy of a treatment, a disease stage of the subject, and/or a selection decision for including the subject in a clinical trial, in accordance with various embodiments.

Process 700 begins at block 705, at which a plurality of PET (or SPECT) scans (e.g., FDG-PET scans) for a subject and a plurality of CT or MRI scans for the subject are accessed. The PET scans and corresponding CT or MRI scans can depict at least part of the body of a subject or a whole body of the subject. For example, the PET scans and corresponding CT or MRI scans may depict one or more organs of the body including the lungs, liver, brain, heart, or any combination thereof. Optionally, at block 710, the PET scans and corresponding CT or MRI scans may be preprocessed to generate subsets of standardized images or scans for slices (e.g., coronal, axial, and sagittal slices) or regions of the body.

At block 715, a CNN architecture is used to transform the PET scans and corresponding CT or MRI scans into an output (e.g., a final masked image). In some embodiments, the CNN architecture includes one or more two-dimensional segmentation models such as modified U-Nets, as described in detail herein. The two-dimensional segmentation model(s) are configured to generate a two-dimensional segmentation mask(s) from the PET scans and corresponding CT or MRI scans or the subsets of standardized images or scans. The two-dimensional segmentation model(s) use a plurality of residual blocks, each residual block having separable convolutions and a plurality of dilations, on the PET scans and corresponding CT or MRI scans or the subsets of standardized images or scans to generate a two-dimensional segmentation mask. The two-dimensional segmentation mask(s) may be refined using a feature extractor and classifier, and thereafter combined (e.g., using an average or other statistical function(s)) to generate a final masked image in which all the pixels are classified and segmentation outlines, borders, transparent patches, or the like are overlaid around and/or over specified segments (e.g., tumor tissue) based on the classified pixels.

In other embodiments, the CNN architecture includes one or more two-dimensional segmentation models and a plurality of three-dimensional segmentation models, as described in detail herein. The two-dimensional segmentation model(s) are configured to generate a two-dimensional segmentation mask(s) from the PET scans and corresponding CT or MRI scans or the subsets of standardized images or scans. The three-dimensional segmentation models are configured to generate three-dimensional segmentation masks from the PET scans and corresponding CT or MRI scans or the subsets of standardized images or scans. The three-dimensional segmentation models may use residual connections and multi-term loss on the PET scans and corresponding CT or MRI scans or the subsets of standardized images or scans to generate three-dimensional segmentation masks. The two-dimensional segmentation mask(s) and the three-dimensional segmentation masks may be refined using a feature extractor and classifier, and thereafter combined (e.g., using an average or other statistical function(s)) to generate a final masked image in which all the pixels and voxels are classified and segmentation outlines, borders, transparent patches, or the like are overlaid around and/or over specified segments (e.g., tumor tissue) based on the classified pixels and voxels.

In instances in which the CNN architecture utilizes one or more two-dimensional segmentation models and a plurality of three-dimensional segmentation models, the CNN architecture may split a region or body depicted in the PET scans and CT or MRI scans or the subsets of standardized images or scans into multiple anatomical regions, for example, three regions including the head-neck, chest, and abdomen-pelvis. The CNN architecture automatically assesses the location of components of the region or body captured in the PET scans and CT or MRI scans or the subsets of standardized images or scans as reference points, and uses the reference points to split the region or body into the multiple anatomical regions. Thereafter, the CNN architecture may generate location labels for the multiple anatomical regions and incorporate the location labels within the two-dimensional segmentation mask(s). Image patches associated with segments within the two-dimensional segmentation mask(s) can be separated into each of the multiple anatomical regions and image processed by a different three-dimensional segmentation model (which may share an architecture but have different learned parameters).

Optionally, at block 720, a separate three-dimensional CNN is used to transform the PET scans and corresponding CT or MRI scans into an output associated with organ segmentation. The three-dimensional CNN may include a three-dimensional segmentation model configured to generate a three-dimensional organ mask from the PET scans and corresponding CT scans. The three-dimensional segmentation model may use downsampling and upsampling subnetworks, with skip connections to propagate higher resolution information to generate a three-dimensional organ mask.

At block 725, a TMTV may be extracted from the final masked image. In some instances, the CNN architecture segments tumors in each anatomical region based on features extracted from the PET scans and CT or MRI scans including the SUV values from the PET scans. A metabolic tumor volume (MTV) may be determined for each segmented tumor. The TMTV for a given subject may be determined from all of the segmented tumors, and represents the sum of all individual MTVs. Optionally, organ specific measurements such as the MTV and number of lesions per organ (e.g., number of lesions>1 ml) may be extracted from the final masked image and the three-dimensional organ mask. Organ involvement may be defined as an automated organ MTV>0.1 mL for noise reduction purposes.

At block 730, one or more of the extracted TMTV, the extracted MTV (e.g., for each organ), and the number of lesions per organ are input into a classifier to generate a clinical prediction for the subject. In some instances, a clinical predicted metric is obtained as an output of a classifier that uses as input at least part of the final mask output and/or the extracted TMTV. In other instances, a clinical predicted metric is obtained as an output of a classifier that takes as input one or more of at least part of the three-dimensional organ mask output, the extracted MTV, and/or the number of lesions. The clinical predicted metric can correspond to a clinical prediction. In some instances, the clinical prediction is a likelihood of progression free survival (PFS) for the subject, a disease stage of the subject, and/or a selection decision for including the subject in a clinical trial. A Kaplan-Meier analysis may be used to assess PFS and a Cox proportional hazards model may be used to estimate the prognostic value of organ-specific involvement.

At block 735, the clinical prediction is output. For example, the clinical prediction may be locally presented or transmitted to another device. The clinical prediction may be output along with an identifier of the subject. In some instances, the clinical prediction is output with TMTV, TMV, the number of lesions, the final mask output, the three-dimensional organ mask output, and/or other information that identifies image regions, features and/or detections that contributed to the clinical prediction. Thereafter, a diagnosis may be provided and/or a treatment may be administered to the subject or the subject may have been administered a treatment based on the clinical prediction.

Figure 8:
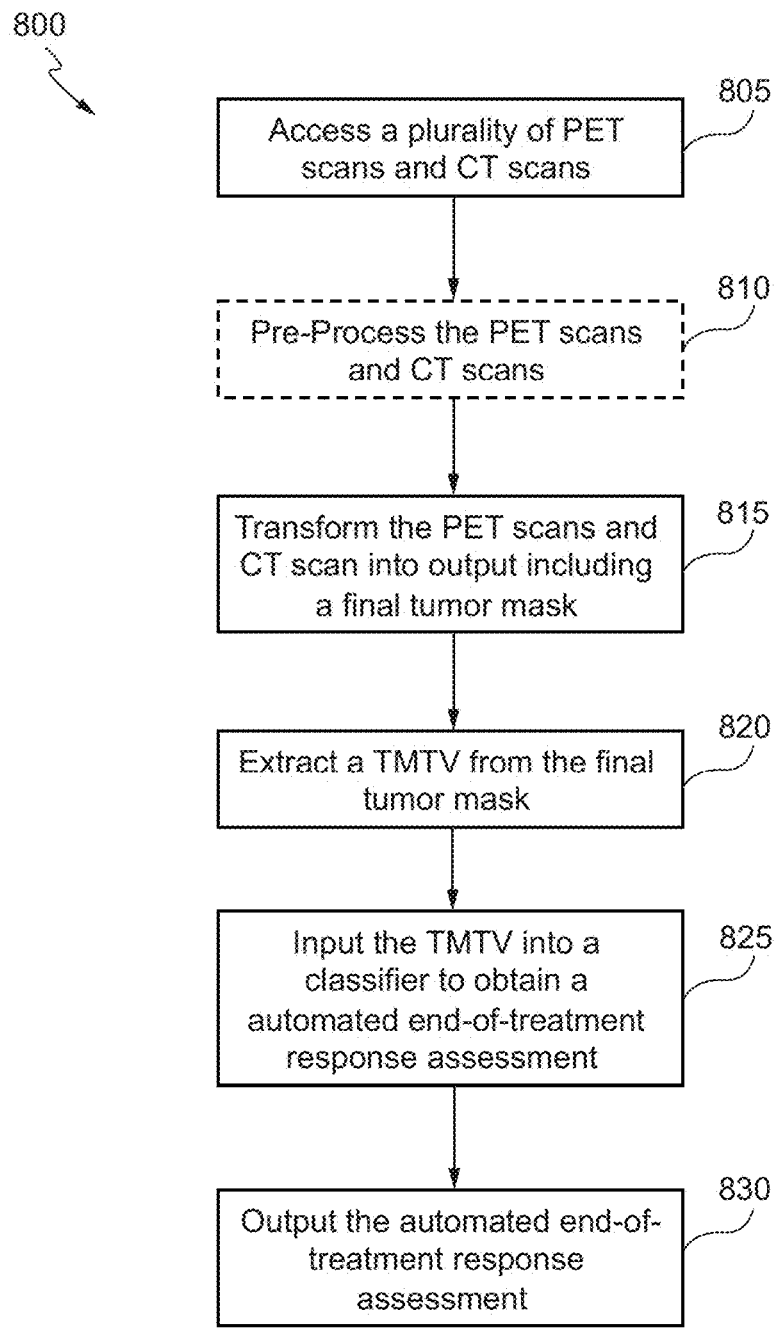
FIG. 8 shows a process for providing automated end-of-treatment response assessment, which may include a Lugano classification for staging of lymphomas, in accordance with various embodiments.
Figure 9A:
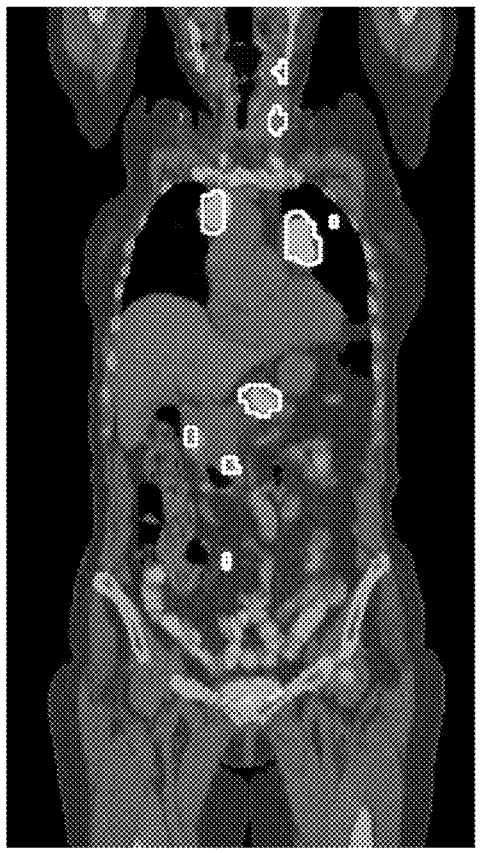
Figure 9B:
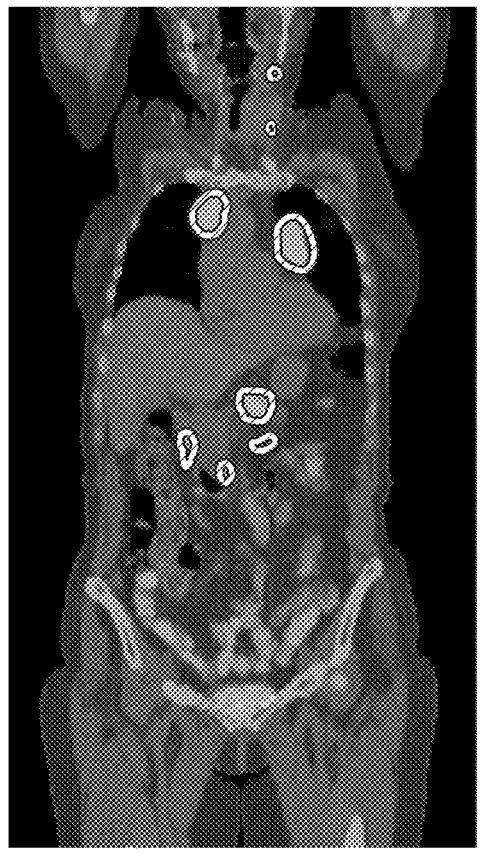
Figure 9C:
Figure 9D:

FIG. 8 shows a process 800 for providing automated end-of-treatment response assessment, which may include a Lugano classification for staging of lymphomas, in accordance with various embodiments.

Process 800 begins at block 805, at which a plurality of PET (or SPECT) scans (e.g., FDG-PET scans) for a subject and a plurality of CT or MRI scans for the subject are accessed. The PET scans and corresponding CT or MRI scans can depict at least part of the body of a subject or a whole body of the subject. For example, the PET scans and corresponding CT or MRI scans may depict one or more organs of the body including the lungs, liver, brain, heart, or any combination thereof. Optionally, at block 810, the PET scans and corresponding CT or MRI scans may be preprocessed to generate subsets of standardized images or scans for slices (e.g., coronal, axial, and sagittal slices) or regions of the body.

At block 815, a CNN architecture is used to transform the PET scans and corresponding CT or MRI scans into an output (e.g., a final masked image). In some embodiments, the CNN architecture includes one or more two-dimensional segmentation models such as modified U-Nets, as described in detail herein. The two-dimensional segmentation model(s) are configured to generate a two-dimensional segmentation mask(s) from the PET scans and corresponding CT or MRI scans or the subsets of standardized images or scans. The two-dimensional segmentation model(s) use a plurality of residual blocks, each residual block having separable convolutions and a plurality of dilations, on the PET scans and corresponding CT or MRI scans or the subsets of standardized images or scans to generate a two-dimensional segmentation mask. The two-dimensional segmentation mask(s) may be refined using a feature extractor and classifier, and thereafter combined (e.g., using an average or other statistical function(s)) to generate a final masked image in which all the pixels are classified and segmentation outlines, borders, transparent patches, or the like are overlaid around and/or over specified segments (e.g., tumor tissue) based on the classified pixels.

In other embodiments, the CNN architecture includes one or more two-dimensional segmentation models and a plurality of three-dimensional segmentation models, as described in detail herein. The two-dimensional segmentation model(s) are configured to generate a two-dimensional segmentation mask(s) from the PET scans and corresponding CT or MRI scans or the subsets of standardized images or scans. The three-dimensional segmentation models are configured to generate three-dimensional segmentation masks from the PET scans and corresponding CT or MRI scans or the subsets of standardized images or scans. The three-dimensional segmentation models may use residual connections and multi-term loss on the PET scans and corresponding CT or MRI scans or the subsets of standardized images or scans to generate three-dimensional segmentation masks. The two-dimensional segmentation mask(s) and the three-dimensional segmentation masks may be refined using a feature extractor and classifier, and thereafter combined (e.g., using an average or other statistical function(s)) to generate a final masked image in which all the pixels and voxels are classified and segmentation outlines, borders, transparent patches, or the like are overlaid around and/or over specified segments (e.g., tumor tissue) based on the classified pixels and voxels.

In instances in which the CNN architecture utilizes one or more two-dimensional segmentation models and a plurality of three-dimensional segmentation models, the CNN architecture may split a region or body depicted in the PET scans and CT or MRI scans or the subsets of standardized images or scans into multiple anatomical regions, for example, three regions including the head-neck, chest, and abdomen-pelvis. The CNN architecture automatically assesses the location of components of the region or body captured in the PET scans and CT or MRI scans or the subsets of standardized images or scans as reference points, and uses the reference points to split the region or body into the multiple anatomical regions. Thereafter, the CNN architecture may generate location labels for the multiple anatomical regions and incorporate the location labels within the two-dimensional segmentation mask(s). Image patches associated with segments within the two-dimensional segmentation mask(s) can be separated into each of the multiple anatomical regions and image processed by a different three-dimensional segmentation model (which may share an architecture but have different learned parameters).

At block 820, a TMTV may be extracted from the final masked image. In some instances, the CNN architecture segments tumors in each anatomical region based on features extracted from the PET scans and CT or MRI scans including the SUV values from the PET scans. A metabolic tumor volume (MTV) may be determined for each segmented tumor. The TMTV for a given subject may be determined from all of the segmented tumors, and represents the sum of all individual MTVs.

At block 825, the extracted TMTV is input into a classifier to generate an automated end-of-treatment response assessment based on the TMTV. The automated end-of-treatment response assessment can correspond to a predicted current or future occurrence, speed or magnitude of progression of a tumor. The automated end-of-treatment response assessment may include (for example) a progression score along a particular scale (e.g., a tumor grade). In some instances, the automated end-of-treatment response assessment and/or the output includes a difference between a progression score at a predefined time point and a baseline time point. In some instances, the automated end-of-treatment response assessment and/or the output includes a binary indicator, such as a binary value representing a prediction as to whether a subject's tumor will progress by at least a predefined amount within a predefined time period. In some instances, the automated end-of-treatment response assessment includes a prediction for a Lugano classification for staging of lymphomas.

At block 830, the automated end-of-treatment response assessment is output. For example, the automated end-of-treatment response assessment may be locally presented or transmitted to another device. The automated end-of-treatment response assessment may be output along with an identifier of the subject. In some instances, the automated end-of-treatment response assessment is output with TMTV, the final mask output, and/or other information that identifies image regions, features and/or detections that contributed to the automated end-of-treatment response assessment. Thereafter, a diagnosis may be provided and/or a treatment may be administered to the subject or the subject may have been administered a treatment based on the automated end-of-treatment response assessment.

V. EXAMPLES

The systems and methods implemented in various embodiments may be better understood by referring to the following examples.

V.A. Example 1. —Fully Automated Measurement of Total Metabolic Tumor Burden in Diffuse Large B-Cell Lymphoma and Follicular Lymphoma Baseline TMTV from FDG PET/CT scans are shown to be prognostic for progression free survival in lymphoma, such as Diffuse Large B-Cell Lymphoma (DLBCL) and Follicular Lymphoma (FL).

V.B. Data

The data set is comprised of a total of 3,506 whole body (including Chest Abdomen Pelvis) FDG-PET/CT scans collected from multiple sites, over 1.5 million images of Lymphoma and Lung Cancer subjects. This dataset contains scans of 1595 Non Hodgkin Lymphomas subjects with a complete ground truth, 1133 DLBCL subjects and 562 FL subjects, and 158 Non-Small Cell Lung Cancer (NSCLC) subjects with partial ground truths. Data was stored in the DICOM format.

The data originated from two Phase 3 clinical trials in subjects with NHL (Goya, N=1401, NCT01287741; and Gallium, N=595, NCT01332968). FDG-PET images and semi-automatically defined three-dimensional tumor contours. After pre-processing, a total of 870 (Goya only) baseline scans and associated segmentation masks were used for algorithm training. Additionally, a separate set of 400 randomly selected datasets (250 Goya, 150 Gallium) were held out for testing purposes.

V.C. Preprocessing

Preprocessing included aligning the PET scans and CT scans, re-sampling scans to get an isotropic voxel size of 2×2×2 mm and deriving the SUV for PETs using the information in the DICOM header. Segmentation masks were reconstructed from RTStruct files as ground truths for training of the CNN architecture.

The 1133 DLBCL subjects were used as a training dataset. This includes a total of 861,053 coronal, 770,406 sagital and 971,265 axial slices and 13,942 individual tumors. The test set comprised a total of 1066 scans of FL subjects and 316 scans from NSCLC subjects.

This split was adopted and such a large portion of the data was kept for testing for two reasons. One concern was to be able to validate that the model can be extended to another type of cancer. Thus all Folicular Lymphoma subjects were kept in the test set. In addition, only up to 5 lesions have been segmented for Lung Cancer subjects in the data set. Consequently, these scans have been excluded from the training set in order to avoid training on data with false negatives and used sensitivity to validate the performance of the algorithm on these scans.

V.D. Training Procedure

Experiments were conducted in order to determine the best set of hyper parameters. The learning rate was varied (coarse-fine tuning) and tested a variable learning rate (cosine annealing) for each network. For two-dimensional CNNs, experiments included testing 2 kernel sizes, 3×3 and 5×5, a kernel size of 5×5 does not lead to a performance gain and slows the model. Experiments were also conducted to determine the optimal depth of the U-Net. Increasing the depth from 6 to 7 did not improve the performance metrics. Predictions over axial slices were removed as they led to a high number of false positives with a high activity (e.g., kidneys, heart, bladder).

A two-dimensional network associated with processing images or scans from the coronal plane and a two-dimensional network associated with processing images or scans from the sagittal plane were trained on 2 Nvidia Quadro P6000 graphical processing units (GPUs) using the RMSProp optimizer, 160,000 iterations, a batch size of 8. The learning rate was set at 1e-5 for 80,000 iterations and divided by 2 every 20,000 iterations after. More than 80% of the slices do not contain any tumors. In order to avoid converging to a null prediction, the dataset was rebalanced to reach a percentage of approximately 10% of healthy slices (98,000 training slices for each view).

V-Nets were trained using an optimizer (e.g., the optimizer disclosed in Bauer C, Sun S, Sun W, et al. Automated measurement of uptake in cerebellum, liver, and aortic arch in full-body FDG PET/CT scans. Med Phys. 2012; 39(6): 3112-23, https://doi.org/10.1118/1.4711815), a learning rate 1e-4, on 200,000 iterations and the learning rate was set 1e-4 to 100,000 iterations, 1e-4=2 for 50,000 iterations and 1e-4=4 for 50,000 iterations.

Tumors were manually segmented and peer reviewed by certified radiologists. Compared to radiologist tumor segmentation, the model reports a mean voxel sensitivity of 92.7% on a test set of 1,470 scans, and a mean three-dimensional-Dice score of 88.6% on 1,064 scans.

V.E. Segmentation Results

To perform three-dimensional segmentation, the model uses patches of image data associated with segments identified in the two-dimensional segmentation masks obtained from the two-dimensional segmentation models discussed herein. Both the FDG-PET and CT or MRI are used as an input to the CNN architecture. The connected components in the two-dimensional segmentation masks are labeled depending on their relative location to the references in the liver and the chest. For each of these anatomical region a separate V-Net was used to refine the two-dimensional segmentation. In one example embodiment, the network contains with 4 downsampling blocks and 3 upsampling blocks, and layers use a ReLu activation and a 3×3×3 kernel size. In this example embodiment, patches are 32×32×32×2 in the head or neck, 64×64×64×2 in the chest and 96×96×96×2 in the abdomen.

Segmentation results are presented in Table 1 and FIGS. 9A-9F. In FIGS. 9A-9F, for each subfigure, left is ground truth and right is prediction, in accordance with this example embodiment. Both the CT and the SUV are used as inputs to leverage the structural and metabolic information provided by each modality. In the examples shown in FIGS. 9A-9F, the input size is 448×512×2. The number of convolutions of the first layer is 8 and is multiplied by two along the downsampling block. A separate network was used for each of the coronal and sagittal planes. Only up to 5 lesions have been segmented for these example Lung Cancer scans, thus sensitivity is reported for these scans. The method is more accurate than conventional algorithms relying on manual intervention (DSC respectively of 0.732 and 0.85). The method is applicable to whole body FDG-PET/CT scans and could the model trained on DLBCL subjects can be transferred to FL subjects and NSCLC subjects.

TABLE 1

Results of Segmentation

| Dataset | # of Scans | Dice Score | Sensitivity |
|---|---|---|---|
| Training | 2266 | 0.895 | 0.932 |
| Follicular Lymphoma (test) | 1124 | 0.886 | 0.926 |
| Lung Cancer (test) | 316 | — | 0.930 |

V.F. Comparison of the Total Metabolic Tumor Volume and $SUV_{max}$

Figure 10A:
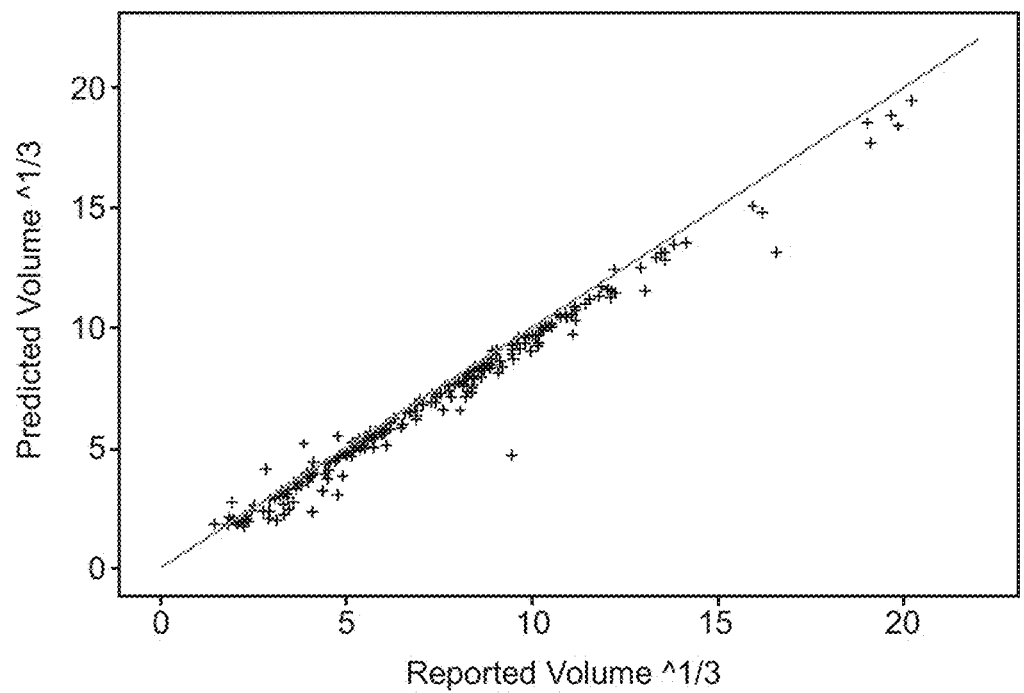
FIGS. 10A and 10B show tumor volume and standardized uptake value $(SUV)_{max}$, respectively, from the predicted masks according to various embodiments.
Figure 10B:
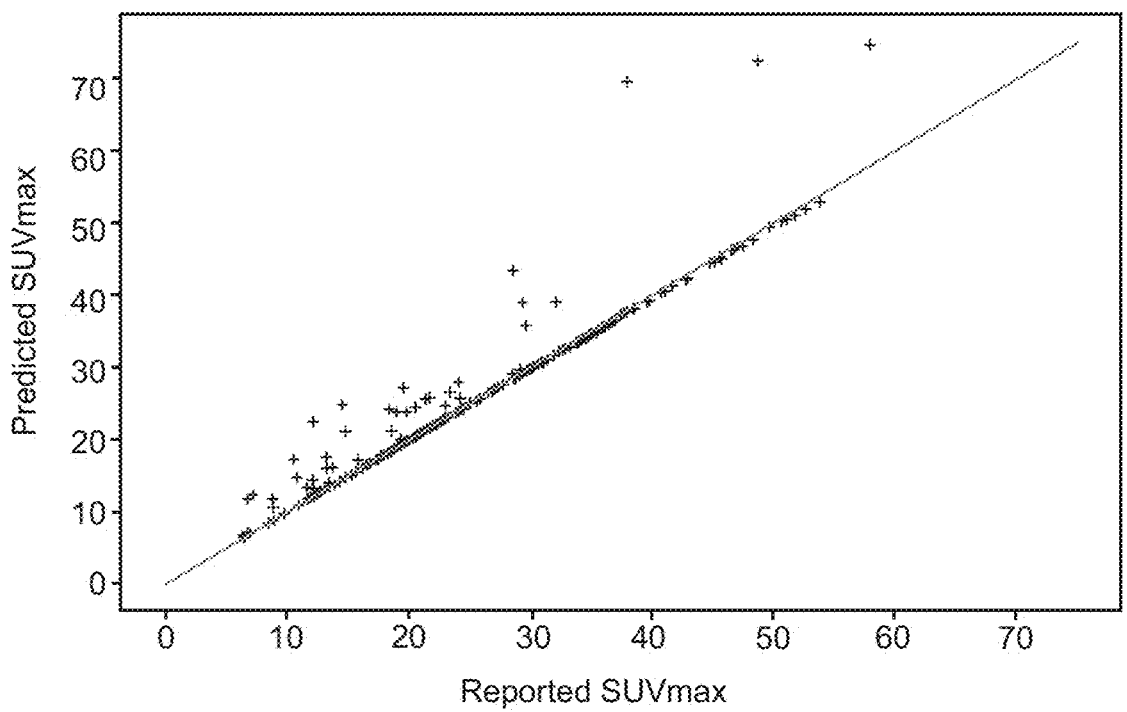
Figure 11A:
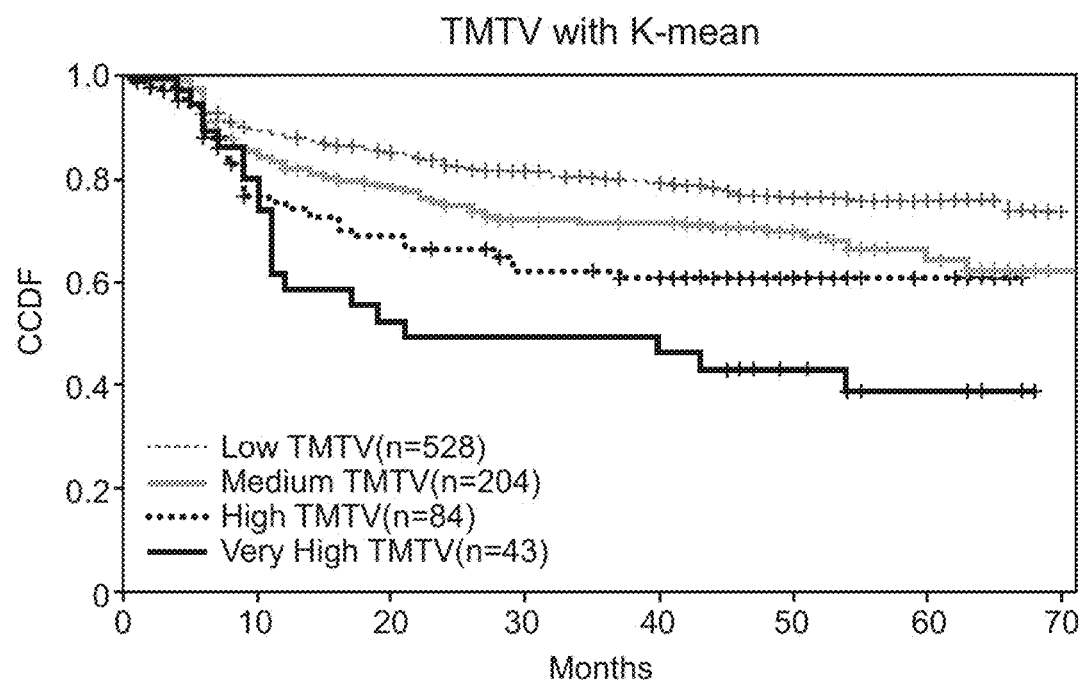
FIGS. 11A and 11B show Kaplan-Meier estimators of clusters showing the relevance of the TMTV for prognosis according to various embodiments.
Figure 11B:
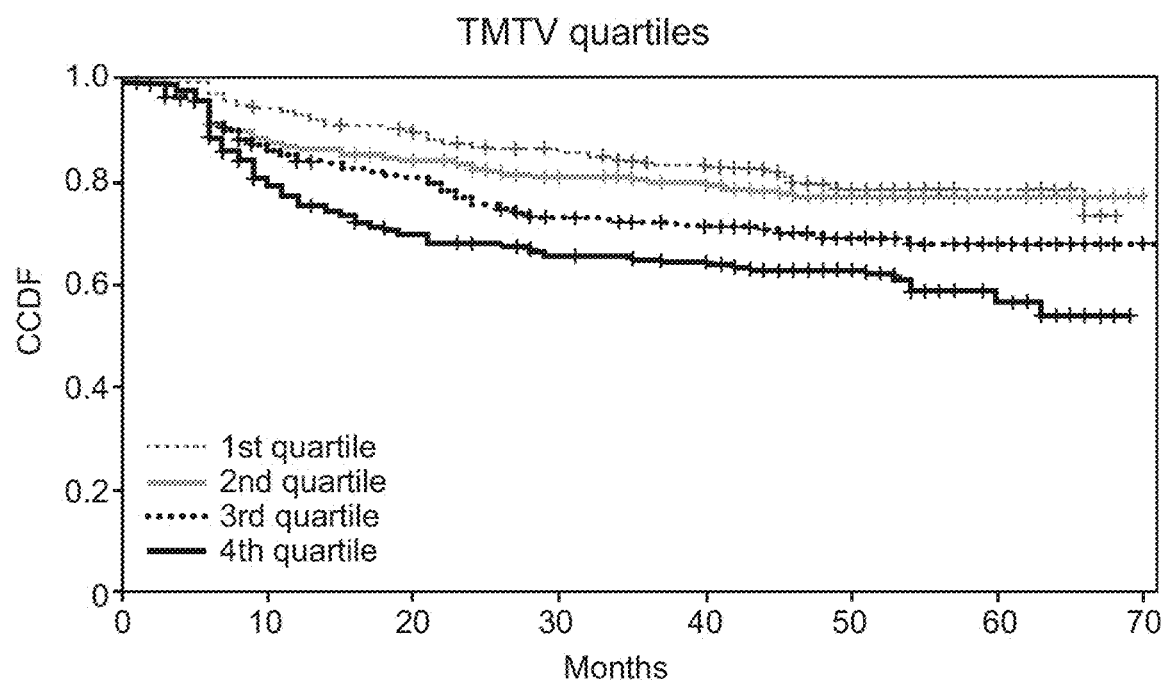
Figure 12A:
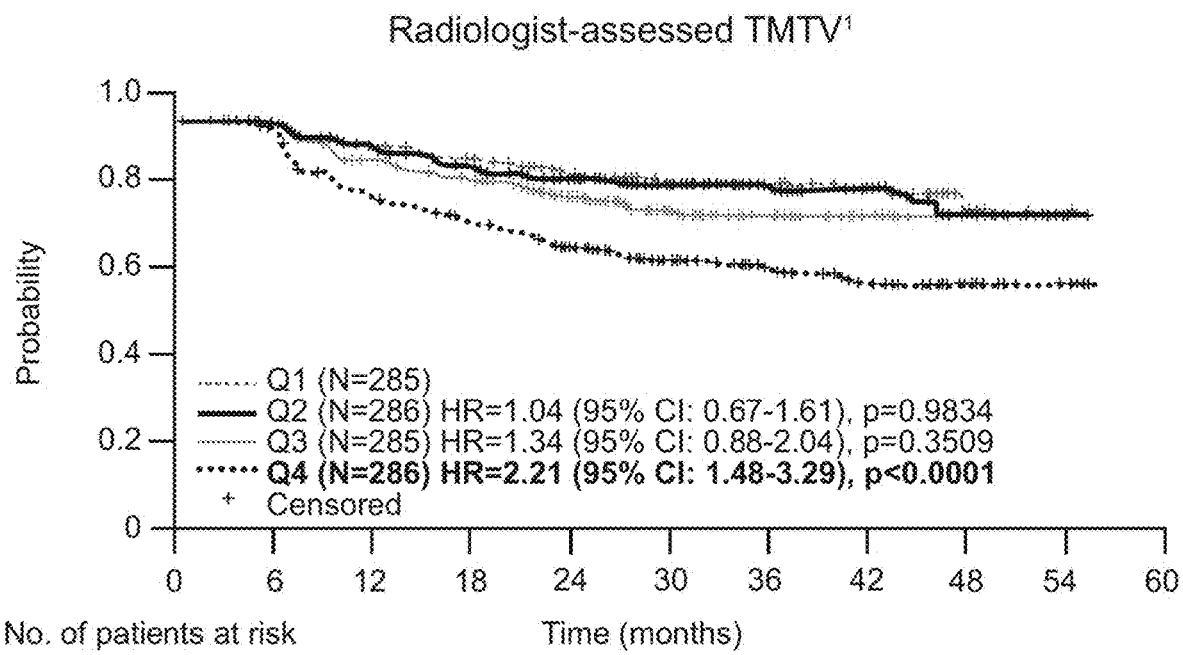
FIGS. 12A and 12B show automated TMTV provides prognostic metrics at baseline, consistent with manual TMTV assessments according to various embodiments.
Figure 12B:
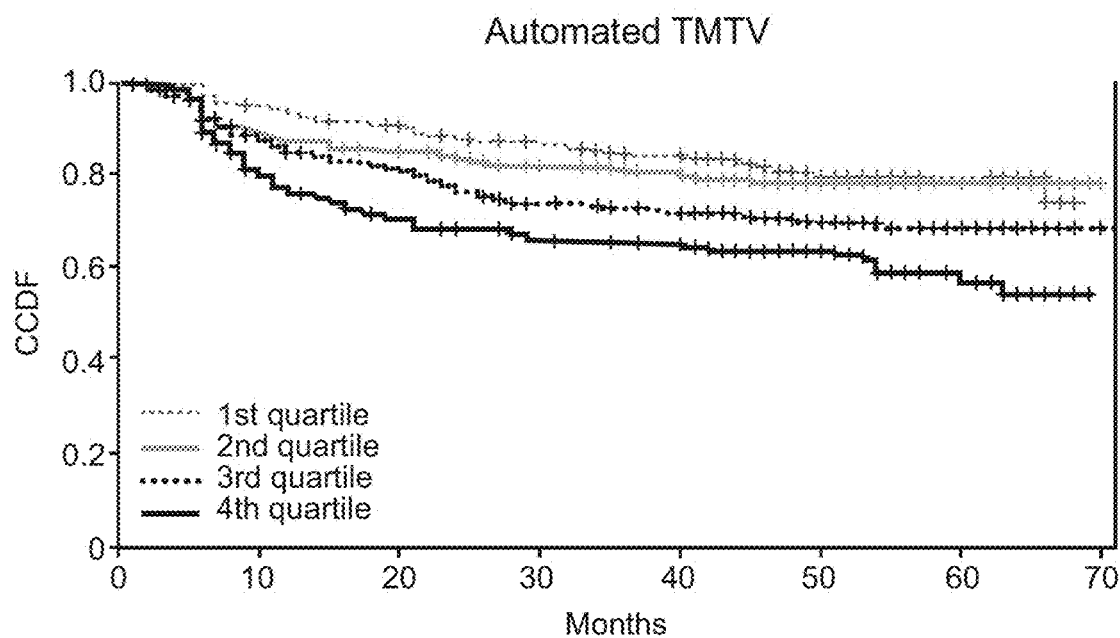
Figure 13B:
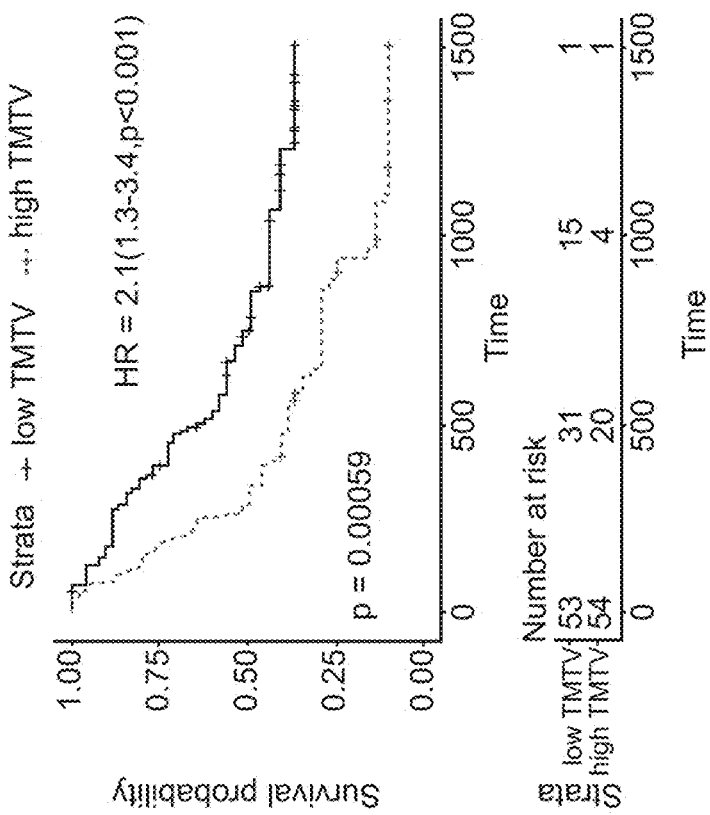
FIGS. 13A and 13B show baseline TMTV is prognostic in non-small-cell lung carcinoma (NSCLC) and Melanoma according to various embodiments.
Figure 13A:
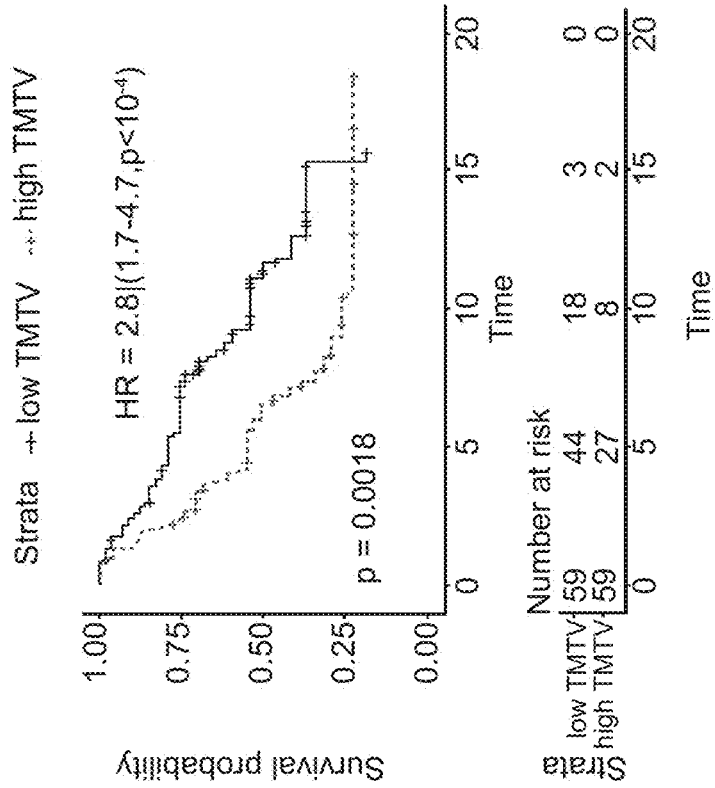

FIGS. 10A and 10B illustrate tumor volume and $SUV_{max}$, respectively, from the predicted masks in accordance with this example embodiment. Tumor volume and SUVmax have been shown to have prognostic value. Specifically, K-means clustering on the algorithm-predicted TMTV values identified signatures with slower to more rapid PFS. The K-means approach identified 4 distinct clusters based on the predicted baseline TMTV. FIGS. 11A and 11B illustrate Kaplan-Meier estimators of these clusters showing the relevance of the TMTV for prognosis, in accordance with the example embodiment. At the subject level, these clusters were more discriminative than clusters using simple TMTV quartiles or the maximal SUV or Total Lesion Glycolysis. FIGS. 12A and 12B illustrate that automated TMTV provides prognostic metrics at baseline, consistent with manual TMTV assessments. The ability to automatically and accurately quantify these prognostic metrics enables rapid integration with other clinical markers and may facilitate clinical trial stratification, and time and cost savings. FIGS. 13A and 13B illustrate that baseline TMTV is prognostic in NSCLC and Melanoma.

V.G. Example 2. —Independent Prognostic Value of an Automated Assessment of Extranodal Involvement in Diffuse Large B-Cell Lymphoma and Follicular Lymphoma The presence of extranodal disease as detected by FDG-PET/CT in DLBCL and FL is associated with poor outcomes. Use of FDG-PET/CT to detect tumors and assess metabolic activity in lymphoma requires accurate and reproducible quantitative image interpretation tools. In accordance with various aspects discussed herein, a model architecture is provided for fully automated tumor and organ segmentation in PET/CT images and prognostication of subjects with DLBCL and FL based on organ (liver, spleen, and kidneys) specific metabolic tumor burden.

V.H. Data

The data set is comprised of a total of 1,139 pre-treatment PET/CT scans from a GOYA study in DLBCL (NCT01287741) and 541 pre-treatment scans from a GALLIUM study in FL (NCT01332968). Data was stored in the DICOM format.

V.I. Method

An image processing pipeline comprising two-dimensional and three-dimensional cascaded convolutional neural networks was trained on the GOYA set of data and tested on the GALLIUM set of data for tumor segmentation. Three-dimensional cascaded convolutional neural networks were also trained on publicly available datasets for liver, spleen, and kidney segmentations (validation DSC=0.94, 0.95, and 0.91, respectively). Segmentations allowed for extraction of total metabolic tumor volume (TMTV) and organ-specific measurements for the spleen, liver, and kidneys (metabolic tumor volume [MTV] and number of lesions>1 mL). Organ involvement was defined as an automated organ MTV>0.1 mL for noise reduction purposes. Kaplan-Meier analysis was used to assess progression-free survival (PFS) and a Cox proportional hazards model was used to estimate prognostic value of organ-specific involvement.

V.J. Results

Figure 14A:
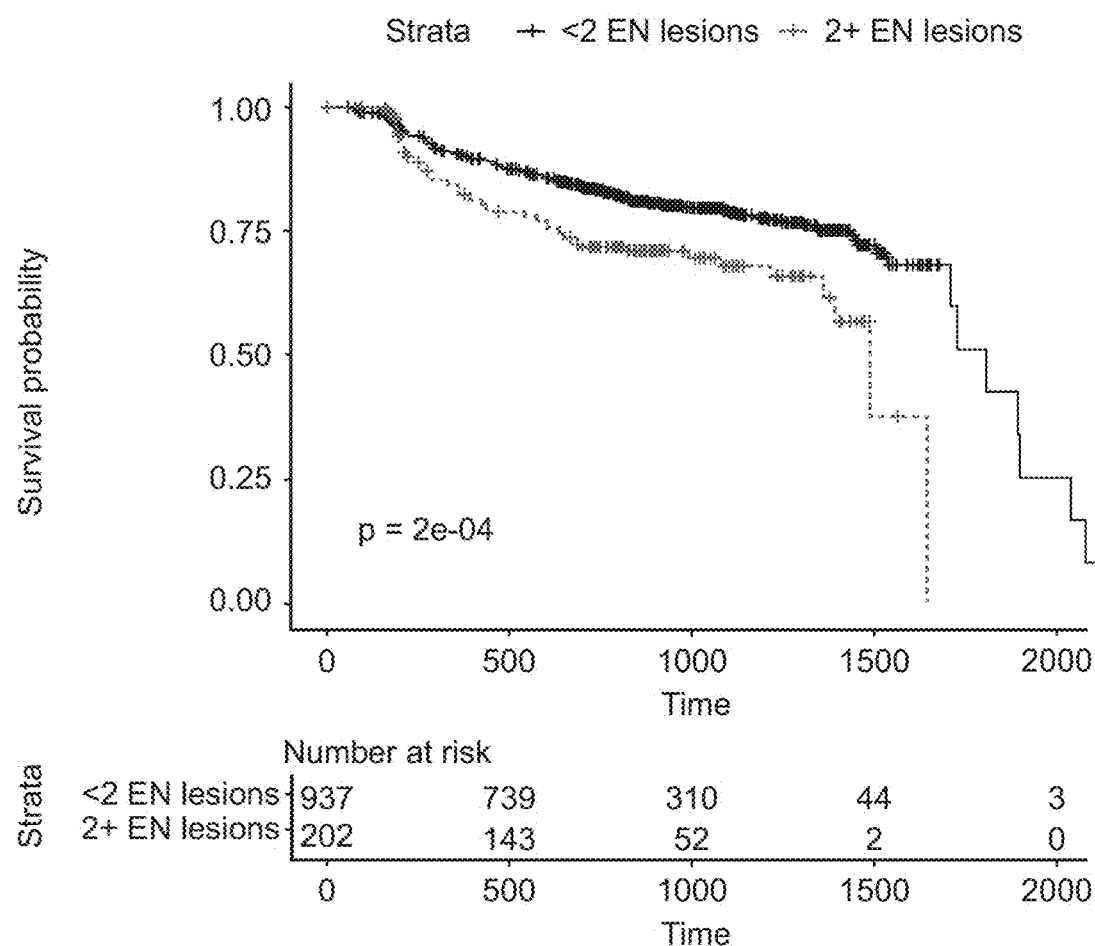
FIGS. 14A-F show Kaplan-Meier analysis of association of extranodal involvement with progression-free survival probability in the GOYA (A-C) and GALLIUM (D-E) studies in accordance with various embodiments.
Figure 14B:
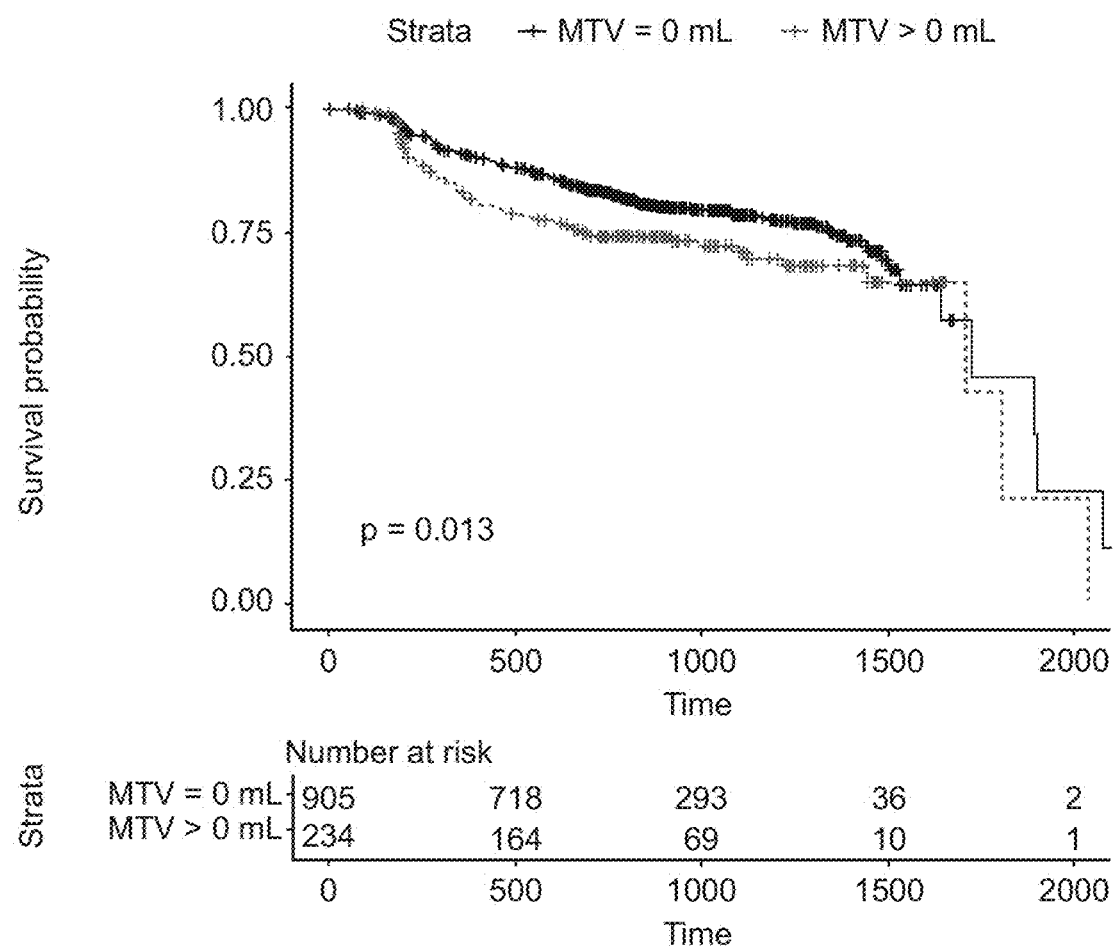
Figure 14C:
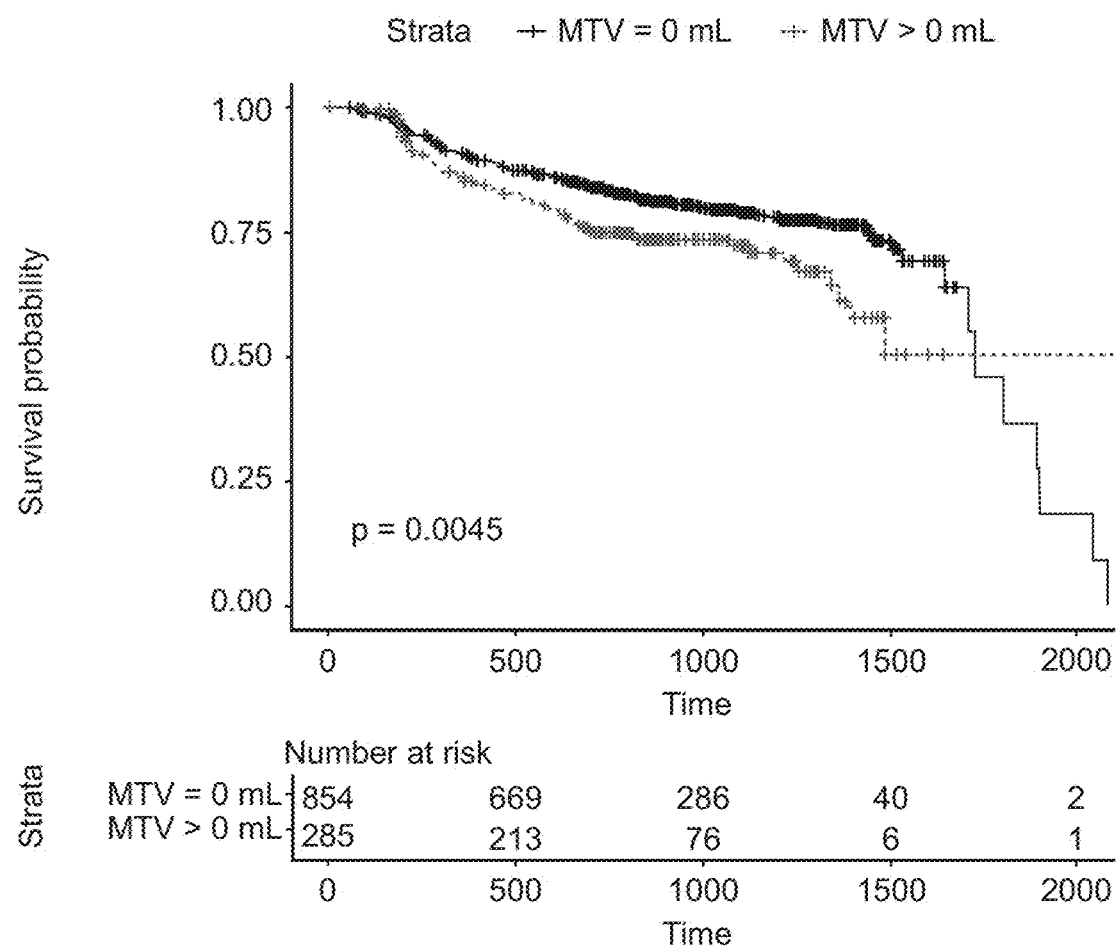

Automated analysis of the pre-treatment PET/CT scans from the GOYA study showed that the presence of ≥2 lesions>1 mL in the liver and/or spleen was associated with lower PFS in univariate analysis (Hazard Ratio, HR=1.73; 95% Confidence Interval, CI=1.29-2.32; p=0.0002). This association was maintained in multivariate analysis after adjustment for TMTV>median and ≥2 extranodal lesions in the liver/spleen (HR=1.52; 95% CI=1.10-2.07; p=0.009) and after adjustment for International Prognostic Index (IPI), cell of origin (COO) and imaging-derived features (≥2 extranodal sites: HR=1.49; 95% CI=1.02-2.18; p=0.037). Kaplan-Meier analysis also demonstrated that extranodal involvement (≥2 extranodal lesions in the liver and/or spleen) was significantly associated with poorer PFS in GOYA (FIG. 14A). Liver and kidney involvement were both prognostic by univariate analysis in DLBCL (HR=1.48; 95% CI=1.13-1.94; p=0.004 and HR=1.44; 95% CI=1.08-1.91; p=0.013, respectively, and FIGS. 14B and 14C); however, splenic involvement was not prognostic. Multivariate analysis also confirmed the prognostic value of liver and kidney involvement for PFS when adjusting for imaging-derived factors (HR=1.40; 95% CI=1.06-1.85; p=0.017 and HR=1.34; 95% CI=1.00-1.80; p=0.049, respectively).

Figure 14D:
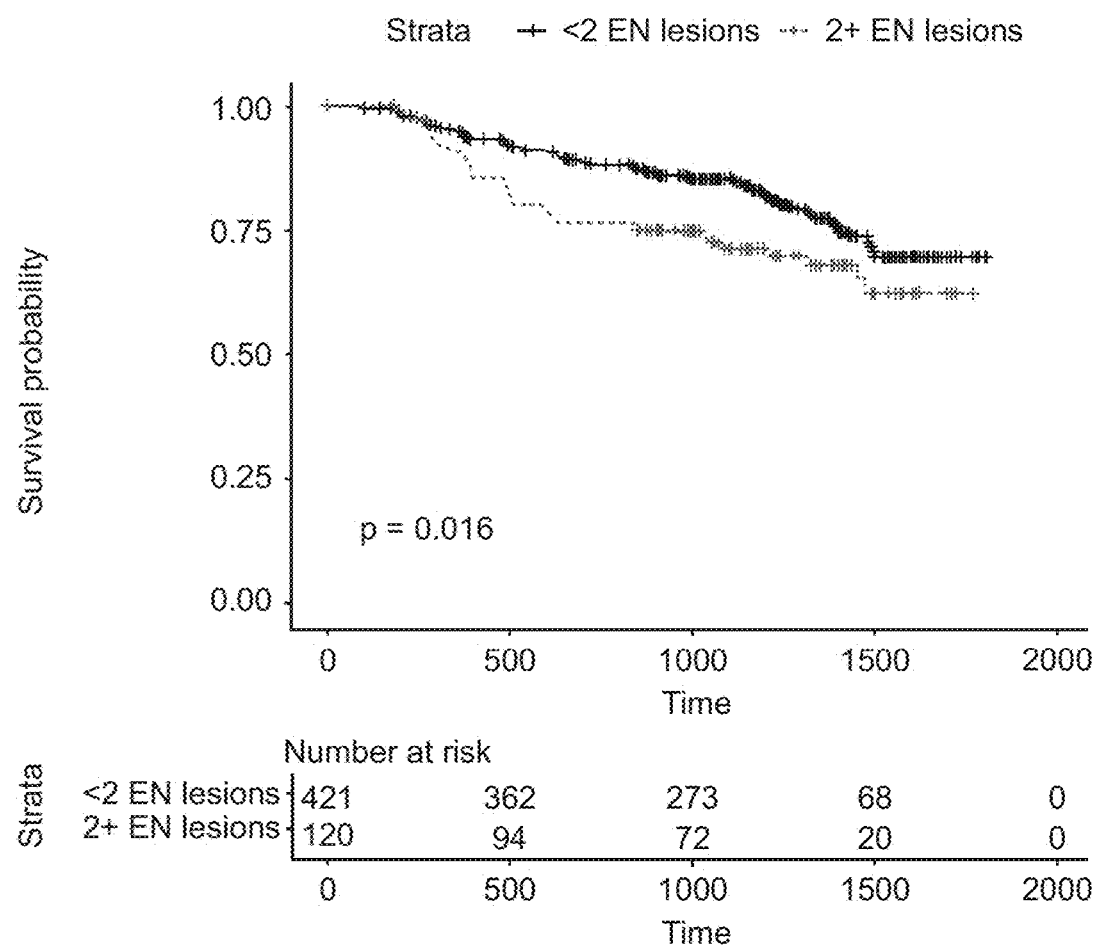
Figure 14E:
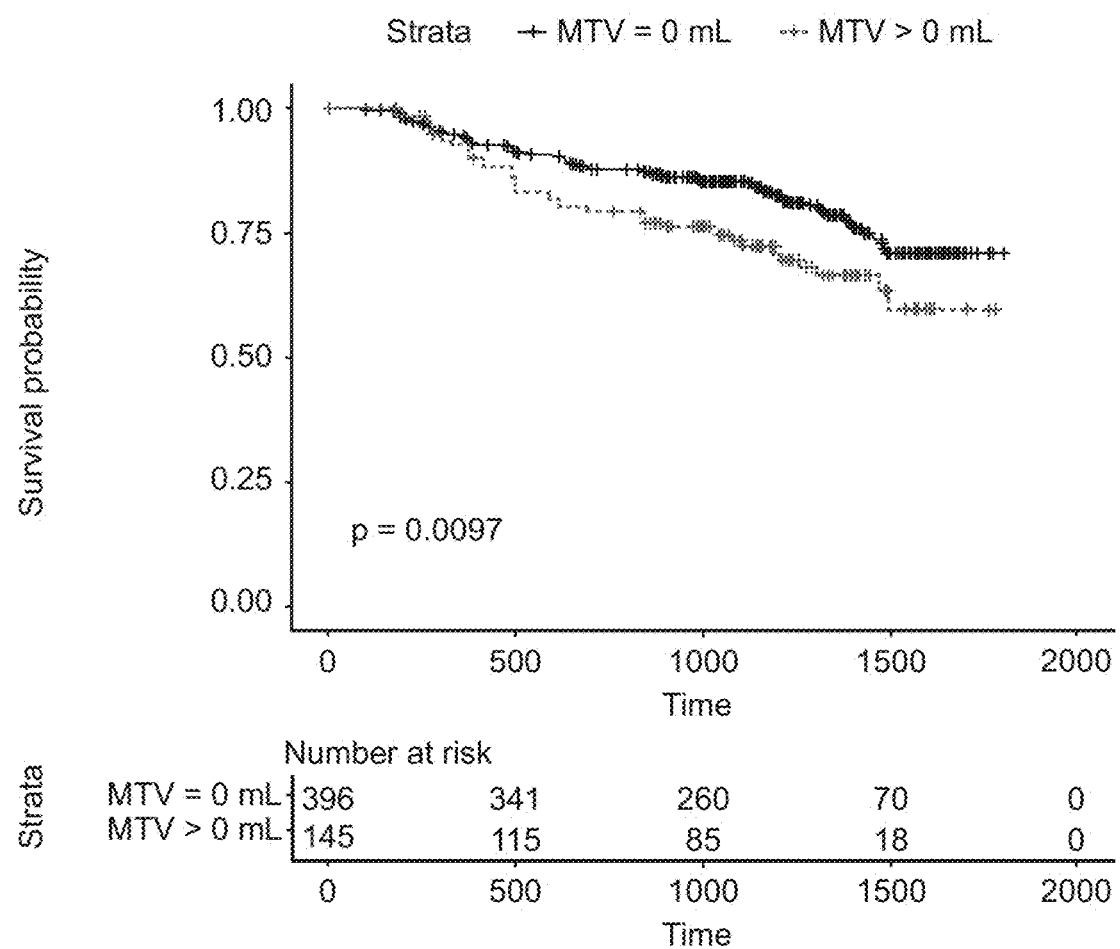
Figure 14F:
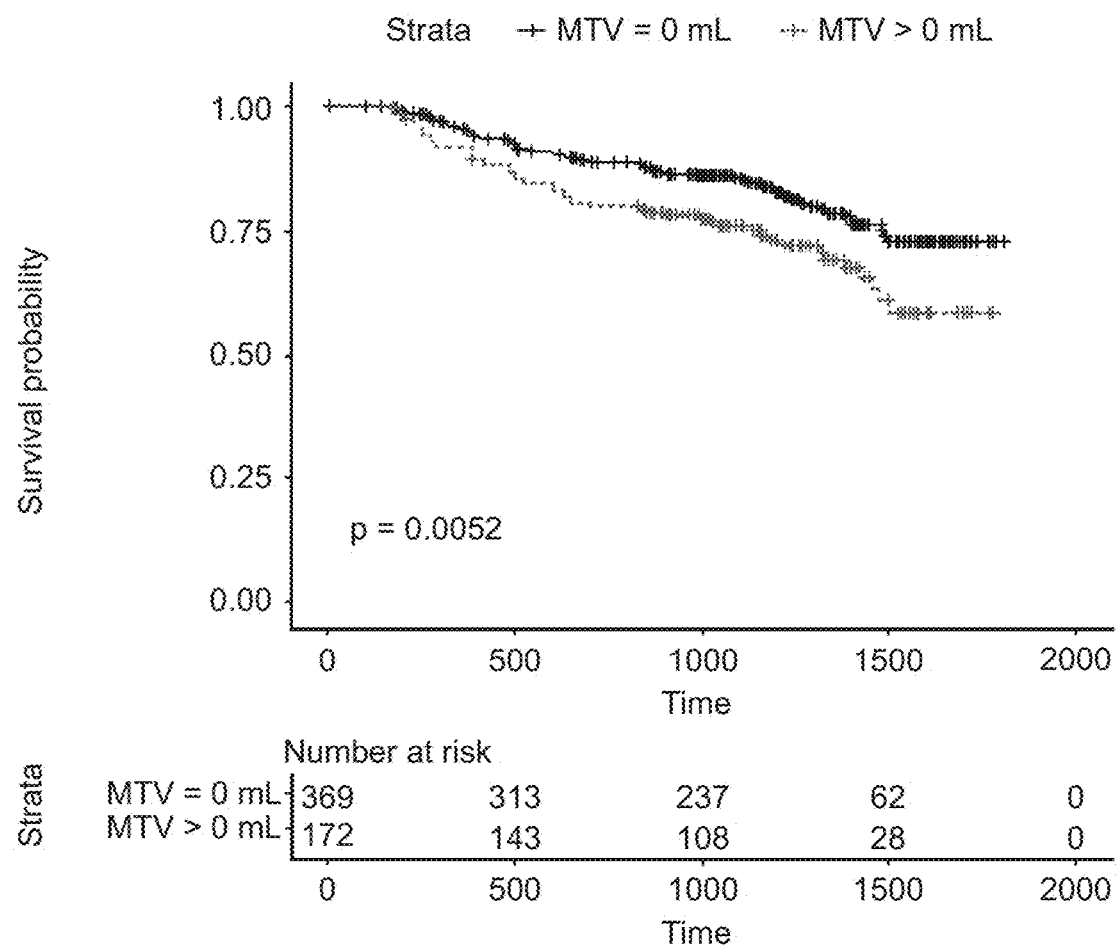

In subjects with FL from the GALLIUM study, ≥2 lesions>1 mL in liver and/or spleen was associated with PFS by univariate analysis (HR=1.61; 95% CI=1.09-2.38; p=0.017) and by Kaplan-Meier analysis (FIG. 14D). Liver and splenic involvement were also prognostic by univariate analysis (HR=1.64; 95% CI=1.12-2.38; p=0.010 and HR=1.67; 95% CI=1.16-2.40; p=0.006, respectively, and FIGS. 14E and 14F), but kidney involvement was not prognostic in FL. When adjusting for imaging-derived features, multivariate analysis showed that splenic involvement remained prognostic for PFS (HR=1.51; 95% CI=1.03-2.21; p=0.034); however, liver involvement was no longer significantly associated (HR=1.44; 95% CI=0.97-2.14; p=0.068). When adjusting for Follicular Lymphoma International Prognostic Index (FLIPI), liver involvement remained prognostic (HR=1.52; 95% CI=1.03-2.23; p=0.036).

In subjects with DLBCL from GOYA, automated analysis of PET/CT demonstrated that the presence of ≥2 extranodal lesions in liver and/or spleen is an independent prognostic factor and adds prognostic value to TMTV>median, IPI, and COO. Splenic involvement alone was not prognostic in DLBCL. In subjects with FL, extranodal involvement (≥2 lesions in liver and/or spleen) and the presence of splenic lesions were independent prognostic factors.

VI. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method comprising:

obtaining a plurality of positron emission tomography (PET) scans and a plurality of computerized tomography (CT) or magnetic resonance imaging (MRI) scans for a subject;

preprocessing the PET scans and the CT or MRI scans to generate a first subset of standardized images for a first plane or region of the subject and a second subset of standardized images for a second plane or region of the subject, wherein the first subset of standardized images and the second subset of standardized images incorporate information from the PET scans and the CT or MRI scans;

generating a first two-dimensional segmentation mask, using a first two-dimensional segmentation model implemented as part of a convolutional neural network architecture that takes as input the first subset of standardized images, wherein the first two-dimensional segmentation model is trained for processing images for the first plane or region using a first residual block comprising a first layer that: (i) feeds directly into a subsequent layer, and (ii) uses a skip connection to feed directly into a layer that is multiple layers away from the first layer;

generating a second two-dimensional segmentation mask, using a second two-dimensional segmentation model implemented as part of the convolutional neural network architecture that takes as input the second subset of standardized images, wherein the second two-dimensional segmentation model is trained for processing images for the second plane or region using a second residual block comprising a second layer that: (i) feeds directly into a subsequent layer, and (ii) uses a skip connection to feed directly into a layer that is multiple layers away from the second layer;

generating a three-dimensional segmentation mask, using one or more three-dimensional segmentation models implemented as part of the convolutional neural network architecture, for each patch of image data associated with a segment of a plurality of segments from the first two-dimensional segmentation mask and the second two-dimensional segmentation mask, wherein each segment is a pixel-wise or voxel-wise mask for a classified object in the first two-dimensional segmentation mask or the second two-dimensional segmentation mask; and generating, by a classifier, a final imaged mask by combining information from the first two-dimensional segmentation mask, the second two-dimensional segmentation mask, and each of the three-dimensional segmentation masks for each patch of the image data.

2. The method of claim 1, wherein the first layer and the second layer are pyramidal layers with separable convolutions performed at one or more levels of dilation.

3. The method of claim 1, further comprising determining, using the final imaged mask, a total metabolic tumor burden (TMTV), and providing the TMTV.

4. The method of claim 1, wherein the patches of image data comprise a first patch of image data associated with a first segment located in a first anatomical region and a second patch of image data associated with a second segment located in a second anatomical region, and wherein the generating the three-dimensional segmentation mask for each patch of image data comprises:
   generating a first three-dimensional segmentation mask, using a first three-dimensional segmentation model that takes as input the first patch of image data, wherein the first three-dimensional segmentation model is trained for processing image data from the first anatomical region; and
   generating a second three-dimensional segmentation mask, using a second three-dimensional segmentation model that takes as input the second patch of image data, wherein the second three-dimensional segmentation model is trained for processing image data from the second anatomical region.

5. The method of claim 1, further comprising:
determining a TMTV using the final imaged mask;
determining, using the final imaged mask and the three-dimensional segmentation masks, a metabolic tumor burden (MTV) and number of lesions for one or more organs in the three-dimensional segmentation masks; and
using a classifier that takes as input one or more of the TMTV, the MTV, and the number of lesions to generate a clinical prediction for the subject based on the one or more of the TMTV, the MTV, and the number of lesions,
wherein the clinical prediction is one of:
   a likelihood of progression free survival (PFS) for the subject;
   a disease stage of the subject; and
   a selection decision for including the subject in a clinical trial.

6. The method of claim 5, further comprising:
inputting the plurality of PET scans and CT or MRI scans for the subject into a data processing system comprising the convolutional neural network architecture; and
providing one or more of the final imaged mask, the TMTV, the MTV, and number of lesions.

7. The method of claim 6, further comprising administering a treatment to the subject based on the one or more of the final imaged mask, the TMTV, the MTV, and the number of lesions.

8. The method of claim 6, further comprising providing a diagnosis to the subject based on the one or more of the final imaged mask, the TMTV, the MTV, and the number of lesions.

9. A computer-program product tangibly embodied in a non-transitory machine-readable storage medium, including instructions configured to cause one or more data processors to perform actions including:
   obtaining a plurality of positron emission tomography (PET) scans and a plurality of computerized tomography (CT) or magnetic resonance imaging (MRI) scans for a subject;
   preprocessing the PET scans and the CT or MRI scans to generate a first subset of standardized images for a first plane or region of the subject and a second subset of standardized images for a second plane or region of the subject, wherein the first subset of standardized images and the second subset of standardized images incorporate information from the PET scans and the CT or MRI scans;
   generating a first two-dimensional segmentation mask, using a first two-dimensional segmentation model implemented as part of a convolutional neural network architecture that takes as input the first subset of standardized images, wherein the first two-dimensional segmentation model is trained for processing images for the first plane or region using a first residual block comprising a first layer that: (i) feeds directly into a subsequent layer, and (ii) uses a skip connection to feed directly into a layer that is multiple layers away from the first layer;
   generating a second two-dimensional segmentation mask, using a second two-dimensional segmentation model implemented as part of the convolutional neural network architecture that takes as input the second subset of standardized images, wherein the second two-dimensional segmentation model is trained for processing images for the second plane or region using a second residual block comprising a second layer that: (i) feeds directly into a subsequent layer, and (ii) uses a skip connection to feed directly into a layer that is multiple layers away from the second layer;
   generating a three-dimensional segmentation mask, using one or more three-dimensional segmentation models implemented as part of the convolutional neural network architecture, for each patch of image data associated with a segment of a plurality of segments from the first two-dimensional segmentation mask and the second two-dimensional segmentation mask, wherein each segment is a pixel-wise or voxel-wise mask for a classified object in the first two-dimensional segmentation mask or the second two-dimensional segmentation mask; and
   generating, by a classifier, a final imaged mask by combining information from the first two-dimensional segmentation mask, the second two-dimensional segmentation mask, and each of the three-dimensional segmentation masks for each patch of the image data.

10. The computer-program product of claim 9, wherein the first layer and the second layer are pyramidal layers with separable convolutions performed at one or more levels of dilation.

11. The computer-program product of claim 9, wherein the actions further comprise determining, using the final imaged mask, a total metabolic tumor burden (TMTV), and providing the TMTV.

12. The computer-program product of claim 9, wherein the patches of image data comprise a first patch of image data associated with a first segment located in a first anatomical region and a second patch of image data associated with a second segment located in a second anatomical region, and wherein the generating the three-dimensional segmentation mask for each patch of image data comprises:
   generating a first three-dimensional segmentation mask, using a first three-dimensional segmentation model that takes as input the first patch of image data, wherein the first three-dimensional segmentation model is trained for processing image data from the first anatomical region; and generating a second three-dimensional segmentation mask, using a second three-dimensional segmentation model that takes as input the second patch of image data, wherein the second three-dimensional segmentation model is trained for processing image data from the second anatomical region.

13. The computer-program product of claim 9, wherein the actions further comprise:
determining a TMTV using the final imaged mask;
determining, using the final imaged mask and the three-dimensional segmentation masks, a metabolic tumor burden (MTV) and number of lesions for one or more organs in the three-dimensional segmentation masks; and
using a classifier that takes as input one or more of the TMTV, the MTV, and the number of lesions to generate a clinical prediction for the subject based on the one or more of the TMTV, the MTV, and the number of lesions,
wherein the clinical prediction is one of:
a likelihood of progression free survival (PFS) for the subject;
a disease stage of the subject; and
a selection decision for including the subject in a clinical trial.

14. The computer-program product of claim 13, wherein the actions further comprise:
inputting the plurality of PET scans and CT or MRI scans for the subject into a data processing system comprising the convolutional neural network architecture; and
providing one or more of the final imaged mask, the TMTV, the MTV, and number of lesions.

15. A system comprising:
one or more data processors; and
a non-transitory computer readable storage medium containing instructions which, when executed on the one or more data processors, cause the one or more data processors to perform actions including:
obtaining a plurality of positron emission tomography (PET) scans and a plurality of computerized tomography (CT) or magnetic resonance imaging (MRI) scans for a subject; preprocessing the PET scans and the CT or MRI scans to generate a first subset of standardized images for a first plane or region of the subject and a second subset of standardized images for a second plane or region of the subject, wherein the first subset of standardized images and the second subset of standardized images incorporate information from the PET scans and the CT or MRI scans;
generating a first two-dimensional segmentation mask, using a first two-dimensional segmentation model implemented as part of a convolutional neural network architecture that takes as input the first subset of standardized images, wherein the first two-dimensional segmentation model is trained for processing images for the first plane or region using a first residual block comprising a first layer that: (i) feeds directly into a subsequent layer, and (ii) uses a skip connection to feed directly into a layer that is multiple layers away from the first layer;
generating a second two-dimensional segmentation mask, using a second two-dimensional segmentation model implemented as part of the convolutional neural network architecture that takes as input the second subset of standardized images, wherein the second two-dimensional segmentation model is trained for processing images for the second plane or region using a second residual block comprising a second layer that: (i) feeds directly into a subsequent layer, and (ii) uses a skip connection to feed directly into a layer that is multiple layers away from the second layer;
generating a three-dimensional segmentation mask, using one or more three-dimensional segmentation models implemented as part of the convolutional neural network architecture, for each patch of image data associated with a segment of a plurality of segments from the first two-dimensional segmentation mask and the second two-dimensional segmentation mask, wherein each segment is a pixel-wise or voxel-wise mask for a classified object in the first two-dimensional segmentation mask or the second two-dimensional segmentation mask; and
generating, by a classifier, a final imaged mask by combining information from the first two-dimensional segmentation mask, the second two-dimensional segmentation mask, and each of the three-dimensional segmentation masks for each patch of the image data.

16. The system of claim 15, wherein the first layer and the second layer are pyramidal layers with separable convolutions performed at one or more levels of dilation.

17. The system of claim 15, wherein the actions further comprise determining, using the final imaged mask, a total metabolic tumor burden (TMTV), and providing the TMTV.

18. The system of claim 15, wherein the patches of image data comprise a first patch of image data associated with a first segment located in a first anatomical region and a second patch of image data associated with a second segment located in a second anatomical region, and wherein the generating the three-dimensional segmentation mask for each patch of image data comprises:
generating a first three-dimensional segmentation mask, using a first three-dimensional segmentation model that takes as input the first patch of image data, wherein the first three-dimensional segmentation model is trained for processing image data from the first anatomical region; and
generating a second three-dimensional segmentation mask, using a second three-dimensional segmentation model that takes as input the second patch of image data, wherein the second three-dimensional segmentation model is trained for processing image data from the second anatomical region.

19. The system of claim 15, wherein the actions further comprise:
determining a TMTV using the final imaged mask;
determining, using the final imaged mask and the three-dimensional segmentation masks, a metabolic tumor burden (MTV) and number of lesions for one or more organs in the three-dimensional segmentation masks; and
using a classifier that takes as input one or more of the TMTV, the MTV, and the number of lesions to generate a clinical prediction for the subject based on the one or more of the TMTV, the MTV, and the number of lesions,
wherein the clinical prediction is one of:
a likelihood of progression free survival (PFS) for the subject;
a disease stage of the subject; and
a selection decision for including the subject in a clinical trial.

20. The system of claim 19, wherein the actions further comprise:
  inputting the plurality of PET scans and CT or MRI scans for the subject into a data processing system comprising the convolutional neural network architecture; and
  providing one or more of the final imaged mask, the TMTV, the MTV, and number of lesions.

* * * * *